US006458775B1

(12) United States Patent
Jackson et al.

(10) Patent No.: US 6,458,775 B1
(45) Date of Patent: Oct. 1, 2002

(54) NAALADASE INHIBITORS USEFUL AS PHARMACEUTICAL COMPOUNDS AND COMPOSITIONS

(75) Inventors: Paul F. Jackson, Bel Air; Keith M. Maclin; Eric Wang, both of Baltimore; Barbara S. Slusher, Kingsville; Rena S. Lapidus, Baltimore; Pavel Majer, Sykesville, all of MD (US)

(73) Assignee: Guilford Pharmaceutical Inc., Baltimore, MD (US)

( * ) Notice: Subject to any disclaimer, the term of this patent is extended or adjusted under 35 U.S.C. 154(b) by 0 days.

(21) Appl. No.: 09/346,711

(22) Filed: Jul. 2, 1999

Related U.S. Application Data

(63) Continuation-in-part of application No. 09/228,391, filed on Jan. 12, 1999, and a continuation-in-part of application No. 09/110,262, filed on Jul. 6, 1998, which is a continuation-in-part of application No. 09/110,186, filed on Jul. 6, 1998.

(51) Int. Cl.$^7$ .................. A61K 31/66; A61K 31/435; A61K 31/19

(52) U.S. Cl. .................. 514/75; 514/143; 514/277; 514/574

(58) Field of Search .................. 514/75, 143, 277, 514/574

(56) References Cited

U.S. PATENT DOCUMENTS

| | | |
|---|---|---|
| 4,151,172 A | 4/1979 | Ondetti et al. |
| 4,168,267 A | 9/1979 | Petrillo, Jr. |
| 4,316,896 A | 2/1982 | Thorsett et al. |
| 4,337,201 A | 6/1982 | Petrillo, Jr. |
| 4,374,131 A | 2/1983 | Petrillo, Jr. |
| 4,444,765 A | 4/1984 | Karanewsky et al. |
| 4,448,772 A | 5/1984 | Karenewsky |
| 4,452,790 A | 6/1984 | Karanewsky et al. |
| 4,452,791 A | 6/1984 | Ryono et al. |
| 4,468,519 A | 8/1984 | Krapcho |
| 4,547,324 A | 10/1985 | Wong et al. |
| 4,555,506 A | 11/1985 | Karanewsky et al. |
| 4,560,680 A | 12/1985 | Ryono et al. |
| 4,560,681 A | 12/1985 | Karanewsky |
| 4,567,166 A | 1/1986 | Karanewsky et al. |
| 4,616,005 A | 10/1986 | Karanewsky et al. |
| 4,671,958 A | 6/1987 | Rodwell et al. |
| 4,703,043 A | 10/1987 | Karanewsky et al. |
| 4,715,994 A | 12/1987 | Parsons et al. |
| 4,716,155 A | 12/1987 | Karanewsky et al. |

(List continued on next page.)

FOREIGN PATENT DOCUMENTS

| | | |
|---|---|---|
| EP | 0 002 219 A1 | 11/1978 |
| EP | 0 416 373 A2 | 8/1990 |
| WO | WO 95/23806 | 9/1995 |
| WO | WO 96/26272 | 8/1996 |
| WO | WO 98 13044 A | 4/1998 |

OTHER PUBLICATIONS

Stauch, B., et al., "The effects of N–acetylated alpha–linked acidic dipeptidase (NAALADase) inhibitors on [$^3$H]NAAG catabolism in vivo," *Neuroscience Letters,* 100, pp. 295–300 (1989).

Subasinghe, N., et al., "Synthesis of Acyclic and Dehydroaspartic Acid Analogues of Ac–Asp–Glu–OH and Their Inhibition of Rat Brain N–Acetylated α–Linked Acidic Dipeptidase (NAALA Dipeptidase)," *J. Med. Chem.,* 33, pp. 2734–2744 (1990).

Rothstein, J., et al., "Abnormal Excitatory Amino Acid Metabolism In Amyotrophic Lateral Sclerosis," *Annals of Neurology,* vol. 28, pp. 18–25 (1990).

Slusher, B., et al., "Rat Brain N–Acetylated α–Linked Acidic Dipeptidase Activity," *J. of Biological Chemistry,* vol. 265, No. 34, p. 21297–21301 (1990).

Tsai, G., et al., "Reductions in acidic amino acids and N–acetylaspartylglutamate in amyotrophic lateral sclerosis CNA," *Brain Research,* 556, pp. 151–156 (1991).

Coyle, J., et al., "N–Acetyl–aspartyl Glutamate," *Excitatory Amino Acids,* pp. 69–77 (1991).

Meyerhoff, J., et al., "Genetically epilepsy–prone rats have increased brain regional activity of an enzyme which liberates glutamate from N–acetyl–aspartyl–glutamate", *Brain Research,* 593, pp. 140–143 (1992).

Meyerhoff, J., et al., Activity of a NAAG–hydrolyzing enzyme in brain may affect seizure susceptibility in genetically epilepsy–prone rats, *Molecular Neurobiology of Epilepsy,* pp. 163–172 (1992).

Slusher, B., et al., "Immunocytochemical Localization Of The N–Acetyl–Aspartyl–Glutamate (NAAG) Hydrolyzing Enzynme N–Acetylated α–Linked Acidic Dipeptidase (NAALADase)," *J. of Comp. Neurology,* 315, pp. 217–229 (1992).

Tsai, G., et al., "Immunocytochemical Distribution of N–Acetylaspartylglutamate in the Rat Forebrain and Glutamergic Pathways," *J. of Chem. Neuroanatomy,* 6, pp. 277–292 (1993).

Tsai, G., et al., "Changes of excitatory neurotransmitter metabolism in schizophrenic brains," *Salmon Lecturer of the New York Academy of Medicine* (Dec. 2–3, 1993).

Slusher, B., et al., "NAALADase: A Potential Regulator of Synaptic Glutamate," *Biotech Update DuPont NEN,* 9, pp. 37–39 (1994).

(List continued on next page.)

*Primary Examiner*—Frederick Krass
*Assistant Examiner*—Donna Jagoe
(74) *Attorney, Agent, or Firm*—Lyon & Lyon LLP

(57) ABSTRACT

The present invention relates to N-Acetylated α-Linked Acidic Dipeptidase (NAALADase) inhibitors enzyme activity, pharmaceutical compositions comprising such inhibitors, and methods of their use to inhibit NAALADase enzyme activity, thereby effecting neuronal activities, inhibiting angiogenesis, and treating glutamate abnormalities, compulsive disorders, prostate diseases, pain and diabetic neuropathy.

55 Claims, 28 Drawing Sheets

U.S. PATENT DOCUMENTS

| | | | |
|---|---|---|---|
| 4,741,900 A | 5/1988 | Alvarez et al. | |
| 4,758,584 A | 7/1988 | Bühlmayer et al. | 514/400 |
| 4,849,525 A | 7/1989 | Weller, III et al. | |
| 4,853,326 A | 8/1989 | Quash et al. | |
| 4,867,973 A | 9/1989 | Goers et al. | |
| 4,885,283 A | 12/1989 | Broadhurst et al. | |
| 4,906,779 A | 3/1990 | Weber et al. | |
| 4,918,064 A | 4/1990 | Cordi et al. | |
| 4,927,966 A | 5/1990 | Kalman | |
| 4,937,183 A | 6/1990 | Ultee et al. | |
| 4,950,738 A | 8/1990 | King et al. | |
| 4,959,493 A | 9/1990 | Ohfume et al. | |
| 4,962,097 A | 10/1990 | Parsons et al. | |
| 4,966,999 A | 10/1990 | Coughlin et al. | |
| 4,988,681 A | 1/1991 | Ishikawa et al. | |
| 4,994,446 A | 2/1991 | Sokolovsky et al. | |
| 5,030,732 A | 7/1991 | Morita et al. | |
| 5,041,644 A | 8/1991 | Morita et al. | |
| 5,047,227 A | 9/1991 | Rodwell et al. | |
| 5,061,806 A | 10/1991 | Morita et al. | |
| 5,093,525 A | 3/1992 | Weber et al. | |
| 5,099,063 A | 3/1992 | Parsons et al. | |
| 5,136,080 A | 8/1992 | Miller et al. | |
| 5,140,104 A | 8/1992 | Coughlin et al. | |
| 5,143,908 A | 9/1992 | Parsons et al. | |
| 5,145,990 A | 9/1992 | Parsons et al. | |
| 5,147,867 A | 9/1992 | Parsons et al. | |
| 5,156,840 A | 10/1992 | Goers et al. | |
| 5,162,504 A | 11/1992 | Horoszewicz | |
| 5,162,512 A | 11/1992 | King et al. | |
| 5,190,976 A | 3/1993 | Weber et al. | |
| 5,196,510 A | 3/1993 | Rodwell et al. | |
| 5,242,915 A | 9/1993 | Ueda et al. | |
| 5,262,568 A | 11/1993 | Weber et al. | |
| H1312 H | 5/1994 | Coughlin et al. | |
| 5,326,856 A | 7/1994 | Coughlin et al. | |
| 5,336,689 A | 8/1994 | Weber et al. | |
| 5,449,761 A | 9/1995 | Belinka, Jr. et al. | |
| 5,474,547 A | 12/1995 | Aebischer et al. | |
| 5,489,525 A | 2/1996 | Pastan | |
| 5,495,042 A | 2/1996 | Belinka, Jr. et al. | |
| 5,500,420 A | 3/1996 | Maiese | |
| 5,508,273 A | 4/1996 | Beers et al. | |
| 5,527,885 A | 6/1996 | Couglin et al. | |
| 5,538,866 A | 7/1996 | Israeli et al. | |
| 5,538,957 A | 7/1996 | Tsaklakidis et al. | |
| 5,672,592 A | 9/1997 | Jackson et al. | |
| 5,698,402 A | 12/1997 | Luderer et al. | |
| 5,795,877 A * | 8/1998 | Jackson et al. | 514/75 |
| 5,804,602 A | 9/1998 | Slusher et al. | 514/574 |
| 5,824,662 A | 10/1998 | Slusher et al. | 514/75 |
| 5,863,536 A | 1/1999 | Jackson et al. | 424/130.1 |
| 5,880,112 A | 3/1999 | Jackson et al. | 514/121 |
| 5,902,817 A | 5/1999 | Jackson et al. | 514/347 |
| 5,977,090 A * | 11/1999 | Slusher et al. | 514/143 |
| 6,017,903 A * | 1/2000 | Slusher et al. | 514/75 |
| 6,228,888 B1 * | 5/2001 | Slusher | 514/574 |

OTHER PUBLICATIONS

Koenig, M., et al., "N–acetyl–aspartyl–glutamate (NAAG) elicits rapid increase in intraneuronal $Ca^{2+}$ in vitro," NeuroReport, 5, pp. 1063–1068 (1994).

Jackson, P., et al., "Design, Synthesis, and Biological Activity of a Potent Inhibitor of the Neuropeptidase N–Acetylated α–Linked Acidic Dipeptidase," J. of Medicinal Chemistry, 39, pp. 619–622 (1996).

Vornov, J., et al., "Toxic NMDA–Receptor Activation Occurs During Recovery in a Tissue Culture Model of Ischemia," J. of Neurochemistry, 65, p. 1681–1691 (1995).

Woods, D., et al., "Gender–linked injury after focal cerebral ischemia," Soc. For Neuroscience 1996 Abstract Form (1996).

Bhardwaj, A., et al., "Striatal nitric oxide (NO) production is enhanced in focal cerebral ischemia: An in vivo microdialysis study," Soc. For Neuroscience 1996 Abstract Form (1996).

Heston, W., Bedeutung des prostataspezifischen Membranantigens (PSMA), Urologe, 35, pp. 400–407 (1996) (article in German).

Carter, R., et al., "Prostate–specific membrane antigen is a hydrolase with substrate and pharmacologic characteristics of neuropeptidase," Proc. Nat. Acad. Sci., 93, pp. 749–753 (1996).

Barren III, R., et al., "Method for Identifying Prostate Cells in Semen Using Flow Cytometry," The Prostate, 36, pp. 181–188 (1998).

Anderson, B., et al., "Anti–free radical mechanisms in captopril protection against reperfusion injury in isolated rat hearts," Can. J. Cardiol., 12(10), pp. 1099–1104 (1996).

Birincioglu, M., et al., Protective Effect of ACE Inhibitors on Ischemia–Reperfusion–induced Arrhythmias in Rats: Is this Effect Related to the Free Radical Scavenging Action of These Drugs?, Free Rad. Res., 27 (4), pp. 389–396 (1997).

Krishan, P., et al., "Effect of Angiotensin Converting Enzyme Inhibitors on Ischemia–Reperfusion–Induced Renal Injury in Rats," Pharmacological Research, 37(1), pp. 23–29 (1998).

Li, G.L., et al., Effect of Alpha–Phenyl–n–tert–butyl Nitrone (PBN) on Compression Injury of Rat Spinal Cord, Free Rad. Res., vol. 27, pp. 187–196 (1997).

Mizuno, A., et al., Inhibitory Effect of MCI–186, A Free Radical Scavenger, on Cerebral Ischemia Following Rat Middle Cerebral Artery Occlusion, Gen. Pharmac., vol. 30, No. 4, pp. 575–578 (1998).

La Penna, D., et al., Captopril has no Significant Scavenging Antioxidant Activity in Human Plasma in vitro or in vivo, Brit. J. Clin. Pharmacol., vol. 42, pp. 451–456 (1996).

Noda, Y., et al., Free Radical Scavenging Properties of Alacepril Metabolites and Lisinopril, Res. Comm. Mol. Path. Pharm., vol. 96, No. 2, pp. 125–136 (1997).

Packer, L., et al., "Neuroprotection by the Metabolic Antioxidant α–Lipoic Acid," Free Radical Bio. Med., vol. 22 (1/2), pp. 359–378 (1997).

de la Torre, J., et al., "Reversal of ischemic–induced chronic memory dysfunction in aging rats with a free radical scavenger–glycolytic intermediate combination," Brain Research, vol. 779, pp. 285–288 (1998).

Yamamoto, T., et al., Delayed neuronal death prevented by inhibition of increased hydroxyl radical formation in a transient cerebral ischemia, Brain Research, vol. 762, pp. 240–242 (1997).

Yuki, S., and Kogure, K., "The Changes of LCGU and rCBF in the MCA Occlusion–Recirculation Model in Rats and the Ameliorating Effect of MCI–186, A Novel Free Radical Scavenger," Mol. Chem. Neuropathology, vol. 32, pp. 123–128 (1997).

PCT International Search Report for International Application No. PCT/US99/15128, mailed Jul. 11, 2000.

Kim, D.H. et al., "The Structural Feature of $S_1$ Subsite of Carboxypeptidase A," Bioorg. Med. Chem. Lett., 1:6, 1991, pp. 317–322.

Kim, D.H. et al., "Synthesis and Inhibitory Activity of Optically Active 2–Benzyl–3–mercaptopropanoic Acid against Carboxypeptidase A," *Bioorg. Med. Chem. Lett.,* 3:12, 1993, pp. 317–322.

Database: Chemlabs Online, Chemical Abstracts Service, Columbus, Ohio, CAPLUS accession No. 1984:529861.

Database: Chemlabs Online, Chemical Abstracts Service, Columbus, Ohio, CAPLUS accession No. 1974:5178.

Database: Chemlabs Online, Chemical Abstracts Service, Columbus, Ohio, CAPLUS accession No. 1977:173424.

R. Zahradnik, "Die Reaktionen Von Aminosauren Mit Schwefelkohlenstoff IV. Der Zerfall Von Dithiocarbaminocarbonsauren Im Sauren Medium," *Coll. Czech. Chem. Commun.,.* 21, 1956, pp. 1111–1121.

Ishikawa, K. et al., "Studies on Optically Active Amino Acids. XIX. Solvent Effects on Optical Rotatory Dispersion and Circular Dichorism of N–Dithiocarbethoxy–L–$\alpha$–amino Acids," *Chem. Pharm. Bull.,* 1:5, 1971, pp. 912–929.

Suh, J. et al., "Zn(II)–Chelatimg Inhibitors of Carboxypeptidase A," *Bioorganic & Medicinal Chemistry Letters,* 5:6, 1995, pp. 585–588.

Kim, D.H. et al., "The Function of $S_1$ Subsite Pocket of Carboxypeptidase A," *Bioorg. Med. Chem. Lett.,* 1:6, 1991, pp. 323–326.

PCT Written Opinion for International Application No. PCT/US99/15128, mailed Sep. 12, 2000.

* cited by examiner

COMPOUND 3 ENHANCES MYELINATION
IN DORSAL ROOT - SCHWANN CELL CO-CULTURES

CONTROL

COMPOUND 3 ENHANCES MYELINATION
IN DORSAL ROOT - SCHWANN CELL CO-CULTURES

ASCORBIC ACID (50μg/ml)

COMPOUND 3 ENHANCES MYELINATION
IN DORSAL ROOT - SCHWANN CELL CO-CULTURES

ASCORBIC ACID (50µg/ml) + COMPOUND 3 (100nM)

COMPOUND 2 ENHANCES MYELINATION
IN DORSAL ROOT - SCHWANN CELL CO-CULTURES

CONTROL

COMPOUND 2 ENHANCES MYELINATION
IN DORSAL ROOT - SCHWANN CELL CO-CULTURES

ASCORBIC ACID (50µg/ml)

COMPOUND 2 ENHANCES MYELINATION
IN DORSAL ROOT - SCHWANN CELL CO-CULTURES

ASCORBIC ACID (50µg/ml) + COMPOUND 2 (100nM)

ANGIOGENESIS

10 μg/DAY

ANGIOGENESIS

100 μg/DAY

NAALADASE INHIBITORS USEFUL AS PHARMACEUTICAL COMPOUNDS AND COMPOSITIONS

This application is a continuation-in-part of U.S. patent application Ser. No. 09/110,262, filed Jul. 6, 1998; and U.S. patent application Ser. No. 09/228,391, filed Jan. 12, 1999, which in turn is a continuation-in-part of U.S. patent application Ser. No. 09/110,186, filed Jul. 6, 1998.

BACKGROUND OF THE INVENTION

The present invention relates to N-Acetylated α-Linked Acidic Dipeptidase (NAALADase) inhibitors, pharmaceutical compositions comprising such inhibitors and methods of their use to inhibit NAALADase enzyme activity, thereby effecting neuronal activities, inhibiting angiogenesis, and treating glutamate abnormalities, compulsive disorders, prostate diseases, pain and diabetic neuropathy.

Recent studies have implicated NAALADase in the pathogenesis of glutamate-mediated disorders. Neuropathological studies on post-mortem tissue from patients with amyotrophic lateral sclerosis (ALS) indicate large decreases of N-acetylaspartate (NAA) and N-acetylaspartylglutamate (NAAG) tissue concentrations occurring in association with neuronal degeneration, and increases of NAA and NAAG in cerebral spinal fluid (CSF) from patients with ALS. Concordantly, abnormal NAAG levels and NAALADase activity have also been observed in post-mortem prefrontal and limbic brain tissue of schizophrenic patients. Autopsy studies also suggest a strong correlation between NAAG/NAA and Alzheimer's disease. In post-mortem brain tissue, NAA and NAAG levels were found to be selectively decreased in brain areas (hippocampus and amygdala) affected by Alzheimer's disease pathology.

Glutamate serves as the predominant excitatory neurotransmitter in the central nervous system (CNS). Neurons release glutamate in great quantities when they are deprived of oxygen, as may occur during an ischemic brain insult such as a stroke or a heart attack. This excess release of glutamate in turn causes over-stimulation (excitotoxicity) of N-methyl-D-aspartate (NMDA), AMPA, Kainate and metabotropic glutamate (mGlu) receptors. When glutamate binds to these receptors, ion channels in the receptors open or second messenger systems are stimulated, permitting flows of ions across their cell membranes, e.g., $Ca^{2+}$ and $Na^+$ into the cells and $K^+$ out of the cells. These flows of ions, especially the influx of $Ca^{2+}$, cause over-stimulation of the neurons. The over-stimulated neurons secrete more glutamate, creating a domino-effect which is believed to ultimately result in cell death via the production of proteases, lipases and free radicals.

Excessive activation of glutamate receptors has been implicated in various neurological diseases and conditions, including spinal cord injury, epilepsy, stroke, Alzheimer's disease, Parkinson's disease, Amyotrophic Lateral Sclerosis (ALS), Huntington's disease, diabetic neuropathy, acute and chronic pain, ischemia and neuronal loss following hypoxia, hypoglycemia, ischemia, trauma, and nervous insult.

In particular, glutamatergic abnormalities have been associated with schizophrenia. For example, phencyclidine (PCP) and other antagonists of N-methyl-D-aspartate (NMDA) receptors induce psychotomimetic properties in healthy individuals and exacerbate preexisting symptoms of schizophrenia, suggesting that a depression of glutamate transmission might contribute to schizophrenia. Additionally, it has been reported that antagonists of non-NMDA receptors or pretreatments that attenuate glutamate release reduce mnemonic and other behavioral effects of NMDA receptor antagonists. Studies have also shown that stimulation of certain subtypes of mGlu receptors mediates presynaptic depression and decreases evoke release of glutamate. In 1998, it was reported that an mGlu receptor agonist reduced PCP-induced glutamate efflux in rats, suggesting that the agonist ameliorates the behavioral effects of PCP by attenuating presynaptic glutamatergic activity.

Recent studies have also advanced a glutamatergic basis for compulsive disorders, particularly drug dependence. For example, neurophysiological and pathological effects of ethanol have been found to be mediated through the glutamatergic system. Specifically, acute exposure to ethanol distupts blutamatergic neurotransmission by inhibiting ion flfow through channels in glutamate receptors, whereas chronic exposure up-regulates the number of glutamate receptors and therby increases ion flow. Acute withdrawal from ethanol results in hyperexcitability and seizures in the presence of up-regulated channels, thereby making postsynaptic neurons vulnerable to excitotoxic damage.

Post mortem examinations of histologically normal brains from alcoholics have shown that chronic alcoholism moderately increases the density of the NMDA subtype of glutamate receptors in the frontal cortex. This up-regulation may represent a stage of ethanol-induced chronic neurotoxicity. As such, neurobiological effects of alcoholism, including intoxication, withdrawal seizures, delirioum tremens, Wernicke-Korsakoff syndrome and fetal alcohol syndrome, can be understood as a spectrum of the consequences of ehtanol's effectg on the glutamatergic system. In this regard, alcoholism may be considered another member of the expanding family of glutamate-related neurological disorders.

The glutamatergic system has also been implicated in the behavioral effects of other abused drugs. For example, studies have shown that glutamatergic antagonists block motor-stimulating activities induced by amphetamine and cocaine, and glutamatergic agonists cause the same stereotypy as that produced by amphetamine. These results represent pharmacological evidence that the expression of the stereotypic effect of psychomotor stimulants involves the glutamatergic system.

Epidemiologic studies have revealed a strong correlation between drug dependence and other compulsive disorders. Additionally, a common genetic anomaly has been found among people with alcoholism, cocaine dependence, nicotine dependence, pathological gambling, attention deficit disorder (ADD), Tourette's syndrome, compulsive overeating and obesity. Such disorders are believed to be manifestations of the effects of excitotoxicity.

Based on the above findings, the present inventors tested and found NAALADase inhibitors to be efficacious in the pharmacotherapy of glutamate abnormalities, such as drug dependence, diabetic neuropathy, pain and schizophrenia.

Most research and development activity to date have focused on blocking post-synaptic glutamate receptors with compounds such as NMDA antagonists, glycine antagonists, and other post-synaptic excitatory amino acid (EAA) receptor blockers. Unfortunately, these agents produce severe toxicities even under normal conditions, thus limiting their clinical use. Although not limited to any one particular theory, it is believed that NAALADase inhibitors block glutamate release pre-synaptically without interacting with post-synaptic glutamate receptors. Since NAALADase inhibitors do not appear to alter basal glutamate levels, they may be devoid of the behavioral toxicities asociated with post-synaptic glutamate antagonists.

In addition to glutamate, NAALADase has also been associated with prostate-specific membrane antigen (PSMA). In particular, it has been shown that PSMA cDNA confers NAALADase activity and that NAALADase and PSMA exhibit at least 86% homologous sequence indentity. Carter et al., *Proc. Natl. Acad. Sci.*, Vol. 93, pp. 749–753 (1996). The molecular cloning of PSMA has been reported as a potentioal prostate carcinoma marker and hypothesized to serve as a target for imaging and cytotoxic treatment modalitites for prostate cancer. Additionally, PSMA antibodies, particularly indium-111 labelled and itrium labelled PSMA antibodies, have been described and examined clinically for the diagnosis and treatment of prostate cancer. PSMA is expressed in prostatic ductal epithelium and is present in seminal plasma, prostatic fluid and uring.

The present inventors have found NAALADase inhibitors to be effective in treating prostate diseases, particularly prostate cancer. Although not limited to any particular theory, it is believed that NAALADase inhibitors inhibit PSMA activity. Since mAbs to PSMA have been found to target 23 non-prostate carcinomas (Lui et al., *Science Research*, Vol. 57, pp. 3629–34 (1997)), the present inventors hypothesize that NAALADase inhibitors would also be effective in treating non-prostate cancers, particularly in tissues where NAALADase resides, such as the brain, kidney and testis.

NAALADase has also been found in neovasculature (new blood vessels). The present inventors have discovered that NAALADase inhibitors inhibit or prevent growth of neovasculature (angiogenesis), thereby providing potential therapeutic applications in treating diseases dependent upon angiogenesis. Examples of angiogenesis-dependent diseases include without limitation rheumatoid arthritis, cardiovascular disease, neovascular diseases of the eye, peripheral vascular disorders, and dermatologic ulcers. Angiogenesis is also essential for normal physiological processes, such as growth, fertility and soft tissue wound healing.

Cancer is another disease dependent upon angiogenesis. Cancer tumor cells secrete or release angiogenic substances that activate nearby endothelial cells. These endothelial cells respond by expressing a cell autonomous pattern of behavior that culminates in the formation of new blood vessels. Since research has demonstrated that angiogenesis is necessary to sustain the growth, invasion and metastasis of cancer tumors, the neovasculature inhibiting activity of NAALADase inhibitors further supports their utility in treating all types of cancers.

Until a few years ago, only a few NAALADase inhibitors had been identified and they were used in non-clinical research. Examples of these compounds include general metallopeptidase inhibitors such as o-phenanthroline, metal chelators such as EGTA and EDTA, and peptide analogs such as quisqualic acid and β-NAAG. These compounds either have toxic side effects or are incapable of being administered in pharmaceutically effective amounts. In view of the broad range of potential applications, there is a need for new NAALADase inhibitors, pharmaceutical compositions comprising such inhibitors, and methods of their use.

SUMMARY OF THE INVENTION

The present invention relates to N-Acetylated α-Linked Acidic Dipeptidase (NAALADase) enzyme inhibitors and compositions useful for effecting neuronal activities, inhibiting angiogenesis, and treating glutamate abnormalities, compulsive disorders, prostate diseases, pain and diabetic neuropathy.

More specifically, the present invention relates to a compound of formula I

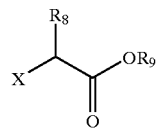

I or a pharmaceutically acceptable equivalent, wherein:
X is a moiety of formula II, III or IV

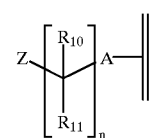

II

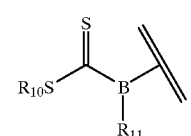

III

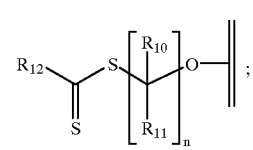

IV m and n are independently 0, 1, 2, 3 or 4;
Z is $SR_{13}$, $SO_3R_{13}$, $SO_2R_{13}$, $SOR_{13}$, $SO(NR_{13})$ $R_{14}$ or $S(NR_{13}R_{14})_2R_{15}$;
B is N or $CR_{16}$;
A is O, S, $CR_{17}R_{18}$ or $(CR_{17}R_{18})_mS$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$, cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s);
provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

Additionally, the present invention relates to a compound containing both sulfur and an acid group which is effective in treating stroke in a mammal when administered more than 60 minutes following onset of stroke.

The present invention also relates to a method for inhibiting NAALADase enzyme activity in a mammal, comprising administering to said mammal an effective amount of a compound of formula I.

The present invention further relates to a method for treating a glutamate abnormality in a mammal, comprising administering to said mammal an effective amount of a compound of formula I.

Additionally, the present invention relates to a method for treating a glutamate abnormality selected from the group consisting of compulsive disorder, stroke, demyelinating disease, schizophrenia, Parkinson's disease and ALS in a mammal, comprising administering to said mammal an effective amount of a compound of formula I.

The present invention also relates to a method for effecting a neuronal activity in a mammal, comprising administering to said mammal an effective amount of a compound of formula I.

The present invention further relates to a method for treating a prostate disease in a mammal, comprising administering to said mammal an effective amount of a compound of formula I.

Additionally, the present invention relates to a method for treating cancer in a mammal, comprising administering to said mammal an effective amount of a compound of formula I.

The present invention also relates to a method for treating stroke in a mammal, comprising administering an effective amount of a compound containing both sulfur and an acid group to said mammal more than 60 minutes following onset of stroke.

The present invention further relates to a method for treating stroke in a mammal, comprising administering an effective amount of a compound containing both sulfur and an acid group to said mammal more than 60 minutes following onset of stroke.

Additionally, the present invention relates to a method for inhibiting angiogenesis in a mammal comprising administering to said mammal an effective amount of a NAALADase inhibitor.

The present invention also relates to a method for treating pain in a mammal comprising administering to said mammal an effective amount of a NAALADase inhibitor.

The present invention further relates to a method for treating diabetic neuropathy in a mammal comprising administering to said mammal an effective amount of a NAALADase inhibitor.

Additionally, the present invention relates to method for preparing a compound containing both sulfur and an acid group, comprising the step of reacting a thiolactone with a substituted ester to form a compound of formula VI

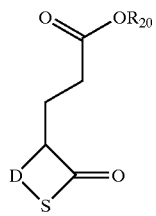

VI wherein:

D is $(CR_{21}R_{22})$;

n is 0, 1, 2, 3 or 4; and $R_{20}$, $R_{21}$ and $R_{22}$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s).

The present invention also relates to a method for preparing a compound containing both sulfur and an acid group comprising the steps of:

(i) reacting Meldrum's acid with a sulfur containing reactant to form a Meldrum's acid sulfur containing derivative; and (ii) reacting the Meldrum's acid sulfur containing derivative with an ester to form a compound of formula VII

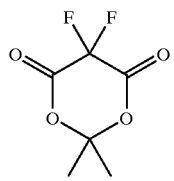

VII wherein:

E is a sulfur containing moiety; and

F is a propionic acid ester c ontaining moiety.

Finally, the present invention relates to a pharmaceutical composition comprising:

(i) an effective amount of a compound of formula I; and (ii) a pharmaceutically acceptable carrier.

DETAILED DESCRIPTION OF THE INVENTION

Definitions

Figure 1A:
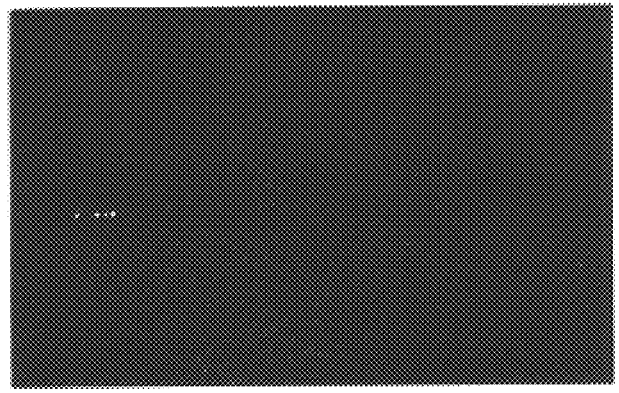
FIG. 1A is a microphotograph of an immunostained dorsal root ganglia-Schwann cell co-culture.
Figure 1B:
FIG. 1B is a microphotograph of an immunostained dorsal root ganglia-Schwann cell co-culture following treatment with ascorbic acid.
Figure 1C:
FIG. 1C is a microphotograph of an immunostained dorsal root ganglia-Schwann cell co-culture following treatment with ascorbic acid and Compound 3.
Figure 2A:
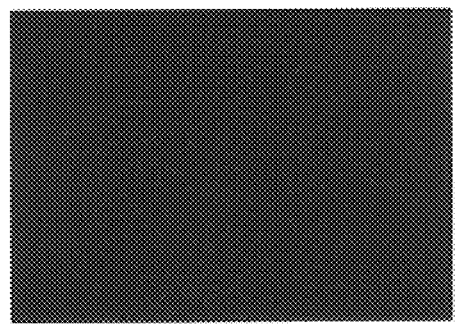
FIG. 2A is a microphotograph of an immunostained dorsal root ganglia-Schwann cell co-culture.
Figure 2B:
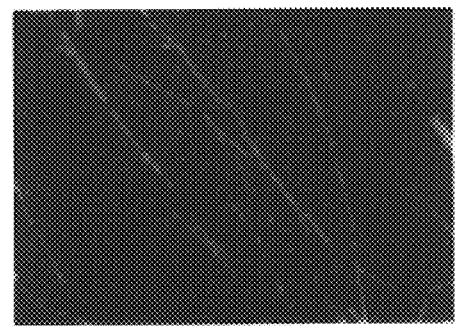
FIG. 2B is a microphotograph of an immunostained dorsal root ganglia-Schwann cell co-culture following treatment with ascorbic acid.
Figure 2C:
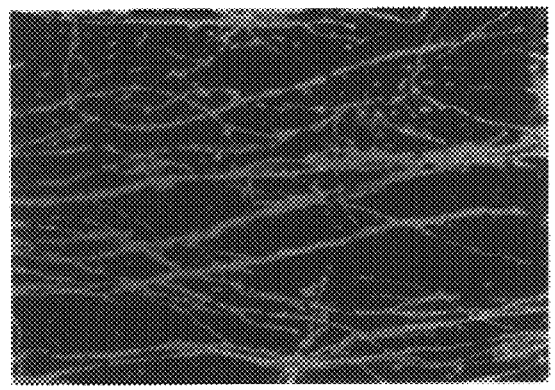
FIG. 2C is a microphotograph of an immunostained dorsal root ganglia-Schwann cell co-culture following treatment with ascorbic acid and Compound 2.

"Acid group" includes without limitation —COOH, —$SO_3H$, —$SO_2HNH$, —$PO_2H_2$, —CN, —$PO_3H_2$, —SH, —NHCOH, —$NH_2$, —$CONH_2$, —CONHOH, —$CONHNSO_2H$, —$COHNSO_2H$, and —CONHCN.

"Compound 1" refers to pure and impure forms of 2-(2-sulfanylethyl)pentanedioic acid, or the compound prepared by Example 10.

"Compound 2" refers to 2-[[(2,3,4,5,6-pentafluorobenzyl) hydroxyphosphinyl]methyl]-pentanedioic acid.

"Compound 3" refers to 2-(phosphonomethyl)-pentanedioic acid (PMPA).

"Effective amount" refers to the amount required to produce the desired effect. "Therapeutically effective amount" refers to the amount required to inhibit NAALA-Dase enzyme activity, effect neuronal activity, inhibit angiogenesis, and/or treat glutamate abnormality, compulsive disorder, prostate disease, pain and/or diabetic neuropathy.

"IP" or "i.p." refers to intraperitoneal.

"Isosteres" refer to elements, molecules or ions having similar or identical physical properties. Typically, two isosteric molecules have similar or identical volumes and shapes. Ideally, isosteric compounds should be isomorphic and able to co-crystallize. Among the other physical properties that isosteric compounds usually share are boiling point, density, viscosity and thermal conductivity. However, certain properties are usually different: dipolar moments, polarity, polarization, size and shape since the external orbitals may be hybridized differently. The term "isosteres" encompass "bioisosteres".

"Bioisosteres" are isosteres which, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acylcyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus- derived acidic functions such as phosphinates, phosphonates, phosphonamides, sulphonates, sulphonamides, and acylsulphonamides.

"Derivative" refers to a substance produced from another substance either directly or by modification or partial substitution.

"Meldrum's acid" refers to 2,2-dimethyl-1,3-dioxane-4, 6-dione.

"Metabolite" refers to a substance produced by metabolism or by a metabolic process.

"Pharmaceutically acceptable equivalent" includes without limitation pharmaceutically acceptable salts, hydrates, metabolites, prodrugs and carboxylic isosteres. Many pharmaceutically acceptable equivalents are expected to have the same or similar in vitro or in vivo activity as the compounds of formulas I–V.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocya-nate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Also, the basic nitrogen-containing groups can be quarternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995), or methods readily apparent to one skilled in the art. For example, the inventive compounds can be transformed into prodrugs by converting one or more of the hydroxy or carboxy groups into esters.

"Radiosensitizer" refers to a low molecular weight compound administered to animals in therapeutically effective amounts to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention.

"Alkyl" refers to a branched or unbranched saturated hydrocarbon chain comprising a designated number of carbon atoms. For example, a $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, a $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 6 carbon atoms.

"Halo" or "halogen" refers to fluoro, chloro, bromo and iodo.

"Isomers" refer to compounds having the same number and kind of atoms, and hence the same molecular weight, but differing in respect to the arrangement or configuration of the atoms.

"Stereoisomers" refer to compounds which have identical chemical constitution, but differ as regards to the arrangement of the atoms or groups in space.

"Optical isomers" refer to either of two kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$ optical isomers, where n is the number of asymmetric carbon atoms.

"Enantiomers" refer to stereolsomers which are non-superimposable mirror images of one another.

"Enantiomer-enriched" refers to a mixture in which one enantiomer predominates.

"Racemic" refers to a mixture containing equal parts of individual enantiomers.

"Non-racemic" refers to a mixture containing unequal parts of individual enantiomers.

"Animal" refers to a living organism having sensation and the power of voluntary movement and requirement for its existence oxygen and organic food. Examples include without limitation a mammal such as a member of the human, equine, porcine, bovine, murine, canine or feline species. In the case of a human, the term "animal" may also be referred to as a "patient".

"Disease" refers to any deviation from or interruption of the normal structure or function of any part, organ, or system (or combination thereof) of the body that is manifested by a characteristic set of symptoms and signs and whose etiology, pathology, and prognosis may be known or unknown. *Dorland's Illustrated Medical Dictionary*, (W.B. Saunders Co. 27th ed. 1988).

"Disorder" refers to any derangement or abnormality of function; a morbid physical or mental state. *Dorland's Illustrated Medical Dictionary*, (W.B. Saunders Co. 27th ed. 1988).

"Glutamate abnormality" refers to any disease, disorder or condition in which glutamate is implicated, including pathological conditions involving elevated levels of glutamate. Examples of glutamate abnormalities include without limitation spinal cord injury, epilepsy, stroke, Alzheimer's disease, Parkinson's disease, Amyotrophic Lateral Sclerosis (ALS), Huntington's disease, schizophrenia, acute pain, chronic pain, ischemia, neuronal insult and compulsive disorders.

"Ischemia" refers to localized tissue anemia due to obstruction of the inflow of arterial blood. Global ischemia occurs when blood flow to the entire brain ceases for a period of time, such as may result from cardiac arrest. Focal ischemia occurs when a portion of the brain is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Nervous function" refers to the various functions of the nervous system, which among other things provide an awareness of the internal and external environments of the body, make possible voluntary and reflex activities between the various structural elements of the organism, and balance the organism's response to environmental changes.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination process, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuroprotective" refers to the effect of reducing, arresting or ameliorating nervous insult, and protecting, resuscitating or reviving nervous tissue which has suffered nervous insult.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*, (W.B. Saunders Co. 27th ed. 1988). Examples of pain include without limitation acute, chronic, cancer, burn, incisional, inflammatory, diabetic neuropathic and back pain.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Compulsive disorder" refers to any disorder characterized by irresistible impulsive behavior. Examples of compulsive disorders include without limitation drug dependence, eating disorders, pathological gambling, ADD and Tourette's syndrome.

"Attention Deficit Disorder" refers to a disorder characterized by developmentally inappropriate inattention and impulsivity, with or without hyperactivity. Inattention means a failure to finish tasks started, easy distractibility, seeming lack of attention, and difficulty concentrating on tasks requiring sustained attention. Impulsivity means acting before thinking, difficulty taking turns, problems organizing work, and constant shifting from one activity to another. Hyperactivity means difficulty staying seated and sitting still, and running or climbing excessively.

"Drug dependence" refers to a psychologic addiction or a physical tolerance to a drug. Tolerance means a need to increase the dose progressively in order to produce the effect originally achieved by smaller amounts.

"Withdrawal syndrome" refers to a disorder characterized by untoward physical changes that occur when the drug is discontinued or when its effect is counteracted by a specific antagonist.

"Eating disorder" refers to compulsive overeating, obesity or severe obesity. obesity means body weight of 20% over standard height-weight tables. Severe obesity means over 100% overweight.

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Schizophrenia" refers to a mental disorder or group mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include without limitation acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary*, (W.B. Saunders Co. 27th ed. 1988).

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Angiogenesis" refers to the process whereby new capillaries are formed.

"Angiogenesis-dependent disease" includes without limitation cancer, rheumatoid arthritis, cardiovascular disease, neovascular diseases of the eye, peripheral vascular disorders, and dermatologic ulcers.

"Inhibition" of angiogenesis may be measured by many parameters in accordance with the present invention and, for instance, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention.

In relation to angiogenesis or angiogenic growth, "prevention" refers to no substantial angiogenesis or angiogenic growth if none had previously occurred, or no substantial further angiogenesis or angiogenic growth if growth had previously occurred.

"Cancer" includes without limitation ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Metastasis" refers to "[t]he ability of cells of a cancer to disseminate and form new foci of growth at noncontiguous sites (i.e., to form metastases)." See Hill, R.P, Chapter 11, "Metastasis", pp. 178–195 in *The Basic Science of Oncology*, Tannock et al., Eds., McGraw-Hill, New York (1992), herein incorporated by reference. "The transition from in situ tumor growth to metastatic disease is defined by the ability of tumor cells of the primary site to invade local tissues and to cross tissue barriers . . . To initiate the metastatic process, carcinoma cells must first penetrate the epithelial basement membrane and then invade the interstitial stroma . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* 71: 1368–1383 (1993), herein incorporated by reference.

"Electromagnetic radiation" includes without limitation radiation having the wavelength of $10^{-20}$ to $10^{0}$ meters. Preferred embodiments of the present invention employ the electromagnetic radiation of gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

"Prostate disease" refers to any disease affecting the prostate. Examples of prostate disease include without limitation prostate cancer such as adenocarcinoma and metastatic cancers of the prostate; and conditions characterized by abnormal growth of prostatic epithelial cells such as benign prostatic hyperplasia.

"Treating" refers to administering a compound or composition according to the present invention so as to:

(i) prevent a disease, disorder or condition from occurring in an animal which may be predisposed to the disease, disorder and/or condition but has not yet been diagnosed as having it;

(ii) inhibit the disease, disorder or condition, i.e., arresting its development; and/or (iii) relieve the disease, disorder or condition, i.e., causing regression of the disease, disorder and/or condition.

In relation to drug dependence, "treating" includes administering a compound or composition of the present invention to suppress the psychologic addiction or physical tolerance to the drug of abuse, and/or relieve and/or prevent a withdrawal syndrome resulting from the drug dependence.

In relation to stroke, "therapeutic window of opportunity" or "window" refers to the maximal delay between the onset of ischemia and the initiation of efficacious therapy.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate ("NAA") and glutamate ("GLU"):

Catabolism of NAAG by NAALADase

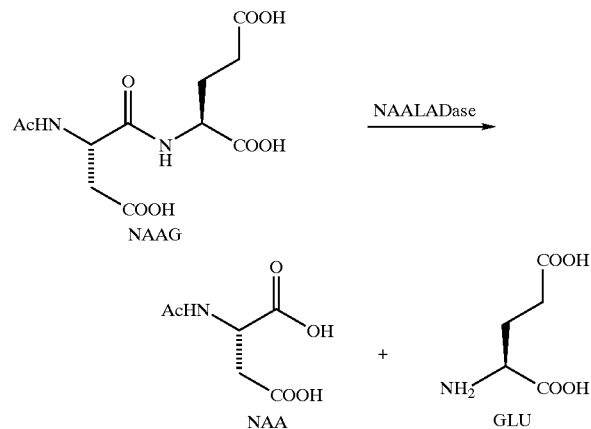

Based upon amino acid sequence homology, NAALADase has been assigned to the M28 peptidase family. NAALADase is also called prostate-specific membrane antigen (PSMA) or human glutamate carboxypeptidase II (GCP II), EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG's synaptic action. Alternatively, if NAAG functions as a precursor for glutamate, the primary function of NAALADase may be to regulate synaptic glutamate availability.

"NAALADase inhibitor" refers to any compound which inhibits NAALADase enzyme activity.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, "$K_i$" as used herein refers to the affinity between the inventive compounds and NAALADase. "$IC_{50}$" is a related term used to define the concentration or amount of a compound which is required to cause a 50% inhibition of the target enzyme.

COMPOUNDS OF THE PRESENT INVENTION

The present invention relates to a compound of formula I

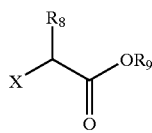

I or a pharmaceutically acceptable equivalent, wherein:

X is a moiety of formula II, III or IV

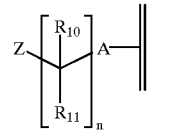

II

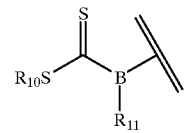

III

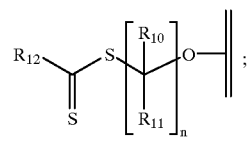

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

Possible substituents of said alkenyl, cycloalkyl, cycloalkenyl, and $Ar_1$ include, without limitation, $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Preferably, X is a moiety of formula II; n is 0, 1, 2 or 3; Z is SH, $SO_3H$, $SO_2H$, SOH or $S(NRHR_{14})_2R_{15}$; and A is O, S or $CR_{17}R_{18}$.

More preferably, Z is SH.

Most preferably, when Z is SH, then $R_8$ is —$(CH_2)_2$COOH.

In another preferred embodiment, when X is a moiety of formula II, $R_8$ is —$(CH_2)_2COOR_{19}$ or —$(CH_2)_2CONHR_{19}$, A is $CH_2$, n is 0, Z is $SR_{13}$, then $R_{13}$ is not hydrogen or $COR_{19}$; and when X is a moiety of formula III, B is N, and $R_8$ is —$(CH_2)_2COOH$, then $R_{11}$ is not hydrogen.

Preferred compounds of formula I are selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;

2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

The most preferred compounds of formula I are selected from the group consisting of 2-(2-sulfanylethyl)pentanedioic acid, 2-(2-sulfanylpropyl)-pentanedioic acid, 2-(3-sulfanylpropyl)pentanedioic acid and pharmaceutically acceptable equivalents. Ideally, the compounds of formula I is are enantiomers or enantiomer-enriched mixtures.

Representative compounds of formula I wherein X is a moiety of formula III, $R_8$ is —$(CH_2)_2COOH$, $R_9$ is hydrogen, and B is $CR_{16}$, include without limitation:
2-(dithiocarboxymethyl)pentanedioic acid;
2-(1-dithiocarboxyethyl)pentanedioic acid; and
pharmaceutically acceptable equivalents.

Representative compounds of formula I wherein X is a moiety of formula III, $R_8$ is —$(CH_2)_2COOH$, $R_9$ is hydrogen, and B is N, include without limitation:
2-dithiocarboxyaminopentanedioic acid;
2-[(N-methyldithiocarboxy) amino] pentanedioic acid; and
pharmaceutically acceptable equivalents.

Representative compounds of formula I wherein X is a moiety of formula IV include without limitation:
2-benzyl-4-sulfanylbutanoic acid;
2-benzyl-4-sulfanylpentanoic acid;
2-(3-pyridylmethyl)-4-sulfanylpentanoic acid;
2-(3-pyridylmethyl)-4-sulfanyihexanoic acid;
2-benzyl-3-sulfanylpropanoic acid;
2-benzyl-3-sulfanylpentanoic acid;
2-(4-pyridylmethyl)-3-sulfanylpentanoic acid; and
pharmaceutically acceptable equivalents.

The structures of some representative compounds of formula I are set forth below.

| Structure | Name |
|---|---|
| 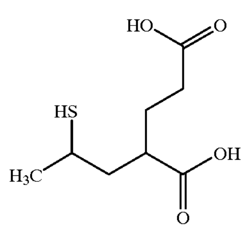 | 2-(2-sulfanylpropyl) pentanedioic acid |
| 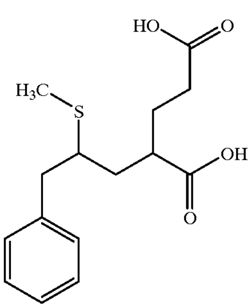 | 2-[2-(methylsulfanyl)-3-phenylpropyl]pentanedioic acid |
| 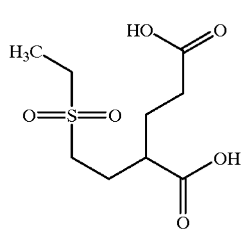 | 2-[2-(ethylsulfonyl)ethyl]pentanedioic acid |

-continued

| Structure | Name |
|---|---|
| 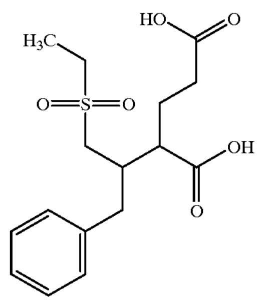 | 2-[1-benzyl-2-(ethylsulfonyl)ethyl]pentanedioic acid |
| 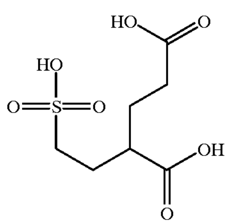 | 2-(2-sulfoethyl)pentanedioic acid |
| 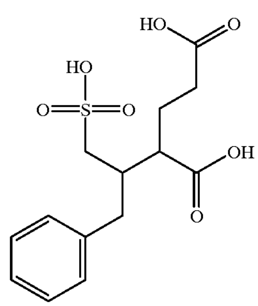 | 2-(1-benzyl-2-sulfoethyl)pentanedioic acid |
| 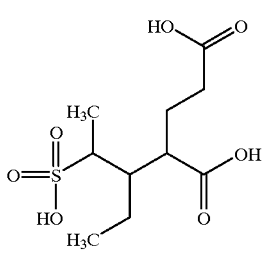 | 2-(1-ethyl-2-sulfopropyl)pentanedioic acid |
| 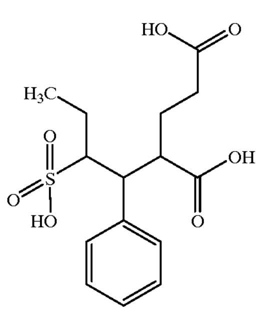 | 2-(1-phenyl-2-sulfobutyl)pentanedioic acid |

-continued

| Structure | Name |
|---|---|
| 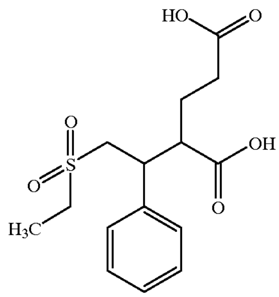 | 2-[2-(ethylsulfonyl)-1-phenylethyl]pentanedioic acid |
| 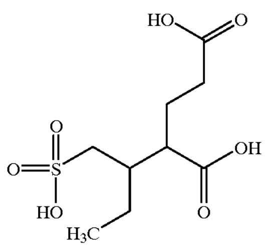 | 2-[1-(sulfomethyl)propyl]pentanedioic acid |
| 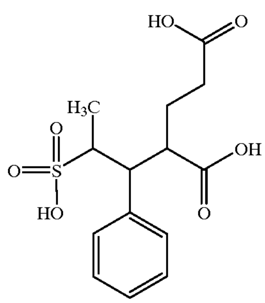 | 2-(1-phenyl-2-sulfopropyl)pentanedioic acid |
| 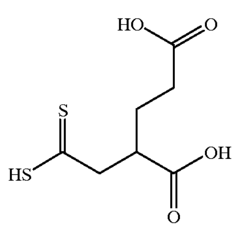 | 2-(dithiocarboxymethyl)pentanedioic acid |
| 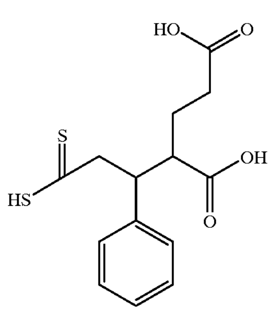 | 2-(2-dithiocarboxy-1-phenylethyl)pentanedioic acid |

-continued

| Structure | Name |
|---|---|
| 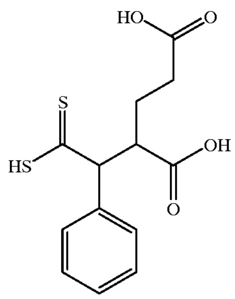 | 2-[dithiocarboxy(phenyl)methyl]pentanedioic acid |
| 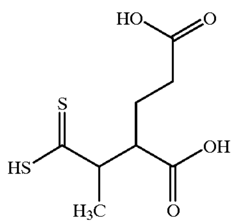 | 2-(1-dithiocarboxyethyl)pentanedioic acid |
| 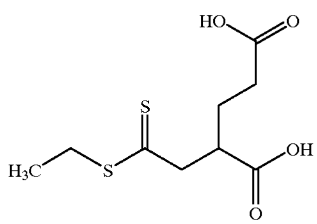 | 2-{[ethylthio(thiocarbonyl)]methyl}pentanedioic acid |
| 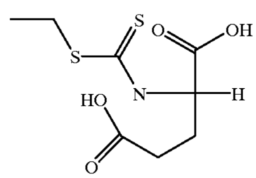 | 2-[(ethylsulfanylthiocarbonyl)amino]pentanedioic acid |
| 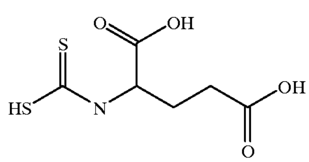 | 2-[(dithiocarboxy)amino]pentanedioic acid |
| 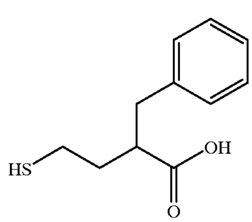 | 2-benzyl-4-sulfanyl butanoic acid |
| 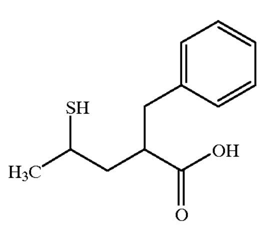 | 2-benzyl-4-sulfanylpentanoic acid |

-continued

| Structure | Name |
|---|---|
| 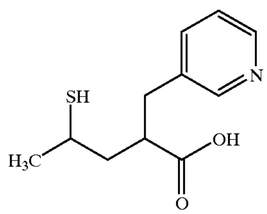 | 2-(3-pyridylmethyl)-4-sulfanylpentanoic acid |
| 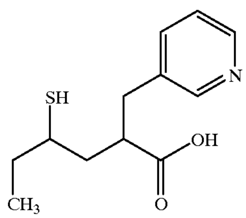 | 2-(3-pyridylmethyl)-4-sulfanylhexanoic acid |
| 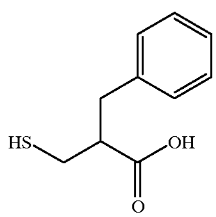 | 2-benzyl-3-sulfanylpropanoic acid |
| 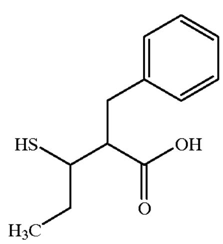 | 2-benzyl-3-sulfanylpentanoic acid |
| 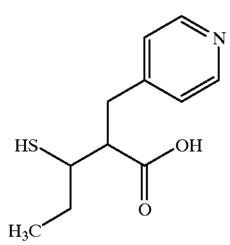 | 2-(4-pyridylmethyl)-3-sulfanylpentanoic acid |
| 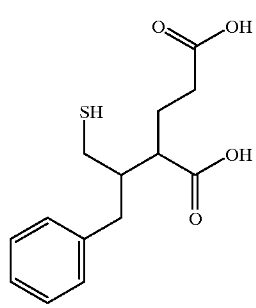 | 2-(1-benzyl-2-sulfanylethyl)pentanedioic acid |

-continued

| Structure | Name |
|---|---|
| 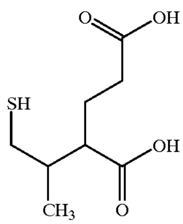 | 2-(1-methyl-2-sulfanylethyl)pentanedioic acid |
| 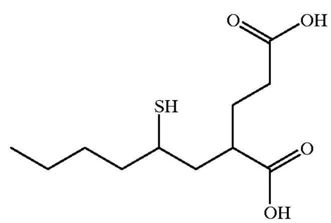 | 2-(2-sulfanylhexyl)pentanedioic acid |
| 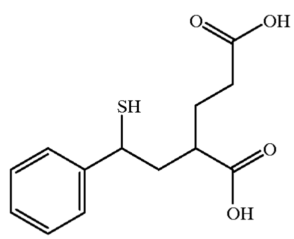 | 2-(2-phenyl-2-sulfanylethyl)pentanedioic acid |
| 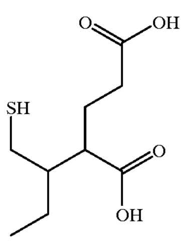 | 2-(1-ethyl-2-sulfanylethyl)pentanedioic acid |
| 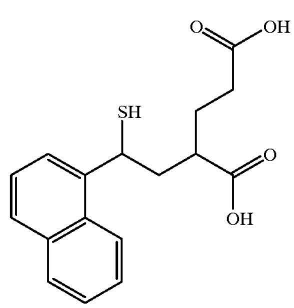 | 2-(2-naphthyl-2-sulfanylethyl)pentanedioic acid |
| 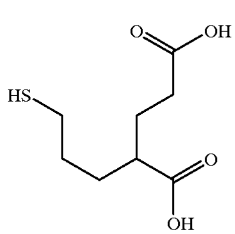 | 2-(3-sulfanylpropyl)pentanedioic acid |

| Structure | Name |
|---|---|
| 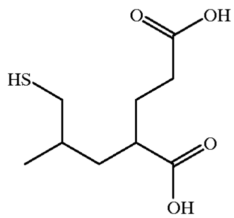 | 2-(3-sulfanyl-2-methylpropyl)pentanedioic acid |
| 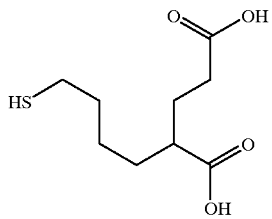 | 2-(4-sulfanylbutyl)pentanedioic acid |
| 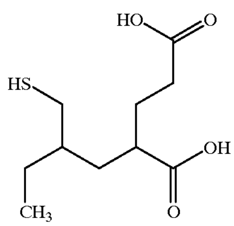 | 2-[2-(sulfanylmethyl)butyl]pentanedioic acid |
| 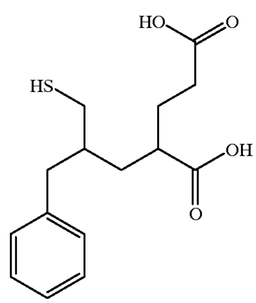 | 2-[3-sulfanyl-2-(phenylmethyl)propyl]pentanedioic acid |
| 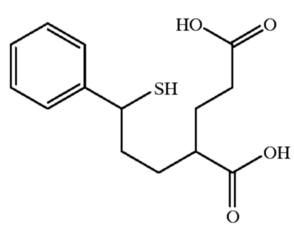 | 2-(3-sulfanyl-3-phenylpropyl)pentanedioic acid |
| 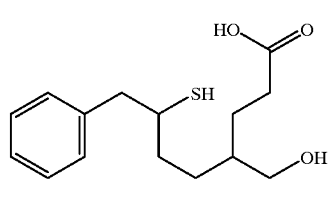 | 2-(3-sulfanyl-4-phenylbutyl)pentanedioic acid |

-continued
| Structure | Name |
|---|---|
| 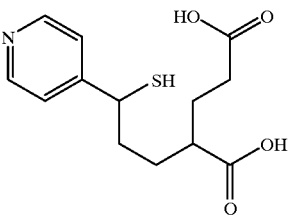 | 2-[3-sulfanyl-4-(4-pyridinyl)butyl]pentanedioic acid |
| 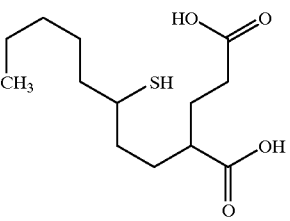 | 2-(3-sulfanyloctyl)pentanedioic acid |
| 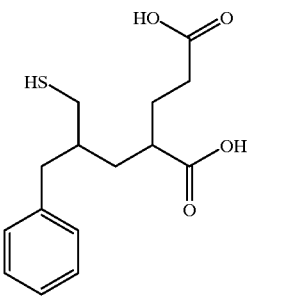 | 2-[3-sulfanyl-2-(phenylmethyl)propyl]pentanedioic acid |
| 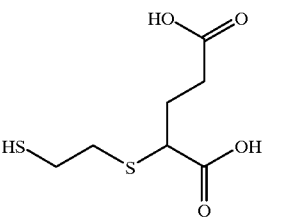 | 2-[(2-sulfanylethyl)thio]pentanedioic acid |
| 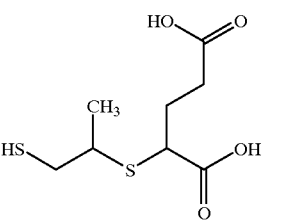 | 2-[(2-sulfanyl-1-methylethyl)thio]pentanedioic acid |
| 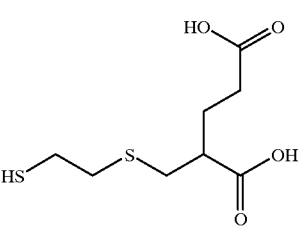 | 2-[[(2-sulfanylethyl)thio]methyl]pentanedioic acid |

-continued

| Structure | Name |
|---|---|
| 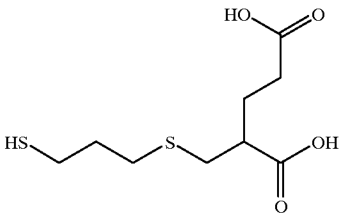 | 2-[[(3-sulfanylpropyl)thio]methyl]pentanedioic acid |
| 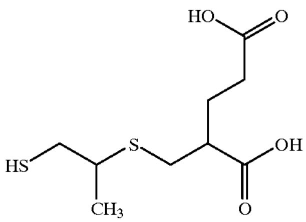 | 2-[[(2-sulfanyl-1-methylethyl)thio]methyl]pentanedioic acid |
| 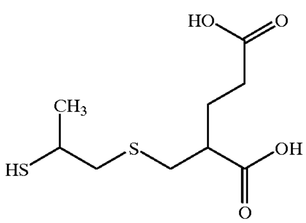 | 2-[[(2-sulfanylpropyl)thio]methyl]pentanedioic acid |
| 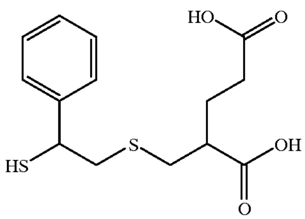 | 2-[[(2-sulfanyl-2-phenylethyl)thio]methyl]pentanedioic acid |
| 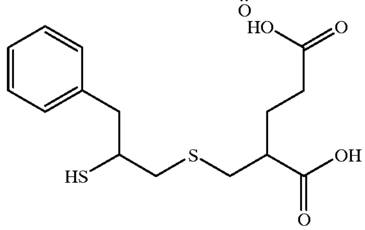 | 2-[[(2-sulfanyl-3-phenylpropyl)thio]methyl]pentanedioic acid |
| 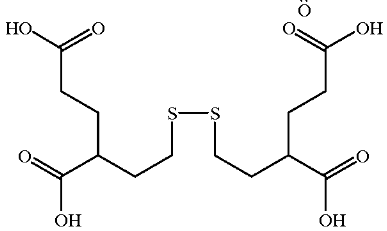 | 2-[2-[(3,5-dicarboxypentyl)dithio]ethyl]pentanedioic acid |

Some compounds of the present invention possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds of the present invention can likewise be obtained by utilizing optically active starting materials.

It is understood that the inventive compounds encompass optical isomers as well as racemic and non-racemic mixtures.

As discussed in greater detail below, the inventive compounds possess various pharmacological and pharmaceutical properties. In particular, the inventive compounds inhibit NAALADase enzyme activity. It is postulated that by inhibiting NAALADase enzyme activity, the inventive compounds regulate presynaptic release of glutamate which occurs during neurodegeneration.

The inventive compounds also protect against neurodegeneration in in vitro as well as in vivo animal models. Several inventive compounds have been demonstrated to be neuroprotective in tissue culture models of ischemia, when administered both pre- and post-ischemia. Some of the inventive compounds provide significant neuroprotective effects when administered up to 60 minutes following ischemic damage in the in vitro model.

Moreover, some of the inventive compounds have been shown to afford significant protection in in vivo rat MCAO stroke model, and to be protective when administered at 60, 120, 180 and 360 minutes post-ischemia. In such cases, the inventive compounds are effective for treating stroke in an animal when administered more than 60 minutes, more than 120 minutes, more than 180 minutes, and more than 360 minutes following the onset of stroke. One of ordinary skill in the art would expect such compounds to be equally, if not more, effective when administered within 60 minutes following onset of stroke. Likewise, compounds which are effective for treating stroke when administered more than 360 minutes following onset of stroke would be expected to embody compounds which are effective when administered at anytime prior to 360 minutes following onset of stroke. In addition to providing neuroprotection, it is possible that the inventive compounds are effective for treating stroke by providing behavioral functional recovery after stroke.

Thus, the present invention further relates to a compound containing both sulfur and an acid group which is effective in treating stroke in a mammal when administered more than 60 minutes following onset of stroke.

Preferably, the compound is effective in treating stroke in a mammal when administered more than 120 minutes following onset of stroke. More preferably, the compound is effective in treating stroke in a mammal when administered more than 180 minutes following onset of stroke. Most preferably, the compound is effective in treating stroke in a mammal when administered more than 360 minutes following onset of stroke.

PHARMACEUTICAL COMPOSITIONS OF THE PRESENT INVENTION

The present invention also relates to a pharmaceutical composition comprising:

(i) an effective amount of a compound of formula I; and (ii) a pharmaceutically acceptable carrier.

Preferably, the compound of formula I is present in an effective amount for inhibiting NAALADase enzyme activity, treating a glutamate abnormality, effecting a neuronal activity, treating a compulsive disorder, treating a prostate disease, or inhibiting angiogenesis in a mammal.

Preferred compounds of formula I are set forth above.

METHODS OF THE PRESENT INVENTION

METHOD FOR INHIBITING NAALADASE ENZYME ACTIVITY

The present invention further relates to a method for inhibiting NAALADase enzyme activity in a mammal, comprising administering to said mammal an effective amount of a compound of formula I.

METHOD FOR TREATING GLUTAMATE ABNORMALITY

The present invention further relates to a method for treating a glutamate abnormality in a mammal, comprising administering to said mammal an effective amount of a compound of formula I.

The glutamate abnormality may be any disease, disorder or condition in which glutamate is implicated, including pathological conditions involving elevated levels of glutamate. Examples of glutamate abnormalities include without limitation epilepsy, stroke, Alzheimer's disease, Parkinson's disease, Amyotrophic Lateral Sclerosis (ALS), Huntington's disease, schizophrenia, acute pain, chronic pain, ischemia, peripheral neuropathy (including diabetic neuropathy), traumatic brain injury and physical damage to the spinal cord. In a preferred embodiment, the glutamate abnormality is selected from the group consisting of ischemia, stroke, Parkinson's disease, Amyotrophic Lateral Sclerosis (ALS) and spinal cord injury.

Although not limited to any one particular theory, it is believed that the compounds of formula I modulate levels of glutamate by acting on a storage form of glutamate which is hypothesized to be upstream from the effects mediated by the NMDA receptor.

The free radical scavenging properties of the thiol functional group may also contribute to the compounds' therapeutic efficacy. Free radical scavengers have been implicated in various types of acute and chronic pathologic conditions in the brain and neural tissue. Recent studies show that free radical scavengers exhibit neuroprotective effects in cerebral ischemia-reperfusion, excitotoxic amino acid brain injury, mitochondrial dysfunction, diabetes, diabetic neuropathy, inborn errors of metabolism, and other causes of acute or chronic damage to the brain or neural tissue. Krishan et al., *Pharmacological Research*, Vol. 37, No. 1, pp. 23–9 (January 1998); Noda et al., *Research Communications in Molecular Pathology and Pharmacology*, Vol. 96, No. 2, pp. 125–36 (May 1997); Anderson et al., *Canadian Journal of Cardiology*, Vol. 12, No. 10, pp. 1099–104 (October 1996); Mizuno et al., *General Pharmacology*, Vol. 30, No. 4, pp. 575–8 (April 1998); de la Torre et al., *Brain Research*, Vol. 779, Nos. 1–2, pp. 285–8 (January 1998); Yuki et al., *Molecular and Chemical Neuropathology*, Vol. 32, Nos. 1–3, pp. 123–8 (September–December 1997); Yamamoto et al., *Brain Research*, Vol. 762, Nos. 1–2, pp. 240–2 (July 11, 1997). Accordingly, the inventive compounds could be particularly effective in treating brain disorders involving free radical injury.

METHOD FOR TREATING COMPULSIVE DISORDER

The present invention further relates to a method for treating a compulsive disorder, comprising administering to a patient in need of such treatment an effective amount of a compound of formula I.

The compulsive disorder may be any disorder characterized by irresistible impulsive behavior. Examples of compulsive disorders treatable by the methods of the present invention include drug dependence, eating disorders, pathological gambling, ADD and Tourette's syndrome.

Preferably, the compulsive disorder is drug dependence. Commonly used drugs with potential for dependence include CNS depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

More preferably, the drug dependence is alcohol, nicotine, heroin or cocaine dependence.

METHOD FOR EFFECTING NEURONAL ACTIVITY

The inventors have also discovered that inhibition of NAALADase promotes nerve regeneration and myelin formation.

Accordingly, the present invention further relates to a method for effecting a neuronal activity in a mammal, comprising administering an effective amount of the compound of formula I to said mammal.

The neuronal activity that is effected by the inventive method may be selected from the group consisting of: stimulation of damaged neurons, promotion of neuronal regeneration, prevention of neurodegeneration and treatment of a neurological disorder.

Examples of neurological disorders that are treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barrésyndrome; Alzheimer's disease; and Parkinson's disease.

The inventive method is particularly useful for treating a neurological disorder selected from the group consisting of: peripheral neuropathy caused by physical injury or disease state, traumatic brain injury, physical damage to the spinal cord, stroke associated with brain damage, demyelinating diseases and neurological disorders relating to neurodegeneration. Examples of demyelinating diseases include multiple sclerosis and peripheral demyelinating disease such as peripheral neuropathies and Charcot-Marie Tooth disease. Examples of neurological disorders relating to neurodegeneration include Alzheimer's disease, Parkinson's disease, and amyotrophic lateral sclerosis (ALS).

METHOD FOR TREATING PROSTATE DISEASE

The present invention further relates to a method for treating a prostate disease in a mammal, comprising administering to said mammal an effective amount of a compound of formula I.

In a preferred embodiment, prostate disease is prostate cancer such as adenocarcinoma and metastatic cancers of the prostate, or a condition characterized by abnormal growth of prostatic epithelial cells such as benign prostatic hyperplasia.

METHOD FOR TREATING CANCER

In addition to prostate cancer, other forms of cancer that may be treated with the compounds of the present invention include without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in treating cancer of tissues where NAALADase enzymes reside. Such tissues include the prostate as well as the brain, kidney and testis.

METHOD FOR TREATING STROKE

The present invention further relates to a method for treating stroke in a mammal, comprising administering an effective amount of a compound containing both sulfur and an acid group to said mammal more than 60 minutes following onset of stroke.

Preferably, the compound is administered to said mammal more than 180 minutes following onset of stroke.

More preferably, the compound is administered to said mammal more than 360 minutes following onset of stroke.

Examples of a compound containing both sulfur and an acid group include without limitation compounds of formula I.

METHOD FOR INHIBITING ANGIOGENESIS

The present inventors have unexpectedly found that NAALADase inhibitors can affect angiogenesis in tissues containing NAALADase. Previous research showed that NAALADase is enriched in synaptic plasma membranes and is primarily localized to neural and kidney tissue. NAALADase has also been found in the tissues of the prostate and testes. Additionally, previous findings have shown NAALADase to be present in neovasculature. Furthermore, as NAALADase continues to be discovered in other tissues of the body, NAALADase inhibitors most likely will also show efficacy in the inhibition of angiogenesis in those tissues.

Accordingly, the present invention further relates to a method for inhibiting angiogenesis in a mammal comprising administering to said mammal an effective amount of a NAALADase inhibitor.

Angiogenesis may be necessary for fertility or metastasis of cancer tumors, or may be related to an angiogenic-dependent disease. Thus, the angiogenic-dependent diseases treatable by the inventive methods include without limitation rheumatoid arthritis, cardiovascular diseases, neovascular diseases of the eye, peripheral vascular disorders, and cancerous tumor growth, invasion, and metastasis.

The inventive methods are particularly useful for inhibiting angiogenesis in cancerous tumors of tissues where NAALADase enzymes reside. Such tissues include, but are not limited to, the brain, kidney, prostate, testis, and blood vessels.

METHOD FOR TREATING PAIN

The present invention further relates to a method for treating pain in a mammal comprising administering to said mammal an effective amount of a NAALADase inhibitor.

NAALADase inhibitors are particularly effective in blocking tolerance to morphine and reducing the amount of morphine necessary for treating pain.

Examples of pain treatable by the inventive methods include without limitation acute, chronic, cancer, burn, incisional, inflammatory, diabetic neuropathic and back pain.

A preferred NAALADase inhibitor is a compound of formula I, examples of which are set forth above.

Another preferred NAALADase inhibitor is a compound of formula V:

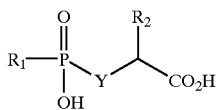

V or a pharmaceutically acceptable equivalent, wherein:

Y is $CR_3R_4$, $NR_5$ or O;

$R_1$ is selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl, Ar, COOR, $NR_6R_7$ and OR, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, COOR, $NR_6R_7$ and Ar;

$R_2$ is selected from the group consisting of hydrogen, $C_1$–$C_6$ alkyl, $C_2$–$C_6$ alkenyl, $C_3$–$C_8$ cycloalkyl, $C_5$–$C_7$ cycloalkenyl, Ar, halo and carboxy, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, $NR_6R_7$ and Ar;

$R_3$ and $R_4$ are independently hydrogen or $C_1$–$C_3$ alkyl;

$R_5$ is hydrogen or $C_1$–$C_3$ alkyl;

R, $R_6$ and $R_7$ are independently selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl and Ar, wherein said alkyl, alkenyl, cycloalkyl and cycloalkenyl are unsubstituted or substituted with one or more substituent (s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent(s) independently selected from the group consisting of halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, carboxy and $NR_1R_2$.

Preferably, Y is $CH_2$.

More preferably, when Y is $CH_2$ then $R_2$ is —$(CH_2)_2$COOH.

Most preferably, when Y is $CH_2$ and $R_2$ is —$(CH_2)_2$COOH, then $R_1$ is hydrogen, $C_1$–$C_4$ alkyl, $C_2$–$C_4$ alkenyl, $C_3$–$C_8$ cycloalkyl, $C_5$–$C_7$ cycloalkenyl, benzyl, phenyl or OR, wherein said alkyl, alkenyl, cycloalkyl, cycloalkenyl, benzyl and phenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, $NR_6R_7$, benzyl and phenyl.

Preferred compounds of formula V are selected from the group consisting of:

2-(phosphonomethyl)pentanedioic acid;

2-[[(2-carboxyethyl)hydroxyphosphinyl]methyl]-pentanedioic acid;

2-(benzylhydroxyphosphinyl) methyl] pentanedioic acid;

2-[(phenylhydroxyphosphinyl)methyl]pentanedioic acid;

2-[[((hydroxy)phenylmethyl)hydroxyphosphinyl]-methyl]pentanedioic acid;

2-[(butylhydroxyphosphinyl)methyl]pentanedioic acid;

2-[[(3-methylbenzyl)hydroxyphosphinyl]methyl]-pentanedioic acid;

2-[(3-phenylpropylhydroxyphosphinyl) methyl]-pentanedioic acid;

2-[[(4-fluorophenyl)hydroxyphosphinyl]methyl]-pentanedioic acid;

2-[(methylhydroxyphosphinyl)methyl]pentanedioic acid;

2-[(phenylethylhydroxyphosphinyl)methyl]-pentanedioic acid;

2-[[(4-methylbenzyl)hydroxyphosphinyl]methyl]-pentanedioic acid;

2-[[(4-fluorobenzyl)hydroxyphosphinyl]methyl]-pentanedioic acid;

2-[[(4-methoxybenzyl)hydroxyphosphinyl]methyl]-pentanedioic acid;

2-[[(3-trifluoromethylbenzyl) hydroxyphosphinyl]-methyl]pentanedioic acid;

2-[[4-trifluoromethylbenzyl) hydroxyphosphinyl]-methyl]pentanedioic acid;

2-[[(2-fluorobenzyl)hydroxyphosphinyl]methyl]-pentanedioic acid;

2-[[(2,3,4,5,6-pentafluorobenzyl)hydroxy-phosphinyl] methyl]pentanedioic acid; and pharmaceutically acceptable equivalents.

More preferably, the compound of formula V is 2-[[(2,3,4,5,6-pentafluorobenzyl)hydroxyphosphinyl]-methyl] pentanedioic acid or a pharmaceutically acceptable equivalent. Most preferably, the compound of formula V is an enantiomer or an enantiomer-enriched mixture.

Representative compounds of formula V wherein $R_1$ is substituted with COOR include without limitation:

2-[[2-carboxypropyl)hydroxyphosphinyl]methyl]-pentanedioic acid;

2-[[2-carboxybutyl)hydroxyphosphinyl]methyl]-pentanedioic acid;

2-[[(2-carboxypentyl)hydroxyphosphinyl]methyl]-pentanedioic acid;

2-[[(2-carboxy-3-phenylpropyl)hydroxyphosphinyl]-methyl]pentanedioic acid;

2-[[2-carboxy-3-naphthylpropyl)hydroxy-phosphinyl] methyl]pentanedioic acid;

2-[[2-carboxy-3-pyridylpropyl)hydroxyphosphinyl]-methyl]pentanedioic acid;

2-[[2-benzyloxycarbonyl)-3-phenylpropyl)hydroxy-phosphinyl]methyl]pentanedioic acid;

2-[[2-methoxycarbonyl)-3-phenylpropyl)hydroxy-phosphinyl]methyl]pentanedioic acid;

2-[[(3-carboxy-2-methoxycarbonyl)propyl)hydroxy-phosphinyl]methyl]pentanedioic acid;

2-[[(4-carboxy-2-methoxycarbonyl) butyl) hydroxy-phosphinyl]methyl]pentanedioic acid; and pharmaceutically acceptable equivalents.

Representative compounds of formula V wherein $R_1$, is substituted with $NR_6R_7$ include without limitation:

2-[({[benzylamino]benzyl}(hydroxyphosphinyl))-methyl]pentanedioic acid;

2-[({[carboxyamino]benzyl}(hydroxyphosphinyl))-methyl]pentanedioic acid;

2-[({[benzylamino]methyl}(hydroxyphosphinyl))-methyl]pentanedioic acid;

2-[({[acetylamino]methyl}(hydroxyphosphinyl))-methyl]pentanedioic acid;

2-[({[diphenylamino]methyl}(hydroxyphosphinyl))-methyl]pentanedioic acid;

2-[({[phenylamino]methyl}(hydroxyphosphinyl))-methyl]pentanedioic acid;

2-({[(phenylcarboxamido)methyl](hydroxy-phosphinyl)}methyl)pentanedioic acid;

2-({[(phenylsulfonamido)methyl](hydroxy-phosphinyl)}methyl)pentanedioic acid;

2-[({[(4-fluorophenyl)amino]methyl}(hydroxy-phosphinyl))methyl]pentanedioic acid;

2-[({[(4-methoxyphenyl)amino]methyl}(hydroxy-phosphinyl))methyl]pentanedioic acid;

2-[({[(4-methylphenyl)amino]methyl}-(hydroxyphosphinyl))methyl]pentanedioic acid;

2-[({[(4-tert-butylphenyl)amino]methyl}-(hydroxyphosphinyl))methyl]pentanedioic acid;

2-[({[(thioformanilido)amino]benzyl}-(hydroxyphosphinyl))methyl]pentanedioic acid;

2-[({[1,3-dioxo-2,3-dihydro-1H-2-isoindolyl]-methyl}hydroxyphosphinyl) methyl] pentanedioic acid; and pharmaceutically acceptable equivalents.

Other NAALADase inhibitors may be found in U.S. Pat. Nos. 5,672,592, 5,795,877, 5,863,536, 5,880,112 and 5,902,817, allowed U.S. patent applications Ser. Nos. 08/825,997, 08/833,628, 08/842,360 and 08/899,319 for which the issue fees have been paid, and International Publications Nos. WO 97/48399, WO 97/48400, WO 97/48409 and WO 98/53812, the entire contents of which patents, applications and publications are herein incorporated by reference.

In a preferred embodiment, the NAALADase inhibitor is administered in combination with morphine.

METHOD FOR TREATING DIABETIC NEUROPATHY

The present invention further relates to a method for treating diabetic neuropathy in a mammal comprising administering to said mammal an effective amount of a NAALADase inhibitor.

Examples of useful NAALADase inhibitors are set forth above.

METHOD FOR PREPARING A COMPOUND CONTAINING BOTH SULFUR AND AN ACID GROUP

The present invention further relates to a method for preparing a compound containing both sulfur and an acid group, comprising the step of reacting a thiolactone with a substituted ester to form a compound of formula VI

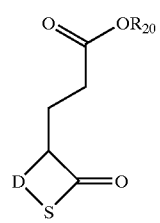

VI wherein:

D is $(CR_{21}R_{22})_n$;

n is 0, 1, 2, 3 or 4; and $R_{20}$, $R_{21}$ and $R_{22}$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s).

Preferably, the method further comprises the step of reacting the compound of formula VI with an alkylating agent to form a pentanedioic acid derivative.

More preferably, the thiolactone is

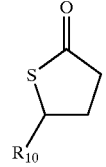

wherein $R_{10}$ is as defined above.

Most preferably, the ester is 3-(bromo)propionic acid ethyl ester.

Additionally, the present invention relates to a method for preparing a compound containing both sulfur and an acid group comprising the steps of:

(i) reacting Meldrum's acid with a sulfur containing reactant to form a Meldrum's acid sulfur containing derivative; and (ii) reacting the Meldrum's acid sulfur containing derivative with an ester to form a compound of formula VII

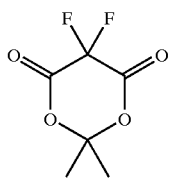

VII wherein:

E is a sulfur containing moiety; and

F is a propionic acid ester containing moiety.

Preferably, the method further comprises the step of functionally derivatizing the compound of formula VII.

More preferably, the thio containing reactant is 3-[(triphenylmethyl)thio]propionic acid.

Most preferably, the ester is 3-(bromo)propionic acid methyl ester.

The present invention also relates to a compound prepared by either of the above methods. Examples of such compound include compounds of formula I.

SYNTHESIS OF NAALADASE INHIBITORS

Some of the NAALADase inhibitors used in the inventive methods can be readily prepared by standard techniques of organic chemistry, utilizing the general synthetic pathways depicted in U.S. Pat. Nos. 5,672,592, 5,795,877, 5,863,536, 5,880,112 and 5,902,817, allowed U.S. patent applications Ser. Nos. 08/825,997, 08/833,628, 08/842,360 and 08/899,319 for which the issue fees have been paid, and International Publications Nos. WO 97/48399, WO 97/48400, WO 97/48409 and WO 98/53812, the entire contents of which patents, applications and publications are herein incorporated by reference.

NAALADase inhibitors of formula V can be readily prepared by standard techniques of organic chemistry, utilizing the general synthetic pathways depicted below in Schemes I–IX. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Scheme I

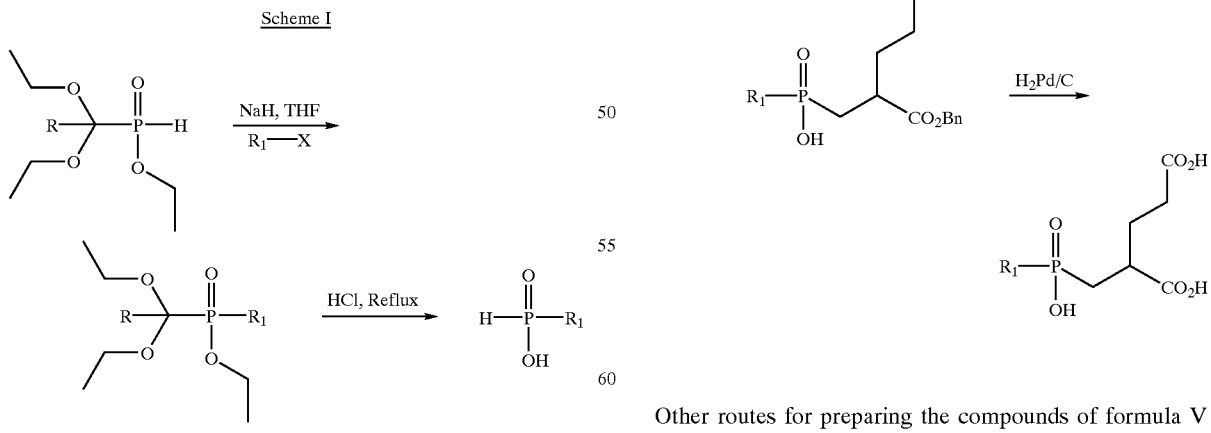

Methods of substituting the R groups are known in the art. Additional methods of synthesizing phosphinic acid esters are described in *J. Med. Chem.*, Vol. 31, pp. 204–212 (1988), and set forth below in Scheme II.

Scheme II

Method A

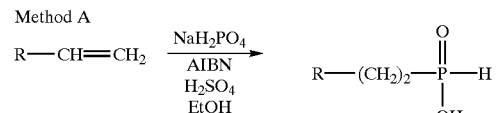

| A. $R_1 = (CH_2)_3Ph$ | H. $R_1 = n\text{-}C_7H_{15}$ |
| B. $(CH_2)_4Ph$ | I. $n\text{-}C_8H_{17}$ |
| C. $(CH_2)_5Ph$ | J. $n\text{-}C_9H_{19}$ |
| D. $(CH_2)_4(P\text{-}F\text{-}Ph)$ | K. $CH_2CHCH_3C_4H_9$ |
| E. $(CH_2)_4\text{-}(3\text{-}pyridyl)$ | L. $CH_2(CH_3)C(CH_3)_2$ |
| F. $n\text{-}C_5H_{11}$ | |
| G. $n\text{-}C_6H_{13}$ | |

Method B

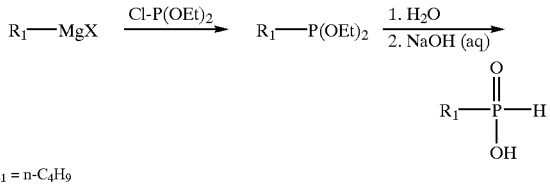

N. $R_1 = n\text{-}C_4H_9$
O. $CHCH_3C_5H_{11}$

Starting with the aforementioned phosphinic acid esters, there are a variety of routes for preparing the compounds of formula V. For example, a general route has been described in *J. Med. Chem.*, Vol. 39, pp. 619–622 (1996), and is set forth below in Scheme Scheme III Scheme III

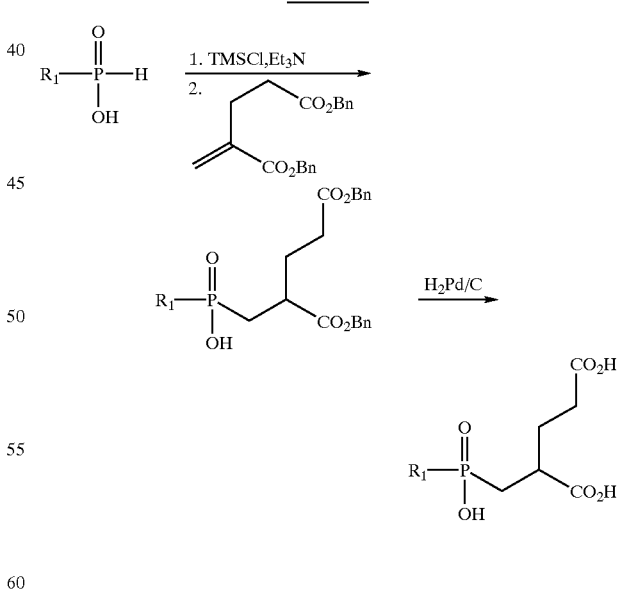

Other routes for preparing the compounds of formula V are set forth below in Scheme IV and Scheme V. Scheme IV and Scheme V show the starting material as a phosphinic acid derivative and the R group as any reasonable chemical substituent including without limitation the substituents listed in Scheme II and throughout the specification.

Scheme IV
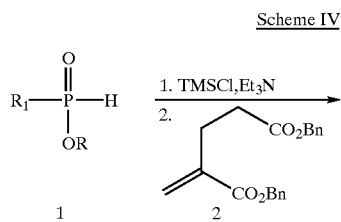
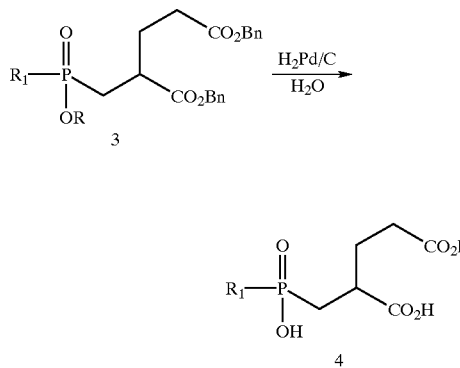
Scheme V
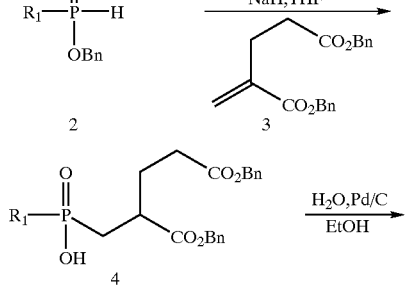
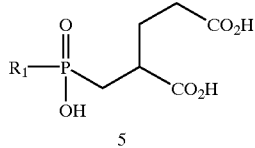
Another route for preparing the compounds of formula V allows for aromatic substitution at $R_1$, and is set forth below in Scheme VI.
Scheme VI
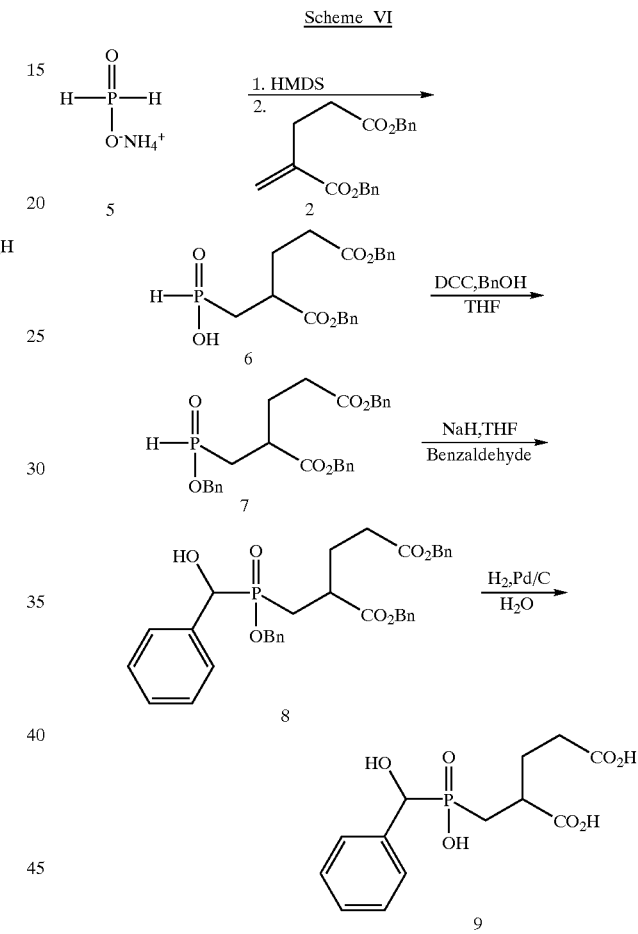
Another route for preparing the compounds of formula V allows for aromatic substitution at the $R_2$ position, and is set forth below in Scheme VII.
Scheme VII
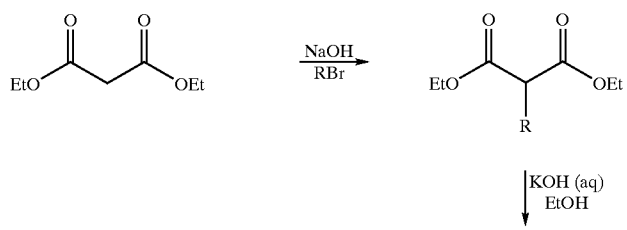

-continued

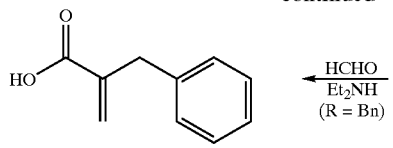 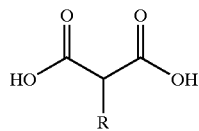

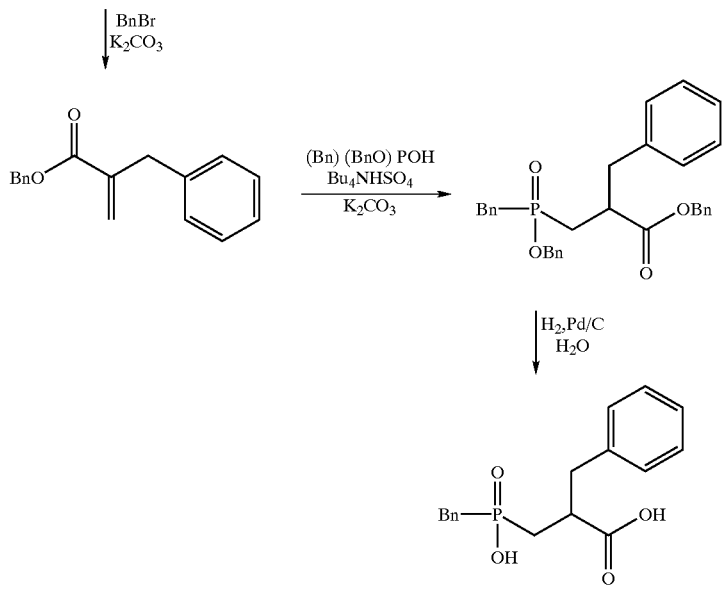

Another route for preparing the compounds of formula V wherein Y is NR$_5$ is set forth below in Scheme VIII.

Scheme VIII

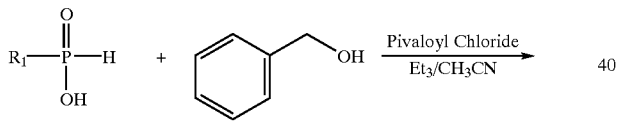

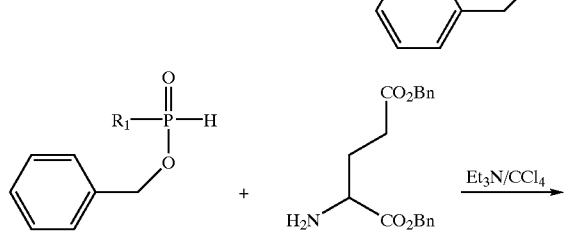

-continued

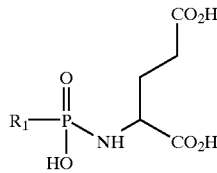

Another route for preparing the compounds of formula V wherein Y is oxygen is set forth below in Scheme IX.

Scheme IX

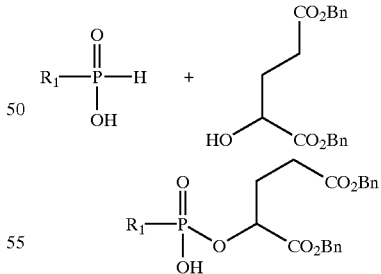

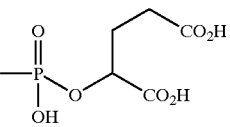

The compounds of formula V wherein R$_1$ is substituted with COOR can be readily prepared by standard techniques of organic chemistry, utilizing the general synthetic pathways depicted below in Scheme X. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995)

Scheme X

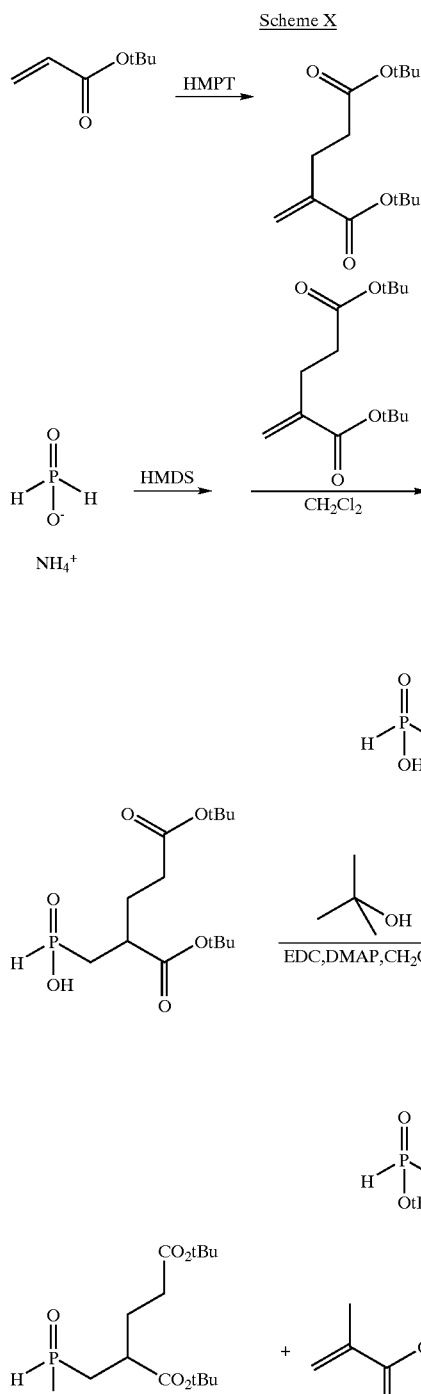

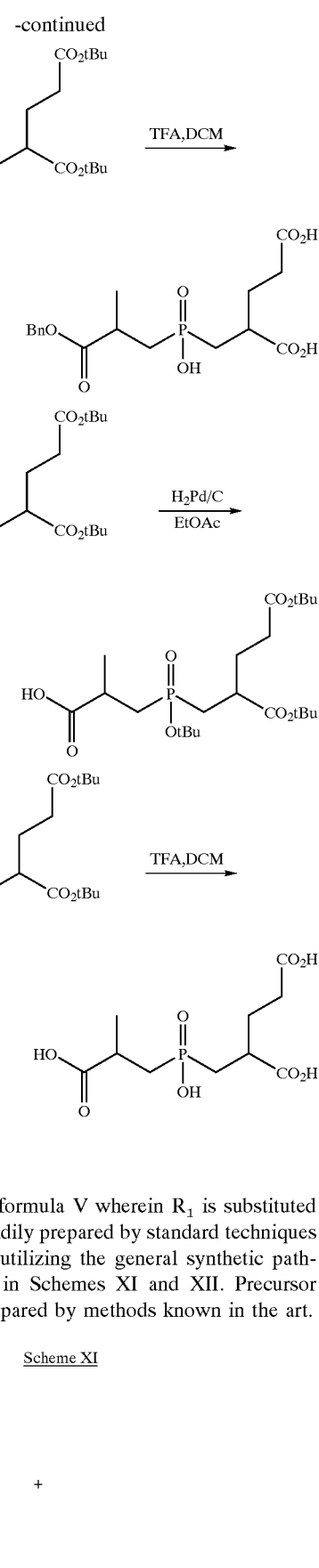

The compounds of formula V wherein $R_1$ is substituted with $NR_6R_7$ can be readily prepared by standard techniques of organic chemistry, utilizing the general synthetic pathways depicted below in Schemes XI and XII. Precursor compounds can be prepared by methods known in the art.

Scheme XI

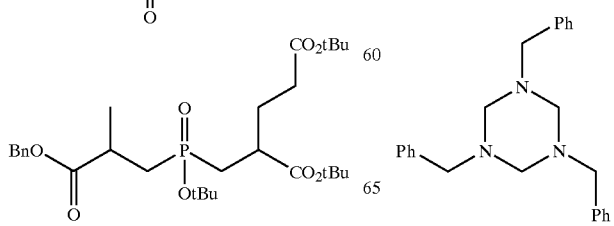

51
-continued
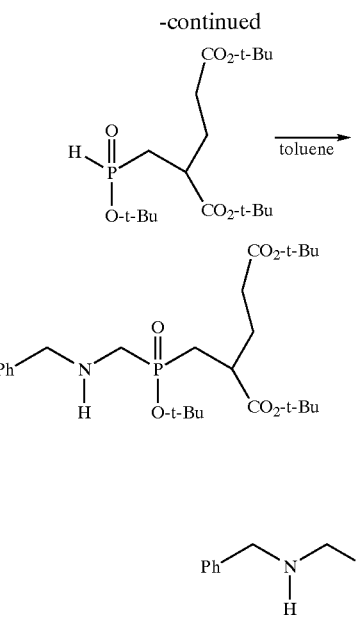
Scheme XII
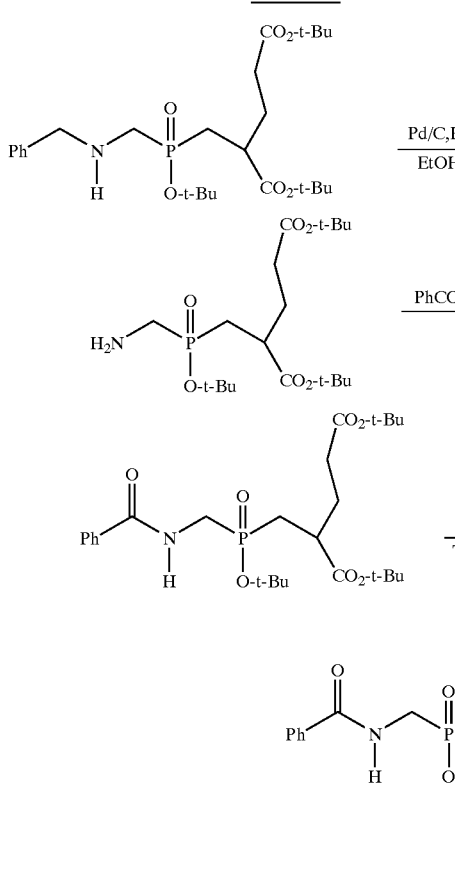
The compounds of formula I wherein X is a moiety of formula II, and A is O or $CR_{17}R_{18}$ can be readily prepared by standard techniques of organic chemistry, utilizing the general synthetic pathways depicted below in Schemes XIII–XXII. Precursor compounds can be prepared by methods known in the art.
52
Scheme XIII
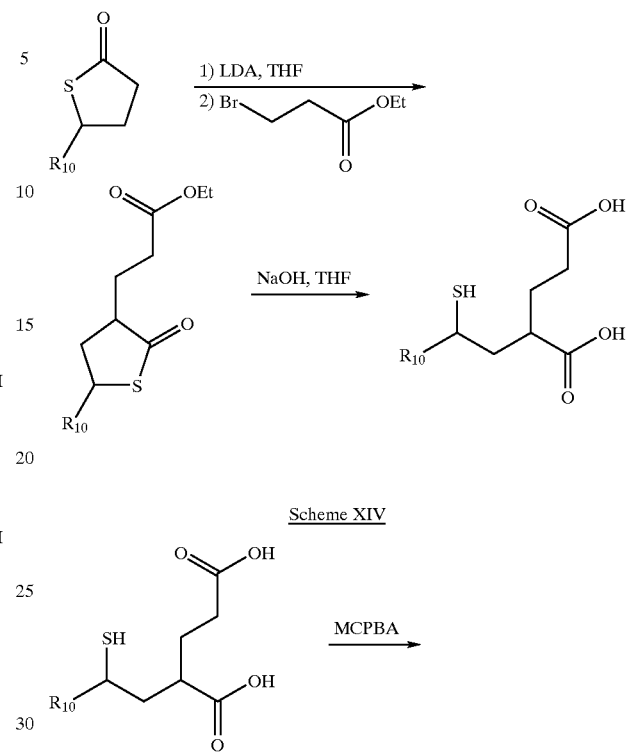
Scheme XIV
Scheme XV
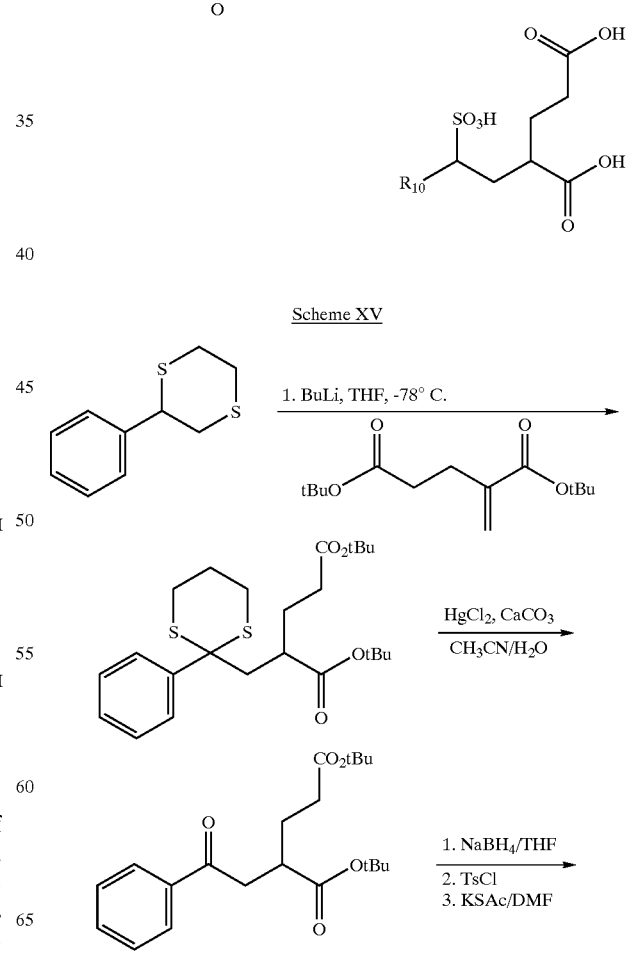

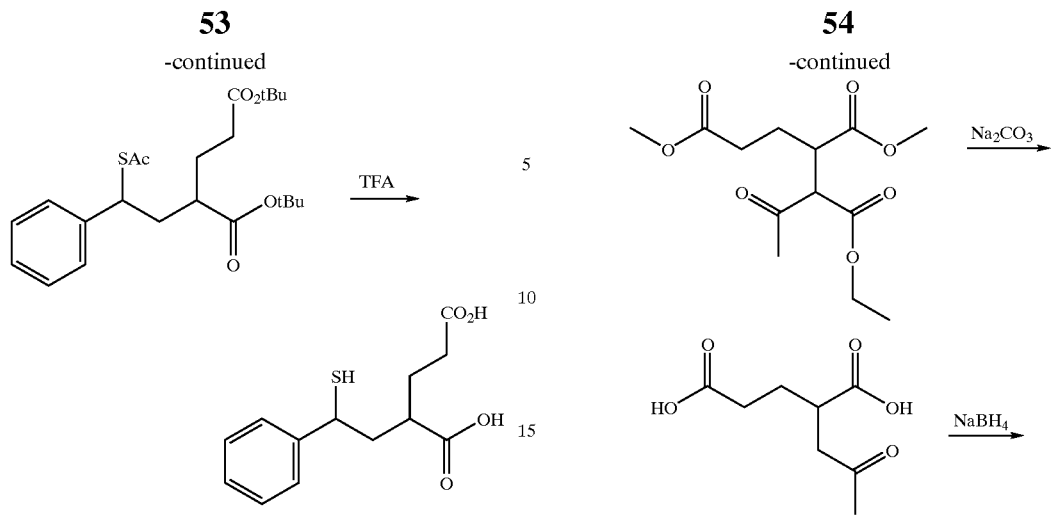
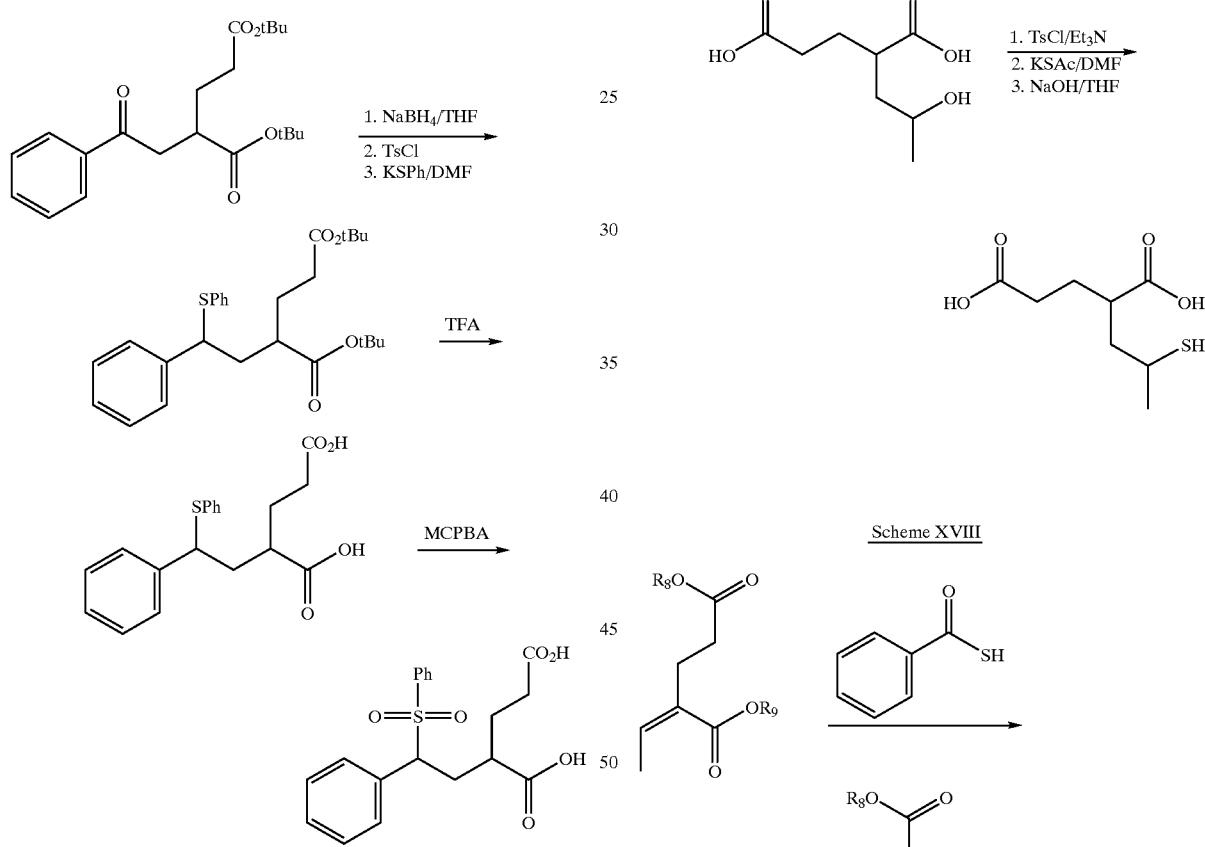
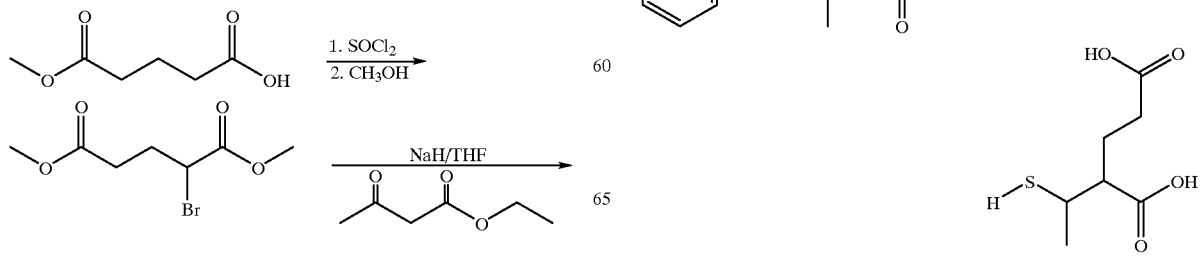

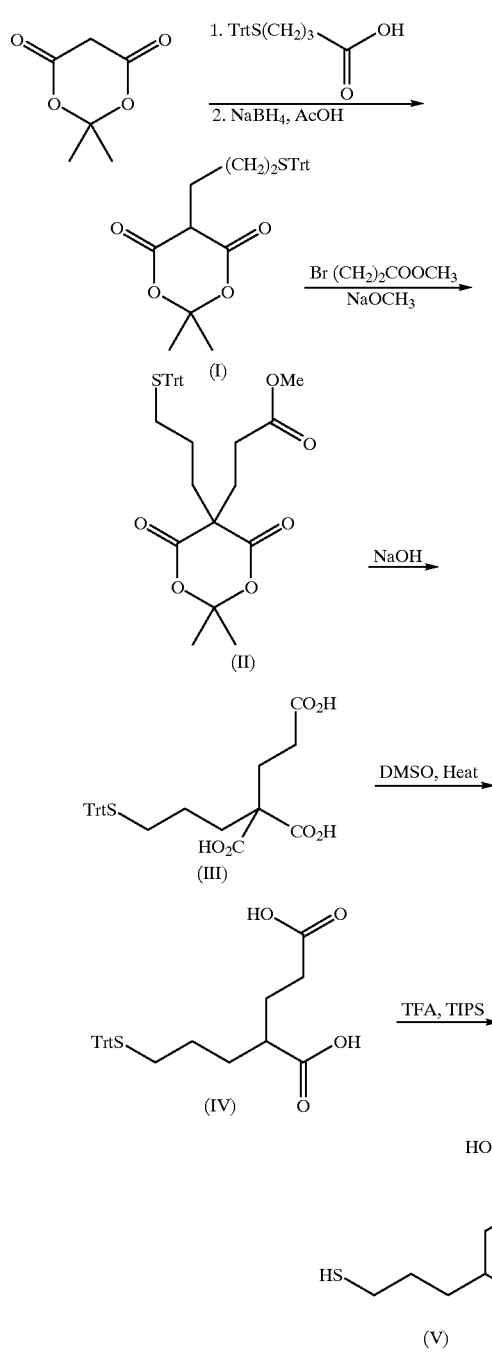

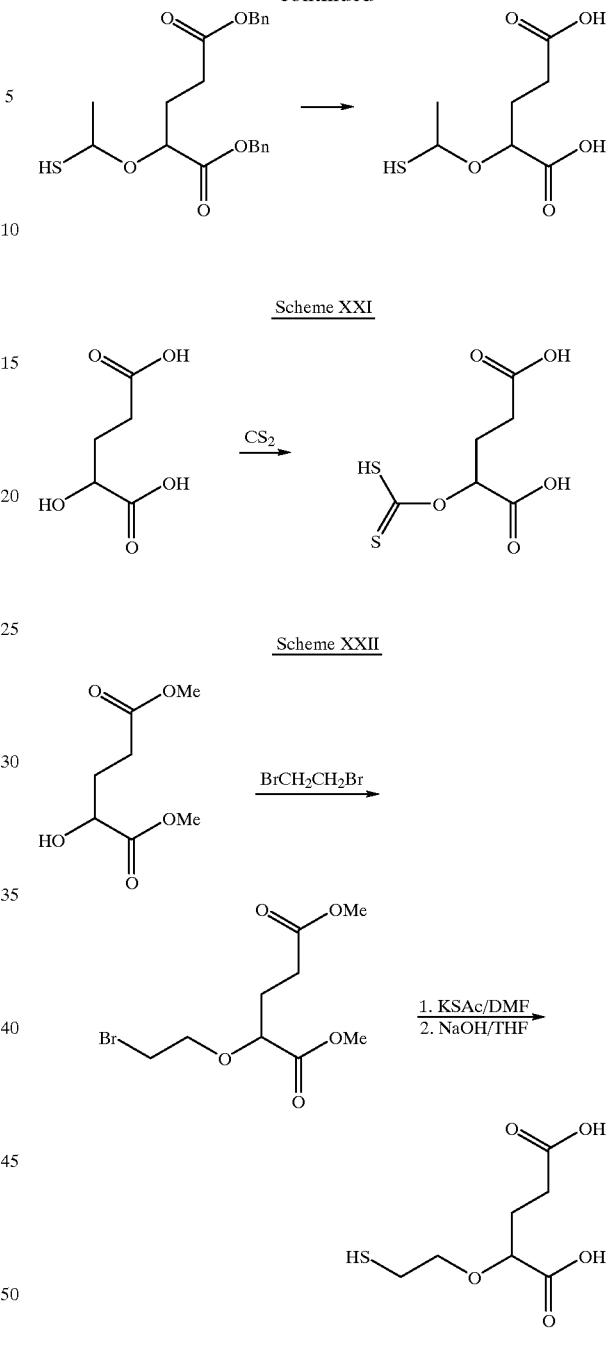

Scheme XX

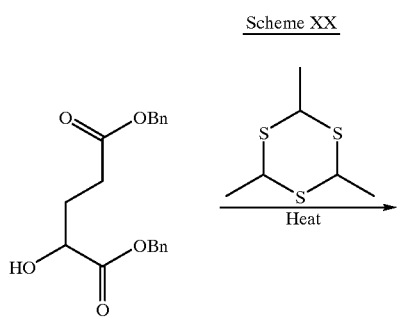

The compounds of formula I wherein X is a moiety of formula II and A is $(CR_{17}R_{18})_mS$ can be readily prepared via standard synthetic methods such as oxidation of the corresponding thiol.

The compounds of formula I wherein X is a moiety of formula II and A is S can be readily prepared via standard synthetic techniques. For example, Scheme XXII can be modified by starting with an appropriately substituted thio compound. In addition, compounds of this class can also be prepared by Michael addition of an appropriately substituted thiol derivative to an α-, β-unsaturated ester.

The compounds of formula I wherein X is a moiety of formula III can be readily prepared using standard synthetic pathways, such as reacting a glutamate derivative with carbon disulfide.

ROUTE OF ADMINISTRATION

In the methods of the present invention, the compounds may be administered by any technique known to be effective in the art, including: orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intramuscular, intraperitoneal, intrathecal, intraventricular, intrasternal, intracranial or intraosseous injection and infusion techniques. Invasive techniques are preferred, particularly direct administration to damaged neuronal tissue.

To be particularly effective therapeutically as central nervous system targets, the compounds should preferably readily penetrate the blood-brain barrier when peripherally administered. Compounds which do not readily penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

DOSAGE

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

In a preferred embodiment, the compounds are administered in lyophilized form. In this case, 1 to 100 mg of a compound of the present invention may be lyophilized in individual vials, together with a carrier and a buffer, such as mannitol and sodium phosphate. The compound may be reconstituted in the vials with bacteriostatic water before administration.

In treating global ischemia, the compounds of the present invention are preferably administered orally, rectally, parenterally or topically at least 1 to 6 times daily, and may follow an initial bolus dose of higher concentration.

The compounds of the present invention may be administered in combination with one or more therapeutic agents, including chemo-therapeutic agents. TABLE I provides known median dosages for selected chemotherapeutic agents. Specific dose levels for these agents and other therapeutic agents will depend upon considerations such as those identified above for the compounds of the present invention.

TABLE I

| CHEMOTHERAPEUTIC AGENT | MEDIAN DOSAGE |
| --- | --- |
| Aldesleukin | 22 million units |
| Asparaginase | 10,000 units |
| Bleomycin Sulfate | 15 units |

TABLE I-continued

| CHEMOTHERAPEUTIC AGENT | MEDIAN DOSAGE |
| --- | --- |
| Carboplatin | 50–450 mg |
| Carmustine | 100 mg |
| Cisplatin | 10–50 mg |
| Cladribine | 10 mg |
| Cyclophosphamide (lyophilized) | 100 mg–2 gm |
| Cyclophosphamide (non-lyophilized) | 100 mg–2 gm |
| Cytarabine (lyophilized powder) | 100 mg–2 gm |
| Dacarbazine | 100 mg–200 mg |
| Dactinomycin | 0.5 mg |
| Daunorubicin | 20 mg |
| Diethylstilbestrol | 250 mg |
| Doxorubicin | 10–150 mg |
| Epoetin Alfa | 2,000–10,000 units |
| Etidronate | 300 mg |
| Etoposide | 100 mg |
| Filgrastim | 300–480 mcgm |
| Floxuridine | 500 mg |
| Fludarabine Phosphate | 50 mg |
| Fluorouracil | 500 mg–5 gm |
| Goserelin | 3.6 mg |
| Granisetron Hydrochloride | 1 mg |
| Idarubicin | 5–10 mg |
| Ifosfamide | 1–3 gm |
| Immune Globulin | 500 mg—10 gm |
| Interferon Alpha-2a | 3–36 million units |
| Interferon Alpha-2b | 3–50 million units |
| Leucovorin Calcium | 50–350 mg |
| Leuprolide | 3.75–7.5 mg |
| Levamisole | 50 mg |
| Mechlorethamine | 10 mg |
| Medroxyprogesterone | 1 gm |
| Melphalan | 50 gm |
| Methotrexate | 20 mg–1 gm |
| Mitomycin | 5–40 mg |
| Mitoxantrone | 20–30 mg |
| Octreotide | 1,000–5,000 mcgm |
| Ondansetron Hydrochloride | 40 mg |
| Paclitaxel | 30 mg |
| Pamidronate Disodium | 30–*90 mg |
| Pegaspargase | 750 units |
| Plicamycin | 2,500 mcgm |
| Sargramostim | 250–500 mcgm |
| Streptozocin | 1 gm |
| Teniposide | 50 mg |
| Thiotepa | 15 mg |
| Vinblastine | 10 mg |
| Vincristine | 1–5 mg |

ADMINISTRATION REGIMEN

For the methods of the present invention, any administration regimen regulating the timing and sequence of drug delivery can be used and repeated as necessary to effect treatment. Such regimen may include pretreatment and/or co-administration with additional therapeutic agents.

To maximize protection of nervous tissue from nervous insult, the compounds should be administered to the affected cells as soon as possible. In situations where nervous insult is anticipated, the compounds should be administered before the expected nervous insult. Such situations of increased likelihood of nervous insult include surgery (cartoid endarterectomy, cardiac, vascular, aortic, orthopedic); endovascular procedures such as arterial catherization (cartoid, vertebral, aortic, cardia, renal, spinal, Adamkiewicz); injections of embolic agents; coils or balloons for hemostasis; interruptions of vascularity for treatment of brain lesions; and predisposing medical conditions such as crescendo transient ischemic attacks, emboli and sequential strokes. Where pretreatment for stroke or ischemia is impossible or impracticable, it is important to get the compounds to the affected cells as soon as possible during or after the event. In the time period between strokes, diagnosis and treatment procedures should be minimized to save the cells from further damage and death.

It is clear that both in animal models of stroke and in humans, the effect of cerebral ischemia are manifest on the cerebral metabolism rapidly, with a timescale measured in minutes or hours. Any form of potential neuroprotective treatment should therefore be given by the most rapidly effective route, which in practice means intravenously. The optimal duration and route of administration of treatment will depend on the individual pharmacokinetic properties of the neuroprotective compound, on the adverse-effect profile of the drug, and on the nature of the insult that gave rise to the stroke. Excitotoxic injury following stroke evolves over at least 4 hours in rodents and possibly beyond 48 hours in humans. Dyker et al., "Duration of Neuroprotective Treatment for Ischemic Stroke," Stroke, Vol. 29, pp. 535–542 (1998). Thus, it would be desirable to provide neuroprotection throughout this critical time period. Ideally, any compound for the treatment of stroke should adequately cross the blood-brain barrier and obtain sufficiently therapeutic levels within the brain and CSF.

For patients with prostate cancer that is neither advanced nor metastatic, the compounds of the present invention may be administered (i) prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic prostate cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

COMBINATION WITH OTHER TREATMENTS a. Nervous Insult

In methods of treating nervous insult (particularly acute ischemic stroke and global ischemia caused by drowning and head trauma), the compounds of the present invention can be co-administered with one or more therapeutic agents, preferably agents which can reduce the risk of stroke (such as aspirin), and more preferably agents which can reduce the risk of a second ischemic event (such as ticlopidine).

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

b. Angiogenesis-Dependent Disease

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

c. Cancer

Surgery and Radiation Treatment

In general, surgery and radiation treatment are employed as potentially curative therapies for patients with localized cancer who are under 70 years of age and are expected to live at least 10 more years.

If treated with surgery alone, however, many patients will experience recurrence of the cancer. Radiation treatment can also be problematic as the radiotherapeutic agents are toxic to normal tissues, and often create life-threatening side effects.

Use of the present invention in conjunction with surgery and radiation treatment could prevent remission and allow lower dosage levels of toxic radiotherapeutic agents. Based on the above statistics, there is considerable opportunity to use the present invention in conjunction with, or as an alternative to, surgery and/or radiation treatment.

Radiosensitizers

Radiosensitizers are known to increase the sensitivity of cancerous cells to the toxic effects of electromagnetic radiation. Several mechanisms for the mode of action of radiosensitizers have been suggested in the literature, including: hypoxic cell radiosensitizers (e.g., 2-nitroimidazole compounds and benzotriazine dioxide compounds) promote the reoxygenation of hypoxic tissue, and/or catalyze the generation of damaging oxygen radicals; non-hypoxic cell radiosensitizers (e.g., halogenated pyrimidines), which can be analogs of DNA bases, preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include without limitation: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) employs visible light as the electromagnetic radiation activator of the sensitizing agent. Examples of photodynamic electromagnetic radiosensitizers include without limitation: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

The compounds of the present invention may be administered in combination with electromagnetic radiosensitizers to increase the sensitivity of cancerous cells to the toxic effects of electromagnetic radiation. Use of the present invention in conjunction with electromagnetic radiosensitizers could prevent remission and allow lower dosage levels of electromagnetic radiation. Combining electromagnetic radiation with the compounds, compositions and methods of the present invention should be more effective than electromagnetic radiation alone in treating cancer.

When combined with electromagnetic radiosensitizers, the compounds of the present invention may also be administered in conjunction with one or more of the following compounds: compounds which promote the incorporation of radiosensitizers to the target cells; compounds which control the flow of therapeutics, nutrients and/or oxygen to the target cells; chemotherapeutic agents which act on the tumor with or without additional electromagnetic radiation; or other therapeutic agents for treating cancer or other diseases. Examples of such therapeutic agents include without limitation: 5-fluorouracil, leucovorin, 5'-amino-5'deoxythymidine, oxygen, carbogen, red cell transfusions, perfluorocarbons (e.g. Fluosol-DA), 2,3-DPG, BW12C, calcium channel blockers, pentoxyfylline, hydralazine, and L-BSO. Examples of chemotherapeutic agents are listed in TABLE I.

Hormonal Therapy

Hormonal ablation by medication and/or orchiectomy is used to block hormones that promote further growth and metastasis of cancer. With time, both the primary and metastatic tumors of virtually all of these patients become hormone-independent and resistant to therapy. Continuous supplementation with the compounds of the present invention may be used to prevent or reverse this potentially metastasis-permissive state.

Chemotherapy

Chemotherapy has been successful in treating some forms of cancer. However, in treating other forms of cancer, chemotherapy has been reserved only as a last resort. In any case, chemotherapy can be problematic as chemotherapeutic agents are toxic to normal tissues and often create life threatening side effects. Additionally, chemotherapy often has high failure and/or remission rates.

Use of the present invention in conjunction with chemotherapy could prevent remission and allow lower dosage levels of toxic chemotherapeutic agents. Combining chemotherapy with the methods of the present invention should be more effective than chemotherapy alone in treating cancer.

Immunotherapy

The compounds of the present invention may also be used in combination with monoclonal antibodies to treat cancer. The present invention may also be used with immunotherapies based on polyclonal or monoclonal antibody-derived reagents. These reagents are well known in the art, and include radiolabeled monoclonal antibodies such as monoclonal antibodies conjugated with strontium-89.

In Vivo Toxicity of NAALADase Inhibitors

The in vivo toxicological effect of NAALADase inhibition has been examined in mice. The results show that NAALADase inhibitors are non-toxic to mice, suggesting that it would be similarly non-toxic to humans when administered at therapeutically effective amounts. Representative disclosure may be found in U.S. Pat. Nos. 5,672,592, 5,795,877, 5,804,602, 5,824,662, 5,863,536, 5,880,112 and 5,902,817, and allowed U.S. patent applications Ser. Nos. 08/825,997, 08/833,628, 08/842,360 and 08/899,319 for which the issue fees have been paid, the entire contents of which patents and applications are herein incorporated by reference.

In Vitro Inhibition of NAALADase Activity

Various compounds formulas I–V were tested for in vitro inhibition of NAALADase activity. Some results are set forth in U.S. Pat. Nos. 5,672,592, 5,795,877, 5,863,536, 5,880,112 and 5,902,817, allowed U.S. patent applications Ser. Nos. 08/825,997, 08/833,628, 08/842,360 and 08/899,319 for which the issue fees have been paid, the entire contents of which patents and applications are herein incorporated by reference. Other results are provided below in TABLE II.

TABLE II

IN VITRO INHIBITION OF NAALADASE ACTIVITY

| Compound | $K_i$ (nM) |
|---|---|
| (structure) | 2000 |
| (structure) | 548 |
| (structure) | 234 |
| (structure) | 740 |
| (structure) | 198 |

TABLE II-continued

IN VITRO INHIBITION OF NAALADASE ACTIVITY

| Compound | $K_i$ (nM) |
| --- | --- |
| [structure] | 4250 |
| [structure] | 13 |
| [structure] | 0.6 |
| [structure] | 95 |
| [structure] | 2 |
| [structure] | 313 |

TABLE II-continued

IN VITRO INHIBITION OF NAALADASE ACTIVITY

| Compound | $K_i$ (nM) |
|---|---|
| [phenyl-CH(NH-C(O)-OH)-P(O)(OH)-CH2-CH(CO2H)-CH2-CH2-CO2H] | 2000 |
| [benzyl-NH-CH2-P(O)(OH)-CH2-CH(CO2H)-CH2-CH2-CO2H] | 52 |
| [CH3-C(O)-NH-CH2-P(O)(OH)-CH2-CH(CO2H)-CH2-CH2-CO2H] | 118 |
| [dibenzyl-N-CH2-P(O)(OH)-CH2-CH(CO2H)-CH2-CH2-CO2H] | 175 |
| [phthalimido-N-CH2-P(O)(OH)-CH2-CH(CO2H)-CH2-CH2-CO2H] | 34 |

TABLE II-continued
IN VITRO INHIBITION OF NAALADASE ACTIVITY
| Compound | $K_i$ (nM) |
|---|---|
| 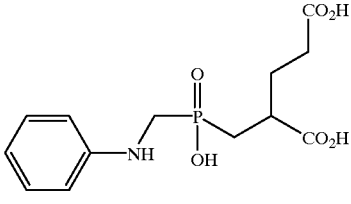 | 6 |
| 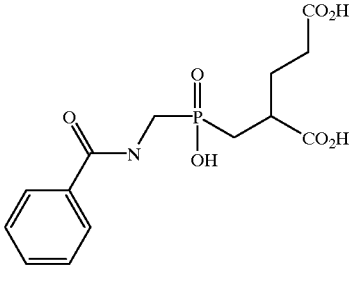 | 142 |
| 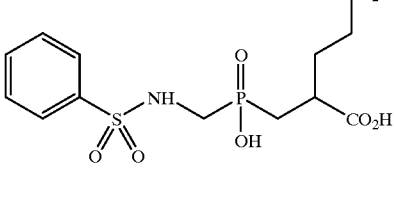 | 90.0 |
| 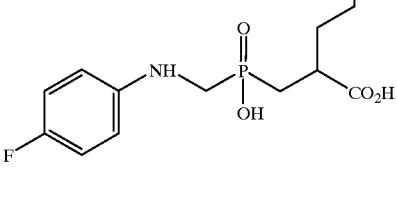 | 9.0 |
| 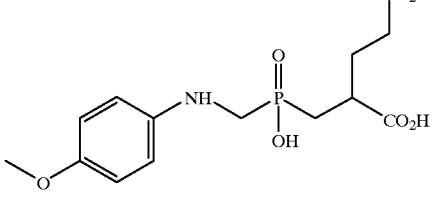 | 2 |
| 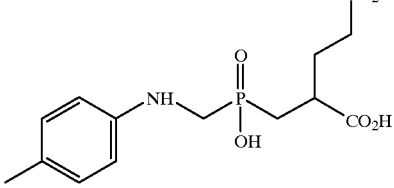 | 5 |

TABLE II-continued

IN VITRO INHIBITION OF NAALADASE ACTIVITY

| Compound | $K_i$ (nM) |
|---|---|
| [structure: 4-tert-butylphenyl-NH-CH2-P(O)(OH)-CH2-CH(CO2H)-CH2-CH2-CO2H] | 2 |
| [structure: Ph-NH-C(=S)-NH-CH2-P(O)(OH)-CH2-CH(CO2H)-CH2-CH2-CO2H] | 75 |
| [structure] 2-(2-sulfanylethyl)pentanedioic acid | 510 |
| [structure] 2-(2-sulfanylhexyl)pentanedioic acid | 4750 |
| [structure] 2-(1-methyl-2-sulfanylethyl)pentanedioic acid | 843 |
| [structure] 2-(2-sulfanylpropyl)pentanedioic acid | 158 |

TABLE II-continued
IN VITRO INHIBITION OF NAALADASE ACTIVITY
| Compound | $K_i$ (nM) |
|---|---|
| 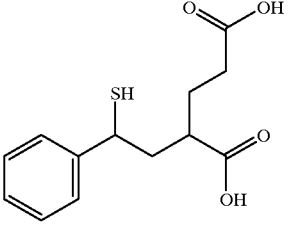<br>2-(2-phenyl-2-sulfanylethyl)pentanedioic acid | 4650 |
| 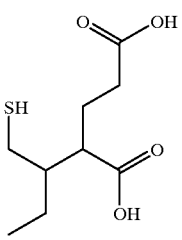<br>2-(1-ethyl-2-sulfanylethyl)pentanedioic acid | 1550 |
| 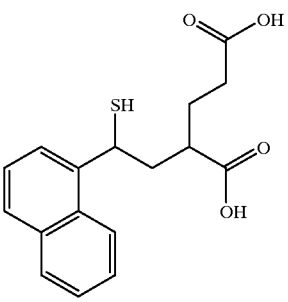<br>2-(2-naphthyl-2-sulfanylethyl)pentanedioic acid | 10000 |
| 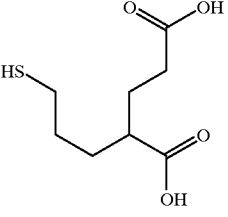<br>2-(3-sulfanylpropyl)pentanedioic acid | 100 |
| 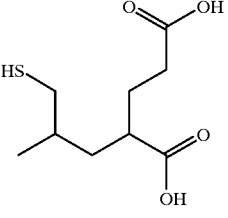<br>2-(3-sulfanyl-2-methylpropyl)pentanedioic acid | 239 |

TABLE II-continued

IN VITRO INHIBITION OF NAALADASE ACTIVITY

| Compound | $K_i$ (nM) |
|---|---|
| 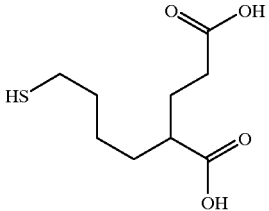<br>2-(4-sulfanylbutyl)pentanedioic acid | 1128 |
| 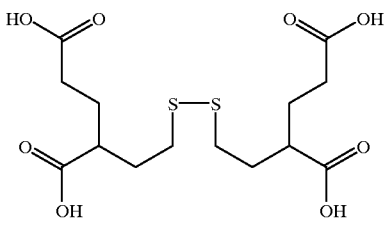<br>2-[2-[(3,5-dicarboxypentyl)dithio]ethyl]pentanedioic acid | 16500 |

In Vitro Assay of NAALADase Inhibitors on Ischemia

To examine the in vitro effect of NAALADase inhibitors on ischemia, cortical cell cultures were treated with various NAALADase inhibitors during an ischemic insult (potassium cyanide and 2-deoxyglucose) and for one hour thereafter (for experimental details, see Vornov et al., *J. Neurochem.*, Vol. 65, No. 4, pp. 1681–1691 (1995)). Some results are set forth in U.S. Pat. Nos. 5,672,592, 5,795,877, 5,863,536, 5,880,112 and 5,902,817, allowed U.S. patent applications Ser. Nos. 08/825,997, 08/833,628, 08/842,360 and 08/899,319 for which the issue fees have been paid, the entire contents of which patents and applications are herein incorporated by reference. Other results are provided below in TABLE III. Neuroprotective effect is expressed as $EC_{50}$, the concentration which is required to cause a 50% reduction in glutamate toxicity following an ischemic insult.

TABLE III

| Compound | $K_i$ (nM) |
|---|---|
| 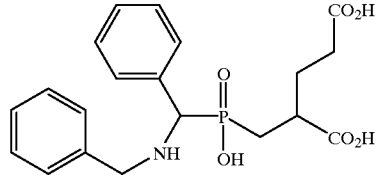 | 1 |
| 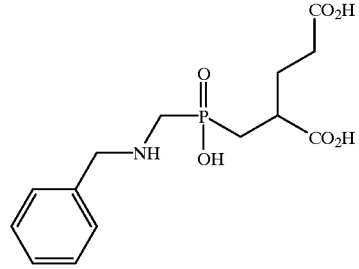 | 0.9 |

TABLE III-continued

| Compound | $K_i$ (nM) |
|---|---|
| (phthalimide-N-CH$_2$-P(O)(OH)-CH$_2$-CH(CO$_2$H)-CH$_2$-CH$_2$-CO$_2$H) | 13 |
| (PhNH-CH$_2$-P(O)(OH)-CH$_2$-CH(CO$_2$H)-CH$_2$-CH$_2$-CO$_2$H) | 12 |
| (PhSO$_2$-NH-CH$_2$-P(O)(OH)-CH$_2$-CH(CO$_2$H)-CH$_2$-CH$_2$-CO$_2$H) | 792 |
| (4-F-C$_6$H$_4$-NH-CH$_2$-P(O)(OH)-CH$_2$-CH(CO$_2$H)-CH$_2$-CH$_2$-CO$_2$H) | 3 |
| (4-MeO-C$_6$H$_4$-NH-CH$_2$-P(O)(OH)-CH$_2$-CH(CO$_2$H)-CH$_2$-CH$_2$-CO$_2$H) | 10 |
| (4-Me-C$_6$H$_4$-NH-CH$_2$-P(O)(OH)-CH$_2$-CH(CO$_2$H)-CH$_2$-CH$_2$-CO$_2$H) | 11 |

TABLE III-continued

| Compound | $K_i$ (nM) |
|---|---|
| [structure: 4-tert-butylphenyl-NH-CH₂-P(O)(OH)-CH₂-CH(CO₂H)-CH₂CH₂-CO₂H] | 35 |
| [structure: bis-glutaryl phosphinate with two benzyl esters] | 0.01 |
| [structure: bis-glutaryl phosphinate tetraacid] | 0.04 |
| [structure: HS-CH₂CH₂-CH(CO₂H)-CH₂CH₂-CO₂H]<br>2-(2-sulfanylethyl)pentanedioic acid | 2 |
| [structure: CH₃(CH₂)₃-CH(SH)-CH₂-CH(CO₂H)-CH₂CH₂-CO₂H]<br>2-(2-sulfanylhexyl)pentanedioic acid | 1000 |
| [structure: CH₃-CH(SH-CH₂-)-CH(CO₂H)-CH₂CH₂-CO₂H] | 141 |

TABLE III-continued
| Compound | $K_i$ (nM) |
|---|---|
| 2-(1-methyl-2-sulfanylethyl)pentanedioic acid 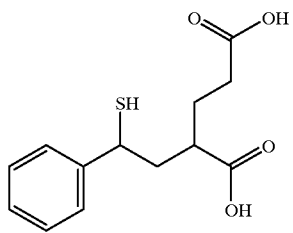 | 29 |
| 2-(2-phenyl-2-sulfanylethyl)pentanedioic acid 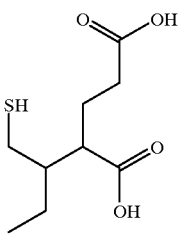 | 62 |
| 2-(1-ethyl-2-sulfanylethyl)pentanedioic acid 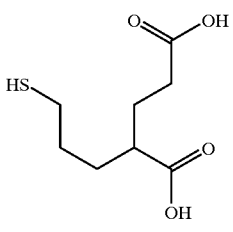 | 13 |
| 2-(3-sulfanylpropyl)pentanedioic acid 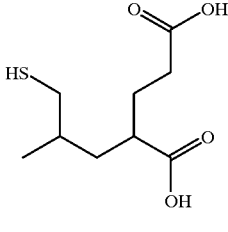 | 80 |
| 2-(3-sulfanyl-2-methylpropyl)pentanedioic acid 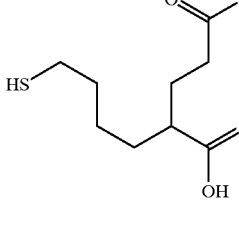 | 36 |
| 2-(4-sulfanylbutyl)pentanedioic acid | |

TABLE III-continued

| Compound | $K_i$ (nM) |
|---|---|
| 2-[2-[(3,5-dicarboxypentyl)dithio]ethyl]pentanedioic acid | 17 |

The dose-response of this effect, as measured by the % toxicity at different concentrations of NAALADase inhibitor Compound 3, is provided in U.S. Pat. Nos. 5,672,592, 5,795,877, 5,804,602, 5,824,662, 5,863,536, 5,880,112 and 5,902,817, and allowed U.S. patent applications Ser. Nos. 08/825,997, 08/833,628, 08/842,360 and 08/899,319 for which the issue fees have been paid, the entire contents of which patents and applications are herein incorporated by reference.

In Vivo Assay of NAALADase Inhibitors on Brain Injury following MCAO in Sprague-Dawley Rats To examine the neuroprotective effect of NAALADase inhibitors on brain injury in vivo, Sprague-Dawley rats were treated with a vehicle, and either Compound 1 or 2-(3-sulfanylpropyl)pentanedioic acid.

The control group received Hepes buffered saline.

Four drug treated groups received Compound 1. For each rat, the treatment was initiated at 60 minutes post middle cerebral artery occlusion (MCAO) by an IV bolus injection which was immediately followed by IV infusion for 4 hours at rate of 0.5 ml/hr. Group 1 (n=9) received a dose of 100 mg/kg IV bolus followed by 20 mg/kg/hr IV infusion for 4 hours. Group 2 (n=11) received a dose of 30 mg/kg IV bolus followed by 6 mg/kg/hr IV infusion for 4 hours. Group 3 (n=9) received a dose of 10 mg/kg IV bolus followed by 2 mg/kg/hr IV infusion for 4 hours. Group 3 rats were also treated at 120 minutes, 180 minutes and 360 minutes post-occlusion. Group 4 (n=8) received a dose of 3 mg/kg IV bolus followed by 3 mg/kg/hr IV infusion for 4 hours.

Two additional drug treated groups received 2-(3-sulfanylpropyl)pentanedioic acid. For each rat, the treatment was initiated at 120 minutes post middle cerebral artery occlusion (MCAO) by an IV bolus injection which was immediately followed by IV infusion for 4 hours at rate of 0.5 ml/hr. Group 5 received a dose of 30 mg/kg IV bolus followed by 6 mg/kg/hr IV infusion for 4 hours. Group 6 received a dose of 10 mg/kg IV bolus followed by 2 mg/kg/hr IV infusion.

Twenty two hours following the reperfusion, the rats were euthanized and their brains were removed. Seven coronal sections (2 mm thick) were taken and stained with 1 % solution of 2,3,5-triphenyl-tetraxolium chloride (TTC) for 20 minutes and then fixed in 10% formalin. The anterior and posterior surface of the most rostral brain section and the posterior surface of each of the remaining 6 sections were imaged. The quantification of infarct size of each brain was obtained using a computer aided-digital imaging analysis system (LOATS). The brain regions completely lacking TTC-staining were characterized as representative of infarcted tissue. The total infarct volume for each rat was calculated by numeric integration of the respective sequential brain areas.

The total infarct volume for each group of rats is provided below in TABLES IV(a) and IV(b).

TABLE IV(a)

Rats treated with Compound 1

| Dose (mg/kg) | Admin. Time (minutes) | % Protect | p value |
|---|---|---|---|
| 100 | 60 post | 44 | 0.0142 |
| 30 | 60 post | 52 | 0.0020 |
| 10 | 60 post | 50 | 0.0058 |
| 10 | 120 post | 33 | 0.021 |
| 10 | 180 post | 47 | 0.014 |
| 10 | 360 post | 50 | 0.002 |
| 3 | 60 post | 52 | 0.0037 |
| 1 | 60 post | 20 | 0.3611 |

TABLE IV(b)

Rats treated with 2-(3-sulfanylpropyl)pentanedioic acid

| Dose (mg/kg) | Admin. Time (minutes) | % Protect | p value |
|---|---|---|---|
| 30 | 120 post | 52 | 0.0003 |
| 10 | 120 post | 21 | 0.29 |

Vehicle treated rats exhibited a mean total brain infarct volume of 265±33 mm$^3$.

Rats treated with Compound 1 exhibited significantly smaller infarct size. The mean total brain infarct volumes for the four Compound 1 treated groups were: 123 ±31 mm$^3$ for Group 1 (p=0.014 vs. vehicle group); 141 ±78 mm$^3$ for Group 2 (p=0.002 vs. vehicle group); 152 ±32 mm$^3$ for Group 3 (treated at 60 minutes post-occlusion; p=0.0058 vs. vehicle group); 117 ±22 mm$^3$ for Group 4 (p=0.0037 vs. vehicle group). These results indicate that Compound 1 is neuroprotective in rat MCAO model of stroke when administered 60 minutes, 120 minutes, 180 minutes and 360 minutes post-occlusion.

Rats treated with 2-(3-sulfanylpropyl)-pentanedioic acid at 30 mg/kg IV bolus followed by 6 mg/kg/hr IV infusion for 4 hours also exhibited significantly smaller infarct size than the vehicle treated rats. Thus, at that particular dose level, 2-(3-sulfanylpropyl)pentanedioic acid is neuroprotective in rat MCAO model of stroke when administered at 120 minutes post-occlusion.

Stroke patients often experience a significant temporal delay between the onset of ischemia and the time to initiation of therapy. Thus, there is a need for neuroprotectants with a long therapeutic window of opportunity. The data above shows that the inventive compounds have a therapeutic window of opportunity of at least 6 hours in rat MCAO model of stroke. One of ordinary skill in the art would expect that window to be greater in humans.

Protocol for In Vivo Assay of NAALADase Inhibitors on Brain Injury

Male Sprague-Dawley rats (260–320 g) were used. They were individually housed and allowed free access to food and water. Two days prior to the experiment, they were given restricted food if necessary to maintain the body weight. Each rat received two surgeries: femoral vein cannulation for IV infusion and MCAO. During surgeries, the rat was anesthetized with 1.5% halothane delivered in oxygen via an inhalation mask. The body temperature was monitored and regulated at normothermic level using a homeothermic heating system. First, a catheter was inserted into the left femoral vein. Thirty minutes later, the rat was reanesthetized for MCAO surgery. The MCAO was achieved using the endovascular suture method described by Long et al., *Stroke*, Vol. 20, pp. 84–91 (1989). Specifically, the right external carotid artery (ECA) was exposed, coagulated and transected. A 3-0 monofilament nylon suture with a blunted tip and a coat of 0.05% Poly-1-Lysine was introduced into the proximal stump of the ECA via an arteriotomy. It was advanced 22 mm from the carotid bifurcation until it lodged in the proximal region of the anterior cerebral artery, thereby occluding the origin of the MCA. The rats were allowed to wake up; 2 hours later, the rats were reanesthetized for reperfusion, during which the nylon suture was retracted to the stump of the ECA allowing blood recirculation to the MCA.

In Vivo Assay of NAALADase Inhibitors on Stroke-Induced Rise in Brain Glutamate Levels Compound 3 was tested for its effect on hyperglutamatergic disorders in vivo in rats with stroke-induced extracellular glutamate increases. The protocol and results are set forth in allowed U.S. patent application Ser. No. 08/899,319 for which an issue fee has been paid, the entire content of which application is herein incorporated by reference. The results show that Compound 3 treatment significantly attenuated stroke-induced extracellular glutamate increases in the striatum, and completely prevented concurrent glutamate changes in the parietal cortex.

In Vitro Assay of NAALADase Inhibitors on Myelination in Dorsal Root Ganglia-Schwann Cell Co-Cultures Inhibition of NAALADase results in significant increase in the number of myelinated axons and myelin thickness as compared to vehicle-treated mice following sciatic nerve cryolesion (*Soc. Neurosci. Abstr.*, Vol. 23, No. 2, p. 2302 (1997)). The inventors hypothesized that NAALADase may play a role in signaling myelin formation and inhibition of NAALADase may facilitate myelination. To test this hypothesis, the inventors examined the effects of several NAALADase inhibitors in a well established in vitro model system of myelination. Dorsal root ganglia-Schwann cell co-cultures were established as previously described (Einheber et al., *J. Cell. Biol.*, Vol. 123, p. 1223). Following 7 days in co-culture, myelination was initiated following the addition of serum and ascorbic acid with various doses of NAALADase inhibitors (1 nM to 10 $\mu$M) or progesterone (20 nM; positive control). The extent of myelination was examined between days 14–21 using immunocytochemical staining for myelin basic protein (MBP), a known myelin marker. Qualitative analysis of the immunostained cultures revealed a significant dose-response related increase in the number of myelinated axons following the addition of NAALADase inhibitors as compared to axons in vehicle-treated cultures. As depicted in FIGS. 1A–C and 2A–C, a two week treatment of the NAALADase inhibitors Compounds 3 and 2 (1 nM) caused a significant increase in the immunostaining of MBP. Cultures treated with a high dose of Compound 3 or Compound 2 (1 $\mu$M) had a greater extent of myelination than cultures treated with maximal doses of ascorbic acid and progesterone. These results suggest that inhibition of NAALADase may facilitate myelination and may be useful clinically in the treatment of demyelinating diseases.

In Vivo Assay of NAALADase Inhibitors on Myelin Formation Following Sciatic Nerve Cryolesion Compound 3 was tested in vivo for its effect on nerve regeneration and myelination following cryolesion of the sciatic nerve in male mice. The protocol and results are set forth in allowed U.S. patent application Ser. No. 08/899,319 for which an issue fee has been paid, the entire content of which application is herein incorporated by reference. The results show that sciatic nerves in mice treated with Compound 3 exhibited an increase in myelinated axon number and an increase in myelin thickness.

In Vivo Assay of NAALADase Inhibitors on Parkinson's Disease

Compound 3 was tested in vivo for its effect on Parkinson's disease in MPTP lesioned mice. The protocol and results are set forth in allowed U.S. patent application Ser. No. 08/899,319 for which an issue fee has been paid, the entire content of which application is herein incorporated by reference. The results show that MPTP lesioned mice receiving Compound 3 showed a significant recovery of TH-stained dopaminergic neurons, suggesting that Compound 3 protects against MPTP-toxicity.

In Vivo Assay of NAALADase Inhibitors on Dynorphin-Induced Spinal Cord Injury

Compound 3 was tested in vivo for its effect on excitotoxic spinal cord injury in rats with dynorphin-induced spinal cord injury. The protocol and results are set forth in allowed U.S. patent application Ser. No. 08/899,319 for which an issue fee has been paid, the entire content of which application is herein incorporated by reference. The results show that when co-administered with dynorphin A, Compound 3 caused significant improvement in motor scores by 24-hour post-injection, suggesting that Compound 3 provides effective protection against dynorphin-induced spinal cord injury.

In Vitro Assay of NAALADase Inhibitors on Amyotrophic Lateral Sclerosis (ALS)

Compound 3 was tested in vitro for its effect on Amyotrophic Lateral Sclerosis (ALS) in spinal cord organotypic cultures. The protocol and results are set forth in allowed U.S. patent application Ser. No. 08/899,319 for which an issue fee has been paid, the entire content of which application is herein incorporated by reference. The results show that Compound 3 exhibited dose-dependent protection against THA-induced toxicity.

In Vivo Assay of NAALADase Inhibitors on Ethanol Consumption in Alcohol-Preferring Rats Compound 3 was tested in vivo for its effect on ethanol consumption in alcohol-preferring rats. The protocol and results are set forth in allowed U.S. patent application Ser. No. 08/899,319 for which an issue fee has been paid, the entire content of which application is herein incorporated by reference. The results show that Compound 3 significantly reduced ethanol consumption without affecting body weights or 24 hour water intakes, suggesting that NAALADase may be involved in neuronal systems regulating alcohol-drinking behavior.

In Vivo Assay of NAALADase Inhibitors on Nicotine Self-Administration in Male Long-Evans Rats Compound 3 was tested in vivo for its effect on nicotine self-administration in rats. The protocol and results are set forth in allowed U.S. patent application Ser. No. 08/899,319 for which an issue fee has been paid, the entire content of which application is herein incorporated by reference. The results show that Compound 3 reduced nicotine self-administration as well as cumulative food intakes. Although the results suggest that factors other than the NAALADase inhibitor may be responsible for the reduction in nicotine self-administration, they do not disprove NAALADase's involvement in the neuronal systems regulating nicotine use. The effect on the rats' food intake could be attributed to toxicity caused by an excessive drug dose.

Figure 23:
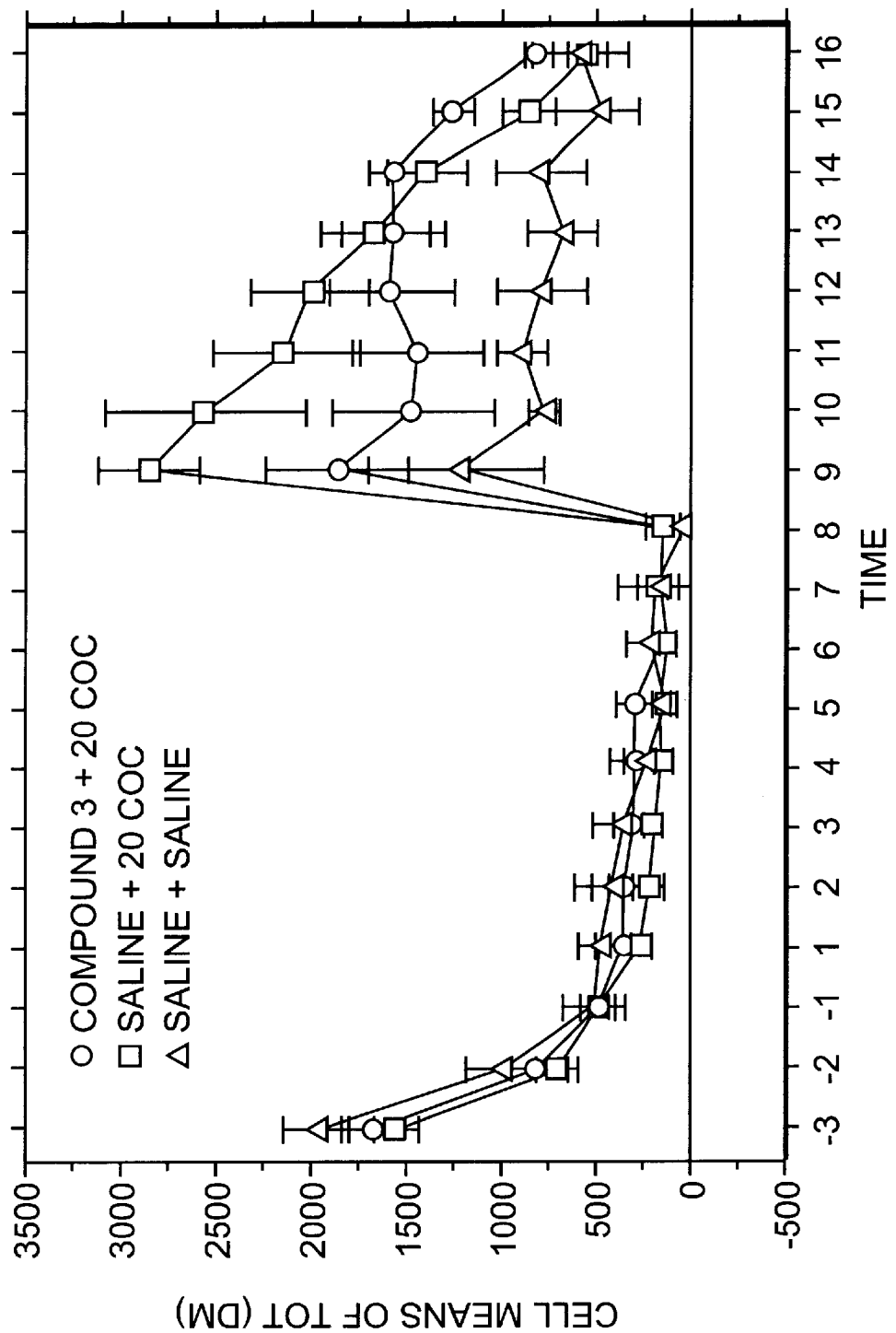
FIG. 23 is a graph plotting cocaine (20 mg/kg)-induced locomotor activity of rats against the days following treatment with Compound 3 with cocaine, saline with cocaine, and saline with saline.

In Vivo Assay of NAALADase Inhibitors on Behavioral Sensitization to Cocaine in Sprague-Dawley Rats NAALADase hydrolyzes the abundant neuropeptide NAAG to liberate glutamate (GLU). The inventors hypothesized that inhibition of NAALADase could attenuate sensitization by preventing this source of GLU. The inventors evaluated the influence of Compound 3 upon the sensitization which develops to the psychomotor stimulant effects of cocaine. Male Sprague-Dawley rats received home cage injections of cocaine (20 mg/kg/day×5 days; i.p.) or sale (1.0 ml/kg). Fifteen minutes prior to injections, they received Compound 3 at 10 and 50 mg/kg doses. Cocaine (20 mg/kg)-induced locomotor activity was assessed 3 days later. Acute cocaine increased activity of cocaine exposure (e.g. sensitization). In animals which had received Compound 3 with cocaine, the enhancement of activity was significantly reduced. Compound 3 on its own did not alter basal locomotor activity or the response to saline. The results are graphically presented in FIG. 23. The data show that Compound 3 attenuates the development of cocaine-induced sensitization. Given the postulated role of GLU in sensitization, it is suggested that NAALADase inhibitors may prevent behavioral adaptations which occur as a consequence of repeated cocaine administration.

In Vitro Assay of NAALADase Inhibitors on Cancer

Compound 3 and quisqualic acid were tested on LNCaP cells for their effect on prostate cancer. The protocol and results are set forth in U.S. Pat. No. 5,804,602, the entire contents of which are herein incorporated by reference. The results show that LNCaP cell proliferation decreased significantly as the concentration of Compound 3 and quisqualic acid increased, suggesting that NAALADase inhibitors would be effective in treating cancer, particularly prostate cancer.

Protocol for In Vitro Cancer Assay

Cells in RPMI 1640 medium containing 10% Fetal Calf Serum (FCS) are plated in 24 well plates and allowed to adhere for 24 hours before addition of quisqualic acid ($10^{-9}$ to $10^{-6}$) or Compound 3 ($10^{-11}$ to $10^{-8}$) for 7 days. On the 7th day, the cells are pulsed with 3H-thymidine for 4 hours, harvested and measured for radioactivity. Values represent means +/− SEM of 6 separate cell wells for each treatment. All experiments are performed at least twice.

To control for non-specific cytostatic effects of quisqualate acid and Compound 3, the agents are simultaneously evaluated on a non-NAALADase containing prostate cell line, DU145 (Carter et al., *Proc. Natl. Acad. Sci. USA*, (93) 749–753, 1996). If the treatments with quisqualate acid and Compound 3 have no significant effect on cell growth, the NAALADase inhibiting activity of the agents are uniquely responsible for their cytostatic effects on prostate carcinoma cell lines.

Cell Lines and Tissue Culture

LNCaP cells are obtained from Dr. William Nelson at the Johns Hopkins School of Medicine in Baltimore, MD. DU145 cells are obtained from American Type Culture Collection (Rockville, Md.). Cells are grown in RPMI-1640 media supplemented with 5% heat-inactivated fetal calf serum, 2 mm-glutamine, 100 units/ml penicillin, and 100 µg/ml streptomycin (Paragon) in a humidified incubator at 37° C. in a 5% $CO_2$/95% air atmosphere.

[3H] Thymidine Incorporation Assays

The cells are suspended at $1 \times 10^3$ cells/ml in RPMI-1640 media and seeded into 24-well plates at 500 µl per well. After 24 hour incubation, various concentrations of quisqualic acid (Sigma) or the potent NAALADase inhibitor Compound 3 (synthesized according to the methods of Jackson et al., *J. Med. Chem.*, Vol. 39, No. 2, pp. 619–622, is added to the wells and the plates are returned to the incubator. On days 3, 5 and 7, media and drug are refreshed. On the 8th day following seeding, each well is pulsed with 1 µCi $^3$H-thymidine (New England Nuclear) for 4 hours. Media is then removed and the wells washed 2 times with phosphate buffered saline (pH=7.4). The contents of each well is subsequently solubilized 250 µl of 0.2 N NaOH and transferred to scintillation vials. 5 ml UltimaGold (Packard) scintillation cocktail is added and radioactivity is quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra are obtained using a Bruker spectrometer. Chemical shifts are reported in parts per million relative to tetramethylsilane as internal standard. Analytical thin-layer chromatography (TLC) is conducted on prelayered silica gel GHLF plates (Analtech, Newark, Del.). Visualization of the plates is accomplished by using UV light, phosphomolybdic acid-ethanol, and/or iodoplatinate charring. Flash chromatography is conducted on Kieselgel 60, 230–400 mesh (E.

Merck, Darmstadt, West Germany). Solvents are either reagent or HPLC grade. Reactions are run at ambient temperature and under a nitrogen atmosphere unless otherwise noted. Solutions are evaporated under reduced pressure on a Buchi rotary evaporator.

In Vivo Assay of NAALADase Inhibitors on Cancer

To examine the effect of NAALADase inhibitors on cancer in vivo, ncr male mice injected with LNCaP cells and Copenhagan syngenic rats injected with Dunning G cells were administered subcutaneously and/or intratumorally with various doses of Compound 3. The mean tumor volume ($mm^3$) and tumor:control ratio (% T/C) following treatment are graphically presented in FIGS. 3–7.

Figure 3:
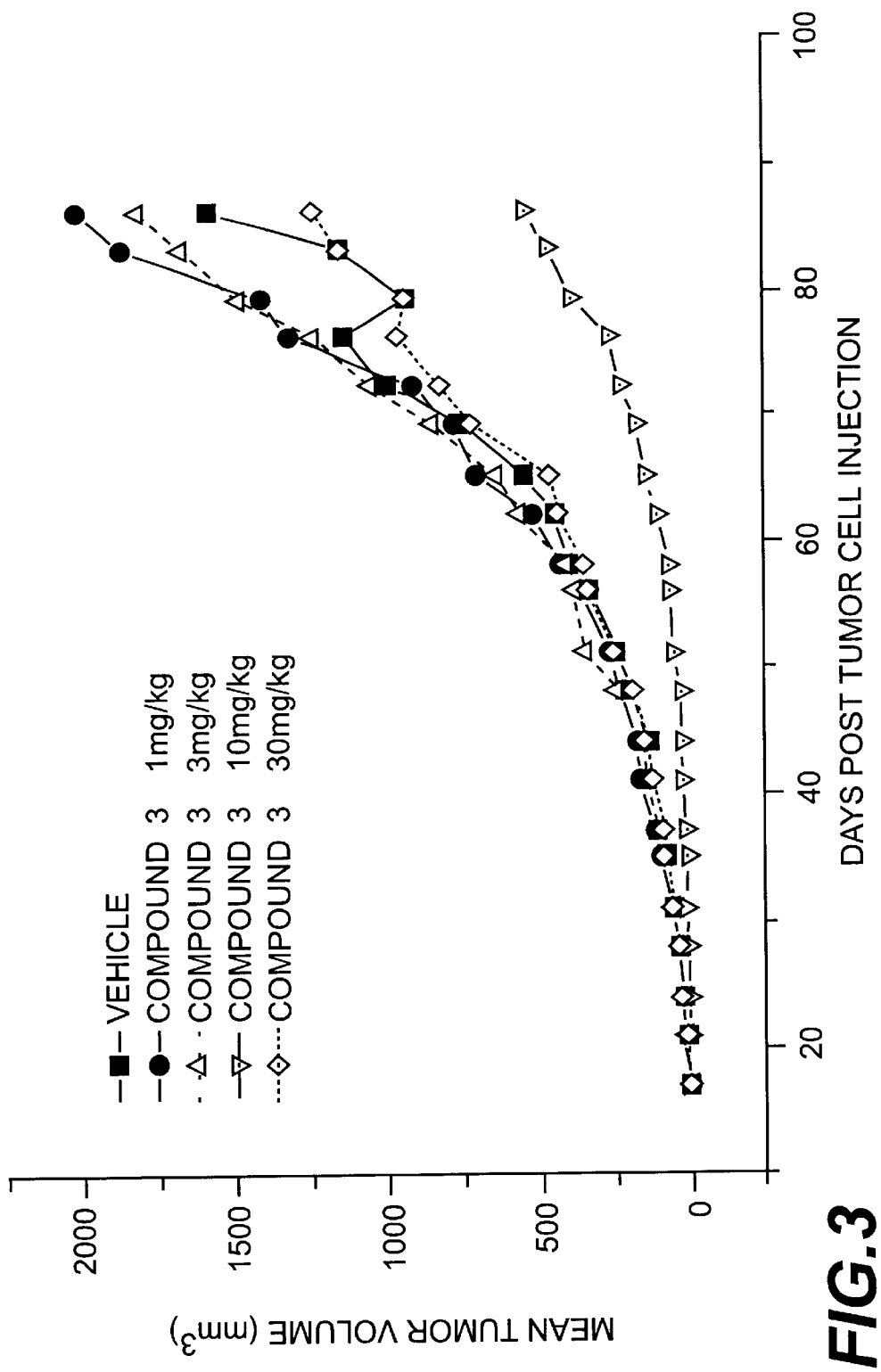
FIG. 3 is a graph plotting in vivo mean LNCaP tumor volume against the number of days following subcutaneous treatment with various doses of Compound 3.
Figure 4:
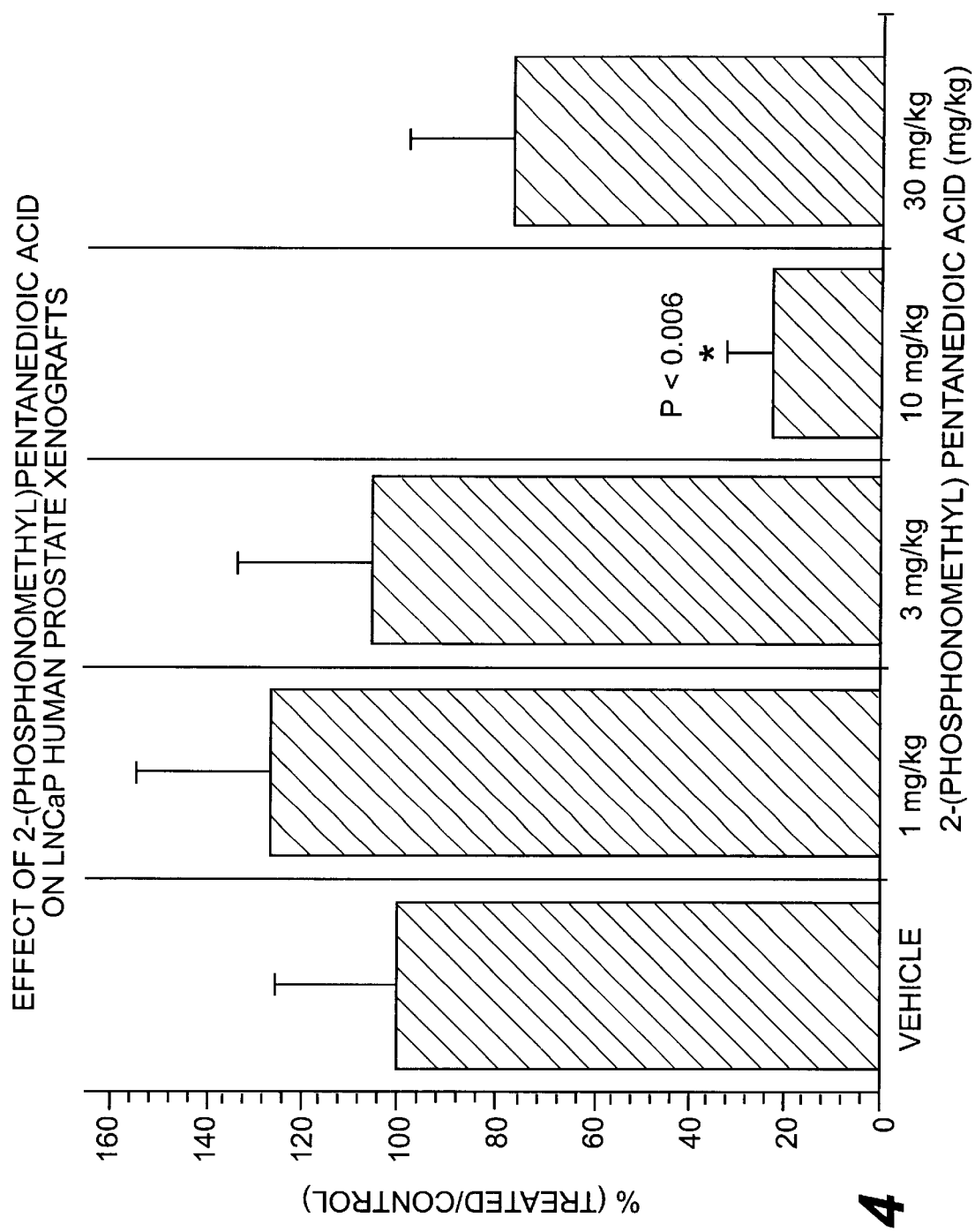
FIG. 4 is a bar graph plotting the tumor:control ratio in mice subcutaneously treated with a vehicle or Compound 3 following injection with LNCaP cells.

The results show that LNCaP tumors responded to the subcutaneous treatment with Compound 3. The lower doses of 1 and 3 mg/kg and the highest dose of 30 mg/kg apparently had no effect on tumor growth (FIG. 3). The 10 mg/kg dose significantly inhibited tumor growth to 24% of controls at day 86 (p=0.006) (FIG. 4).

Figure 5:
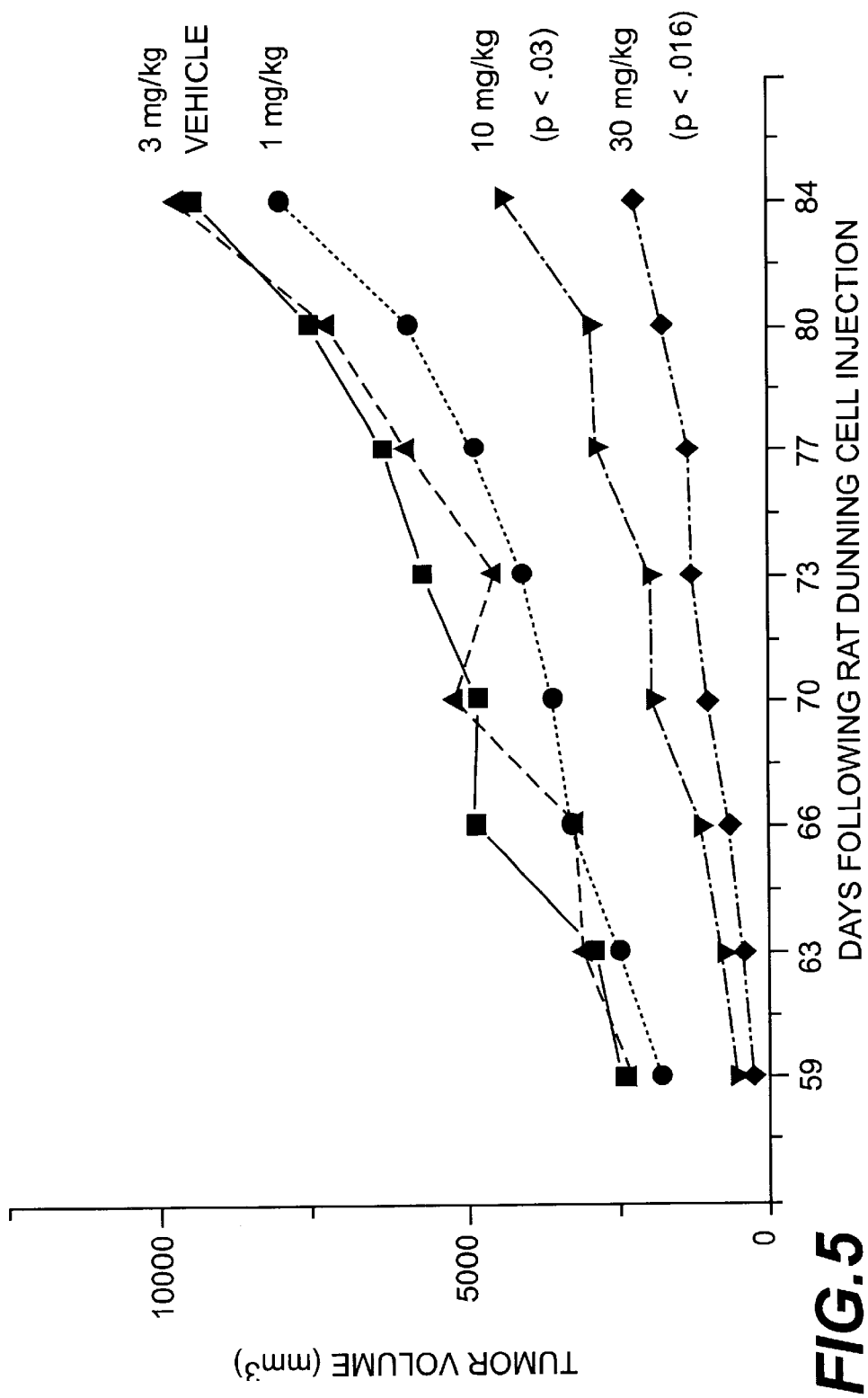
FIG. 5 is a graph plotting in vivo mean Dunning G tumor volume against the number of days following subcutaneous treatment with various doses of Compound 3.
Figure 6:
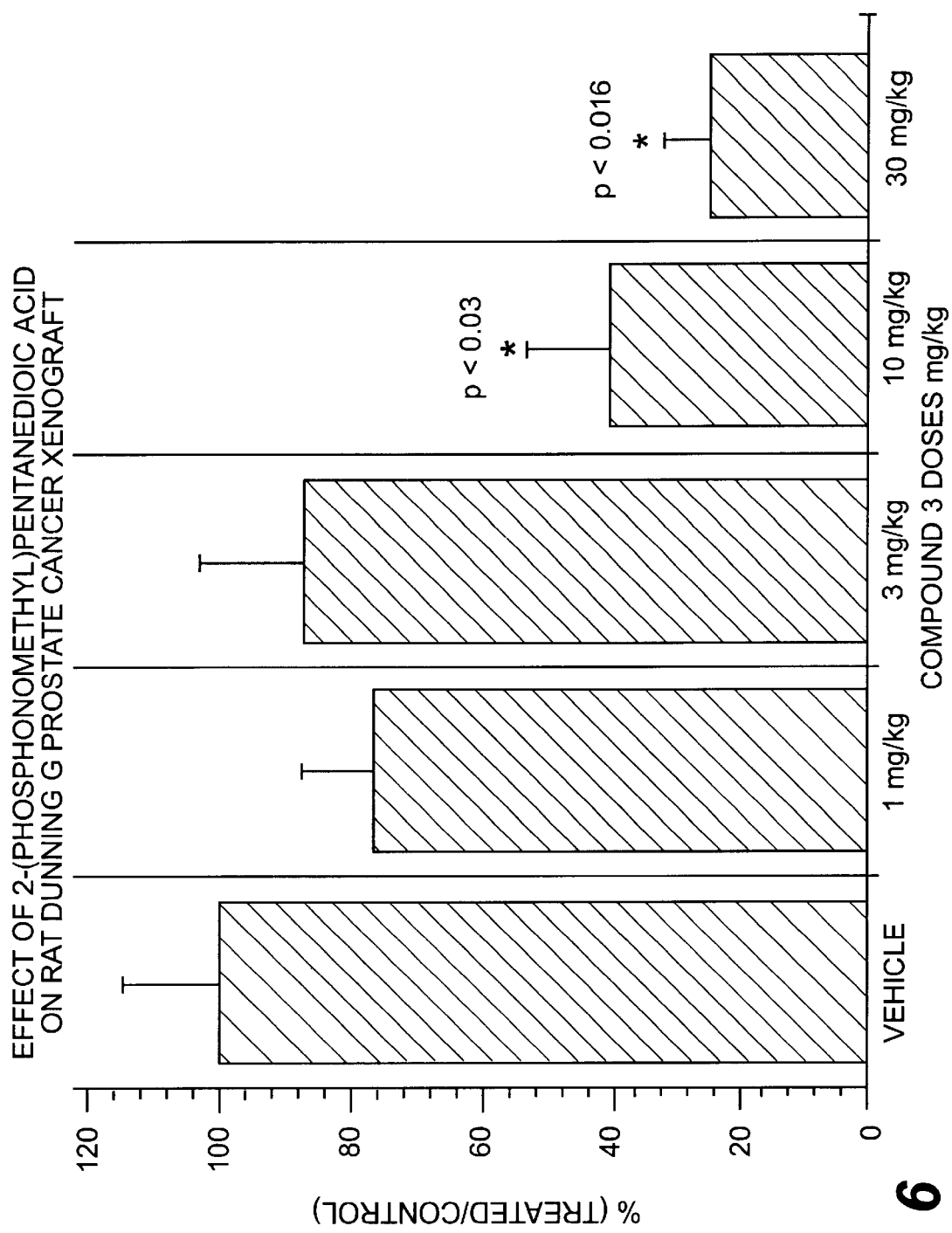
FIG. 6 is a bar graph plotting the tumor:control ratio in rats subcutaneously treated with a vehicle or Compound 3 following injection with Dunning G cells.

The Dunning G tumors also responded to the subcutaneous treatment with Compound 3. The lower doses of 1 and 3 mg/kg had no effect on tumor growth while the two higher doses, 10 and 30 g/kg, significantly decreased tumor size (FIG. 5). The tumor size decreased to 38% of controls (p=0.03) at the 10 mg/kg dose and to 22% of controls at the 30 mg/kg dose (FIG. 6).

Figure 7:
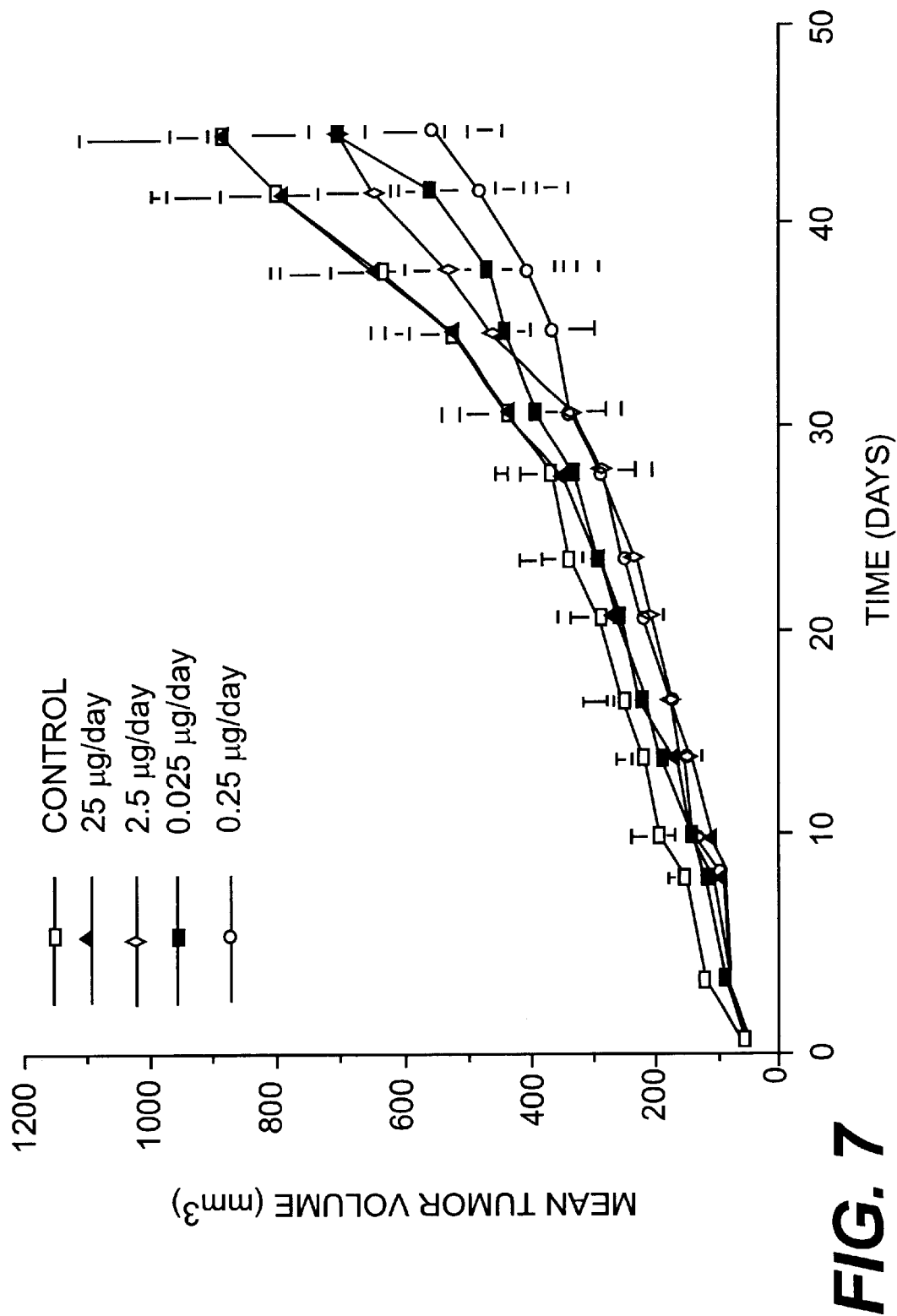
FIG. 7 is a graph plotting in vivo mean Dunning G tumor volume against the number of days following intratumoral treatment with various doses of Compound 3.

The LNCaP tumors also responded to the intratumoral treatment with Compound 3. The three lower dose levels (0.025, 0.25 and 2.5 µg/day) slowed tumor growth substantially though the greatest reduction was seen with the 0.025 µg/day dose (TABLE V). Tumor volume after 42 days of treatment in the control group was 807.3±197.3 $mm^3$ compared with 465.7±176 $mm^3$ in the group treated with 0.025 µg/day (FIG.7).

TABLE V

Antitumor Activity of Compound 3

| Treatment Group | Optimal % T/C | Regressions |
|---|---|---|
| Control | 100 | 0/7 |
| Intratumoral | | |
| Compound 3 | | |
| 25.0 µg/day | 76 | 0/7 |
| 2.5 µg/day | 45 | 0/7 |
| 0.25 µg/day | 51 | 1/7 |
| 0.025 µg/day | 42 | 1/7 |

Protocol for In Vivo Cancer Assay
Subcutaneous drug delivery
LNCaP MODEL (Compound 3):

Ncr nude male mice, age 5 to 6 weeks, were injected in the right flank with $5 \times 10^6$ LNCaP cells in Matrigel™ (0.1 ml total injection volume). Two weeks following cell injection, daily subcutaneous (s.c.) injections of Compound 3 were initiated at the following doses: 1, 3, 10 and 30 mg/kg. Controls received 50 mM HEPES s.c. daily. Once tumors were palpable they were measured twice a week.

DUNNING G MODEL (Compound 3):

Male Copenhagen syngenic rats, age 8 to 10 weeks, were injected in both flanks with $10^7$ Dunning G cells. Two weeks following cell injection, daily s.c. injections of Compound 3 were initiated at the following doses: 1, 3, 10 and 30 mg/kg. Controls received 50 mM HEPES s.c. daily. Tumors were measured twice a week.

Intratumoral drug delivery:
LNCaP MODEL (Compound 3):

Ncr nude male mice, age 5 to 6 weeks, were injected in the right flank with $10^7$ LNCaP cells in Matrigel™ (0.1 ml total injection volume). When the tumors reached a predetermined size (50 to 60 $mm^3$) mice were randomly placed into treatment groups of 6 to 8 mice each. Compound 3 was administered intratumorally daily in a volume of 0.05 ml in the following doses: 25, 2.5, 0.25 and 0.025 µg. Controls received 50 µl of 50 mM HEPES intratumorally daily. Tumors were measured twice a week.

Response to treatment was monitored in two ways. First, mean tumor volume for each group was presented as tumor: control ratio (% T/C) and these values were compared at one point in time. Second, tumor volume versus time was monitored.

In Vivo Assay of Daily Dosages of NAALADase Inhibitors on Angiogenesis

C57B1 female mice age 8 to 10 weeks (5/group) were injected subcutaneously with 0.5 mL of Matrigel™, 150 ng/mL of the angiogenic factor basic FGF (bFGF) and with 0, 0.47 µM or 4.7 µM Compound 3. The injected Matrigel™ rapidly formed a gel. On the same a day as the Matrigel™ injection, daily subcutaneous injections of Compound 3 around the Matrigel™ plug were initiated. Seven days post Matrigel™ injection, Matrigel™ plugs were excised and histology was performed.

The concentrations of the daily dosages as well as the coinciding initial Matrigel™ plug compositions are provided below in TABLE VI.

TABLE VI

Concentrations of Daily Dosages of NAALADase Inhibitors

| Daily Subcutaneous Injection Concentration | Initial Concentrations in Matrigel ™ |
|---|---|
| Vehicle | 50 mM Hepes |
| 3 mg/kg | 0.47 µM Compound 3 in 50 mM Hepes |
| 30 mg/kg | 4.7 µM Compound 3 in 50 mM Hepes |

Figure 8A:
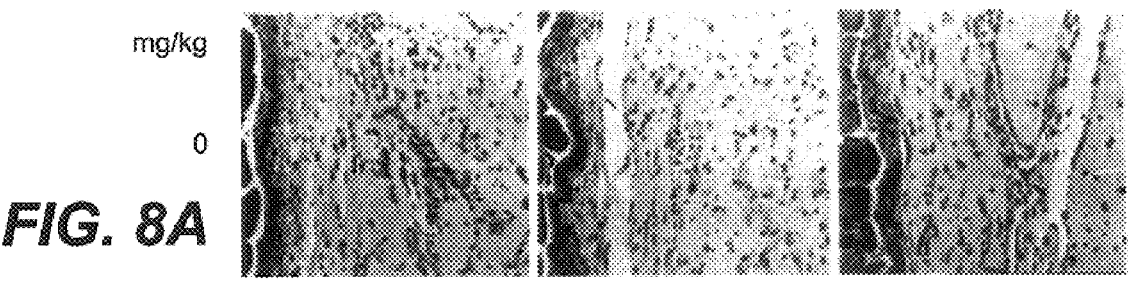
FIG. 8A is a set of microphotographs of Matrigel™ plugs subcutaneously injected into mice and treated with a vehicle alone following injection of an angiogenic factor.
Figure 8B:
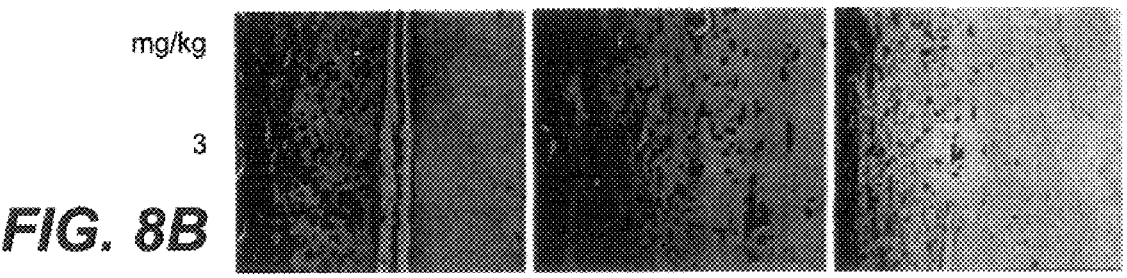
FIG. 8B is a set of microphotographs of Matrigel™ plugs subcutaneously injected into mice and treated with daily 3 mg/kg dosages of Compound 3 following injection of an angiogenic factor.
Figure 8C:
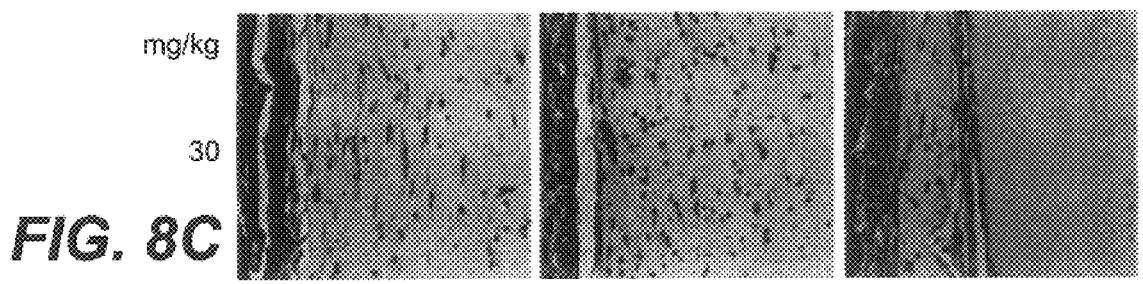
FIG. 8C is a set of microphotographs of Matrigel™ plugs subcutaneously injected into mice and treated with daily 30 mg/kg dosages of Compound 3 following injection of an angiogenic factor.

As detailed in FIG. 8A, a good angiogenic response was observed in the vehicle dose group. The resultant decrease in blood vessels or angiogenesis in the Matrigel™ plugs from the 3 mg/kg and 30 mg/kg daily dose groups is shown in FIG. 8B and FIG. 8C, respectively.

In Vivo Assay of a Continuous Dosage of NAALADase Inhibitors on Angiogenesis

Miniosmotic pumps were implanted into C57B1 female mice (5/group) at the Compound 3 concentrations shown in TABLE VII below. Minipumps filled with vehicle (50 mM Hepes) were also implanted at this time. Twenty-four hours later, mice were each injected subcutaneously with 0.5 mL Matrigel™ and the 150 ng/mL of the angiogenic factor, basic FGF (bFGF). Thirteen days post Matrigel™/bFGF injection, the gels were recovered, fixed in formalin and sections were stained with Trichrome-Masson stain.

TABLE VII

Concentrations of Continuously Administered
NAALADase Inhibitors

Compound 3 Released by Minipump 50 mM Hepes
1 µg/day
10 µg/day
100 µg/day

Figure 9:
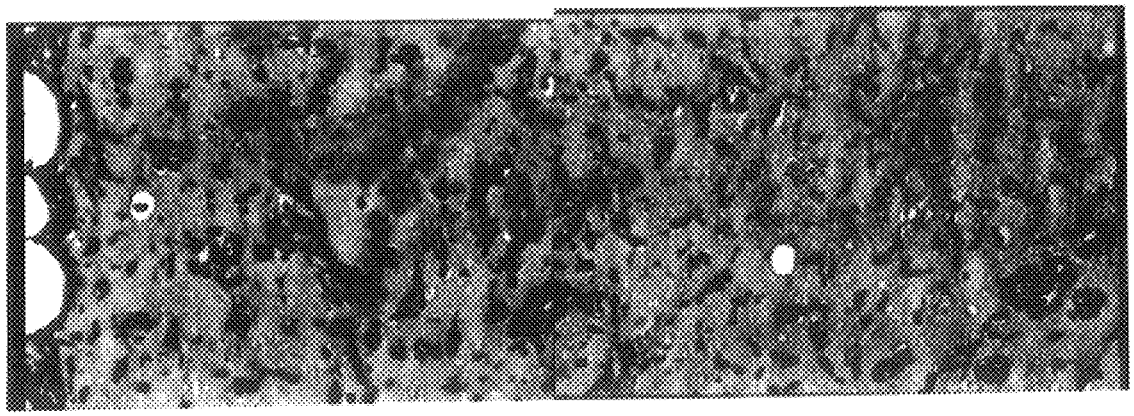
FIG. 9 is a microphotograph of a Matrigel™ plug subcutaneously injected into a mouse and treated with a continuous concentration dosage of a vehicle alone following injection of an angiogenic factor.
Figure 10:
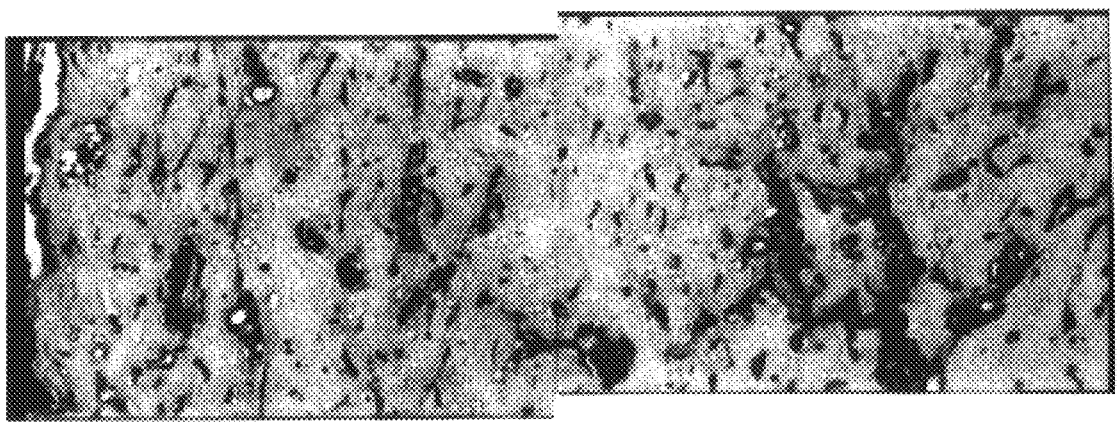
FIG. 10 is a microphotograph of a Matrigel™ plug subcutaneously injected into a mouse and treated with a 1 µg/day continuous dosage of Compound 3 following injection of an angiogenic factor.
Figure 11:
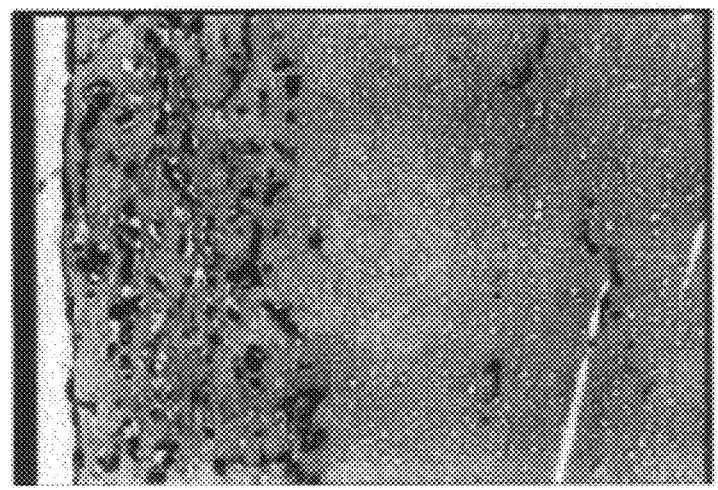
FIG. 11 is a microphotograph of a Matrigel™ plug subcutaneously injected into a mouse and treated with a 10 µg/day continuous dosage of Compound 3 following injection of an angiogenic factor.
Figure 12:
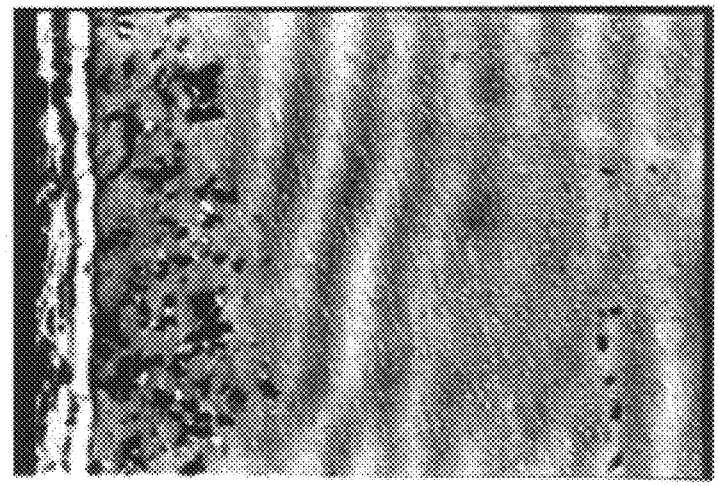
FIG. 12 is a microphotograph of a Matrigel™ plug subcutaneously injected into a mouse and treated with a 100 µg/day continuous dosage of Compound 3 following injection of an angiogenic factor.

A strong angiogenic response was observed in the vehicle and 1 µg/day dose group, as shown in FIG. 9 and 10, respectively. As detailed in FIG. 11 and 12, respectively, delivery of 10 µg/day and 100 µg/day of Compound 3 significantly decreased angiogenesis in the Matrigel™/bFGF gels.

In Vivo Assay of NAALADase Inhibitors on Diabetic Neuropathy

NAALADase inhibition in an in vivo streptozotocin (STZ)-induced peripheral diabetic neuropathy model was studied. Male Sprague-Dawley rats weighing 200–250 g were rendered diabetic by intravenous injection of 60 mg/kg STZ into the tail vein. Plasma glucose levels were determined 3 weeks after STZ administration. Only STZ-animals with plasma glucose levels>300 mg/dL (17 mM) were used in the study. Thermal pain threshold and withdrawal latency were used to assess the status of the small dorsal root ganglion (DRG) sensory neurons. Pain was monitored using the plantar test (Hargreaves' Method) using a Basile Plantar apparatus built by Ugo Basil, Vaarese, Italy.

Figure 13:
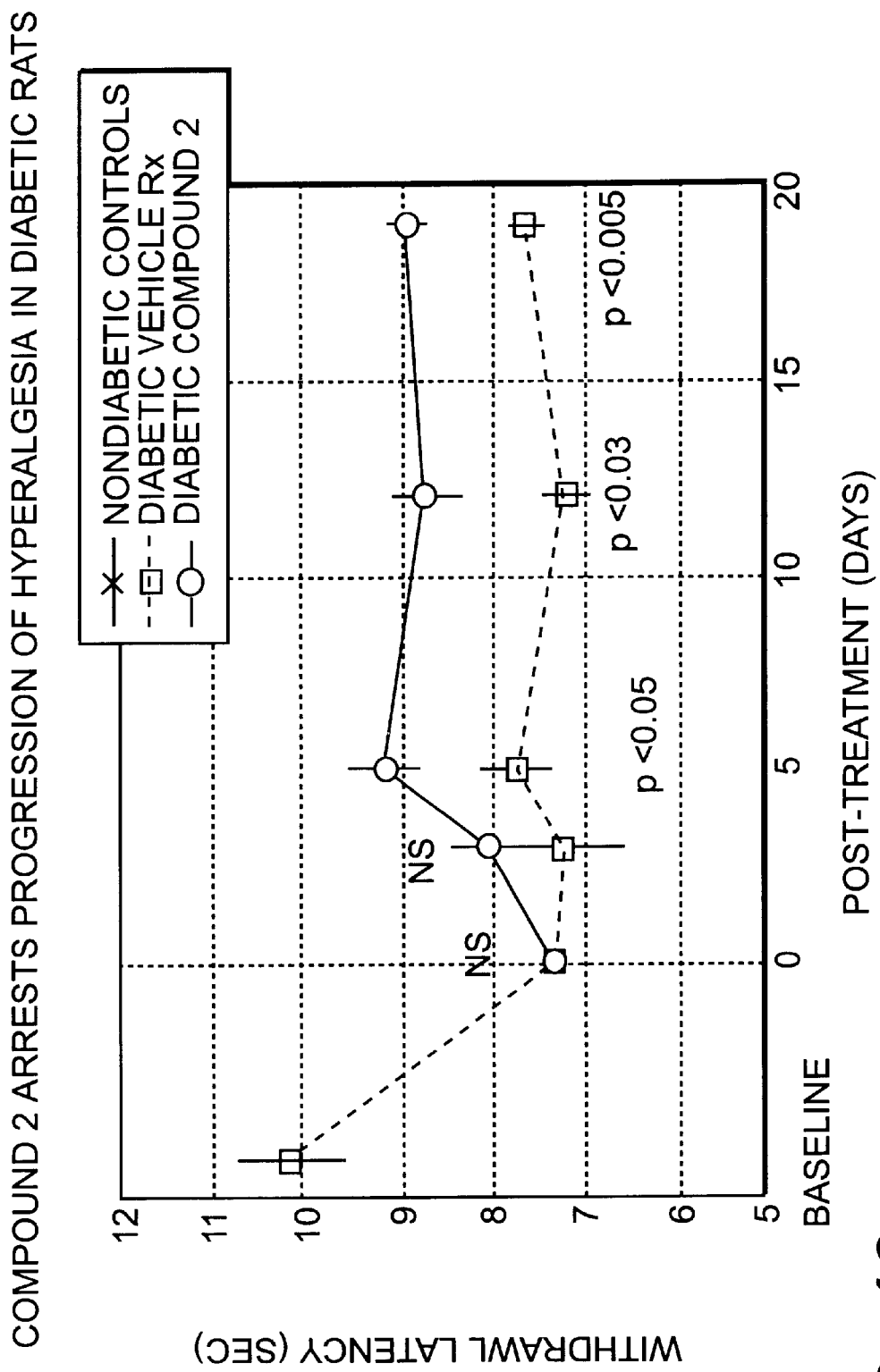
FIG. 13 is a graph plotting withdrawal latency of diabetic rats against the days following treatment with Compound 2.

At two months following the STZ administration, the diabetic animals were hyperalgesic as compared to non-diabetic controls as determined by their difference in withdrawal latency. At this time, the rats were administered either the NAALADase inhibitor Compound 2 (50 mg/kg) or vehicle intraperitoneally once per day for 20 days. Thermal pain responses were measured at days 3, 5, 12 and 19 post-dosing. As depicted in FIG. 13, following 5 days of dosing, animals administered Compound 2 showed a significant increase in their withdrawal latency compared to vehicle animals. This difference was maintained throughout the observation period.

These data suggest that NAALADase inhibitors protect against experimental diabetic sensory neuropathy and may be useful in the treatment of peripheral neuropathies.

Figure 14:
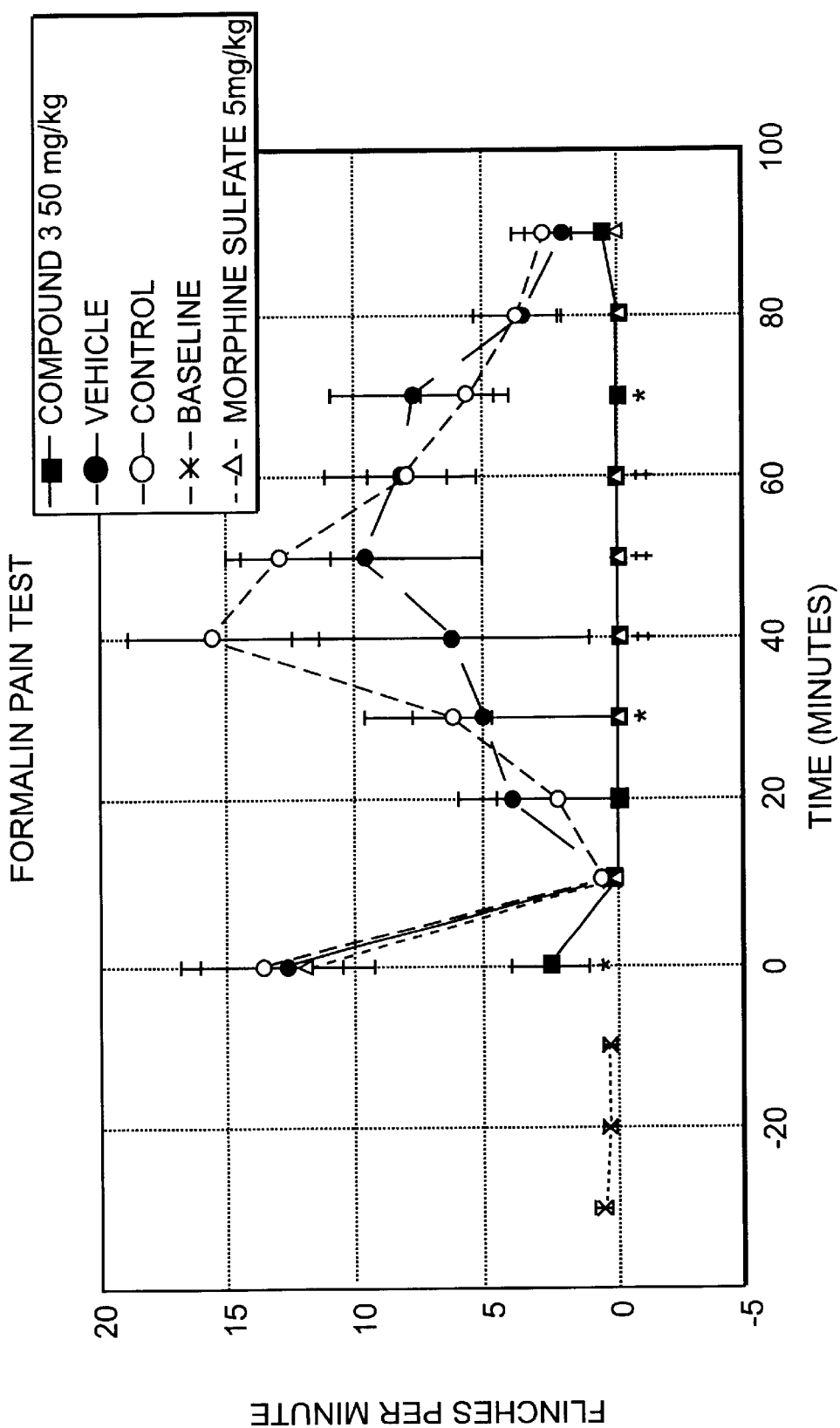
FIG. 14 is a graph plotting the formalin-induced flinching behavior of rats treated with a vehicle or Compound 3 against the time following treatment.
Figure 15:
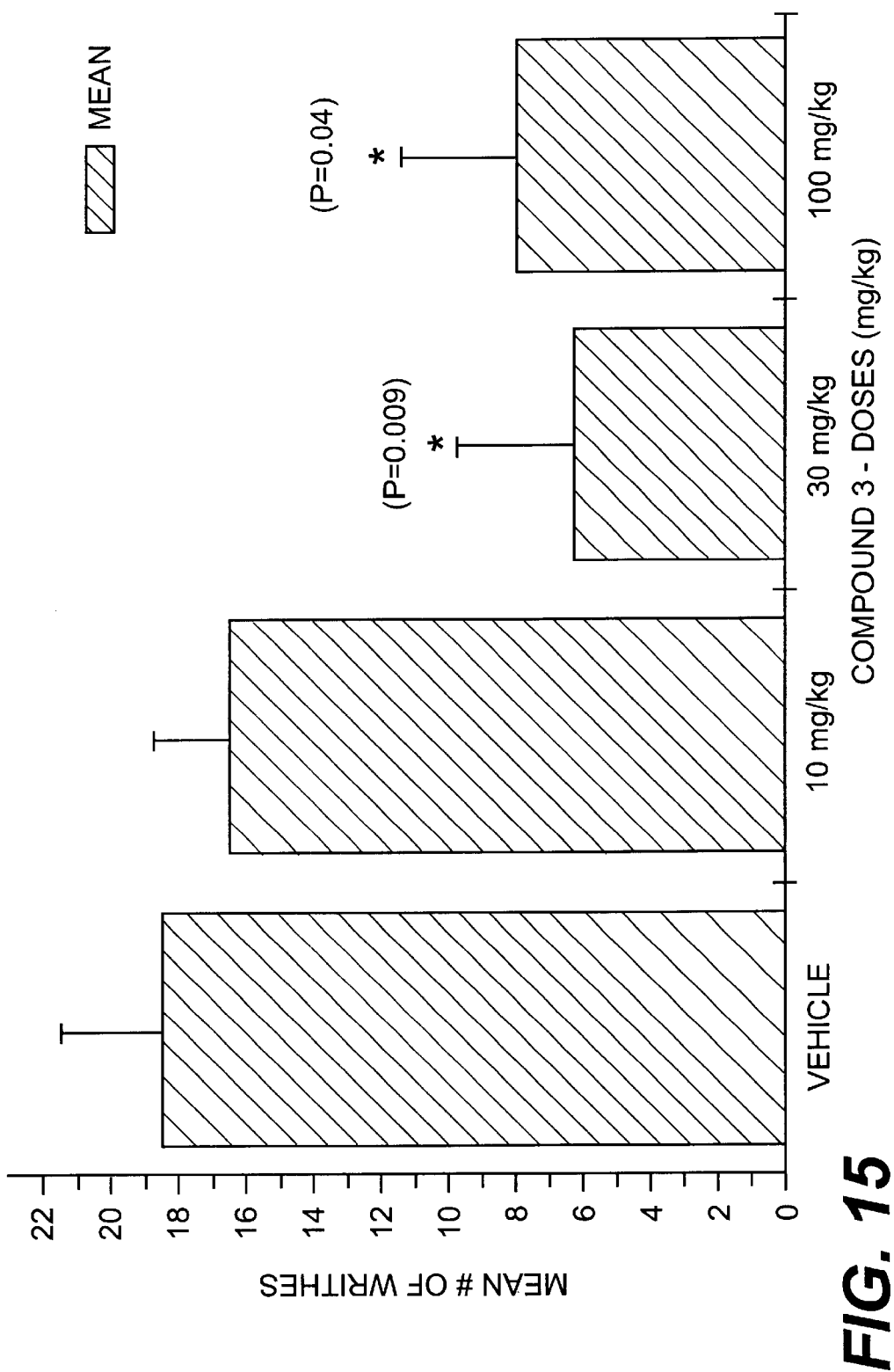
FIG. 15 is a bar graph plotting the acetic acid-induced writhing of rats against doses of a vehicle or Compound 3 with which the rats were treated.
Figure 16:
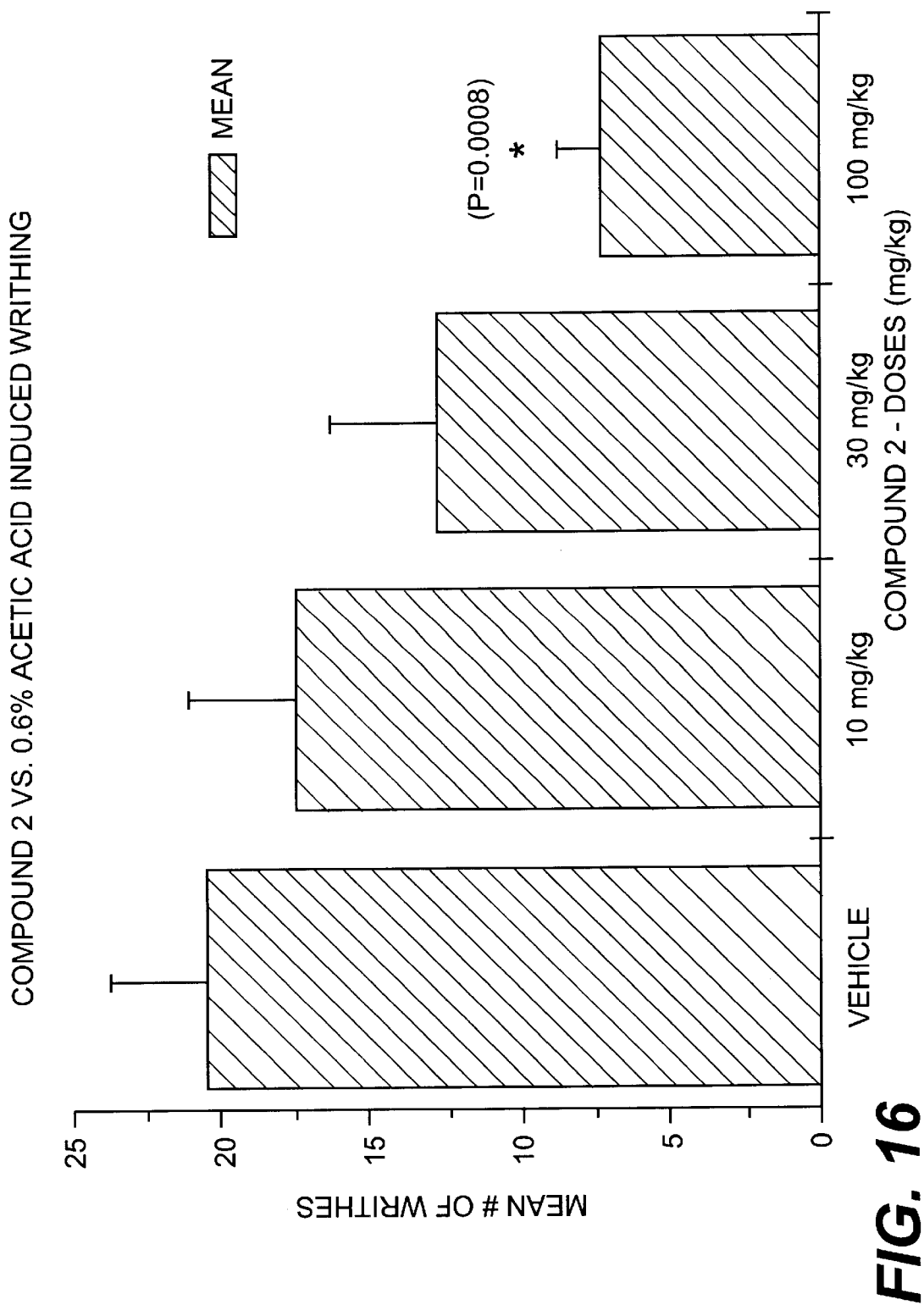
FIG. 16 is a bar graph plotting the acetic acid-induced writhing of rats against doses of a vehicle or Compound 2 with which the rats were treated.
Figure 17:
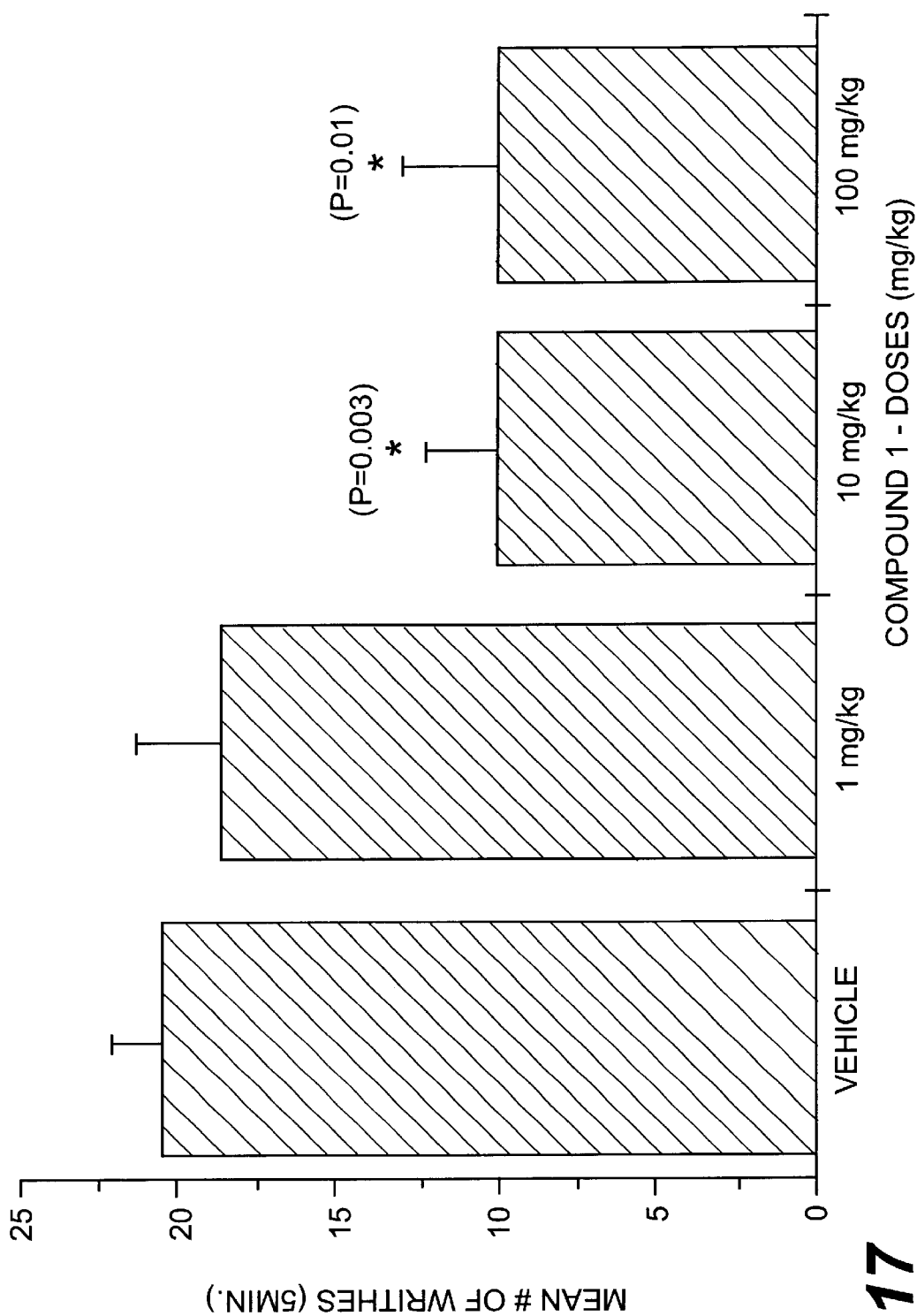
FIG. 17 is a bar graph plotting the acetic acid-induced writhing of rats against doses of a vehicle or Compound 1 with which the rats were treated.
Figure 18:
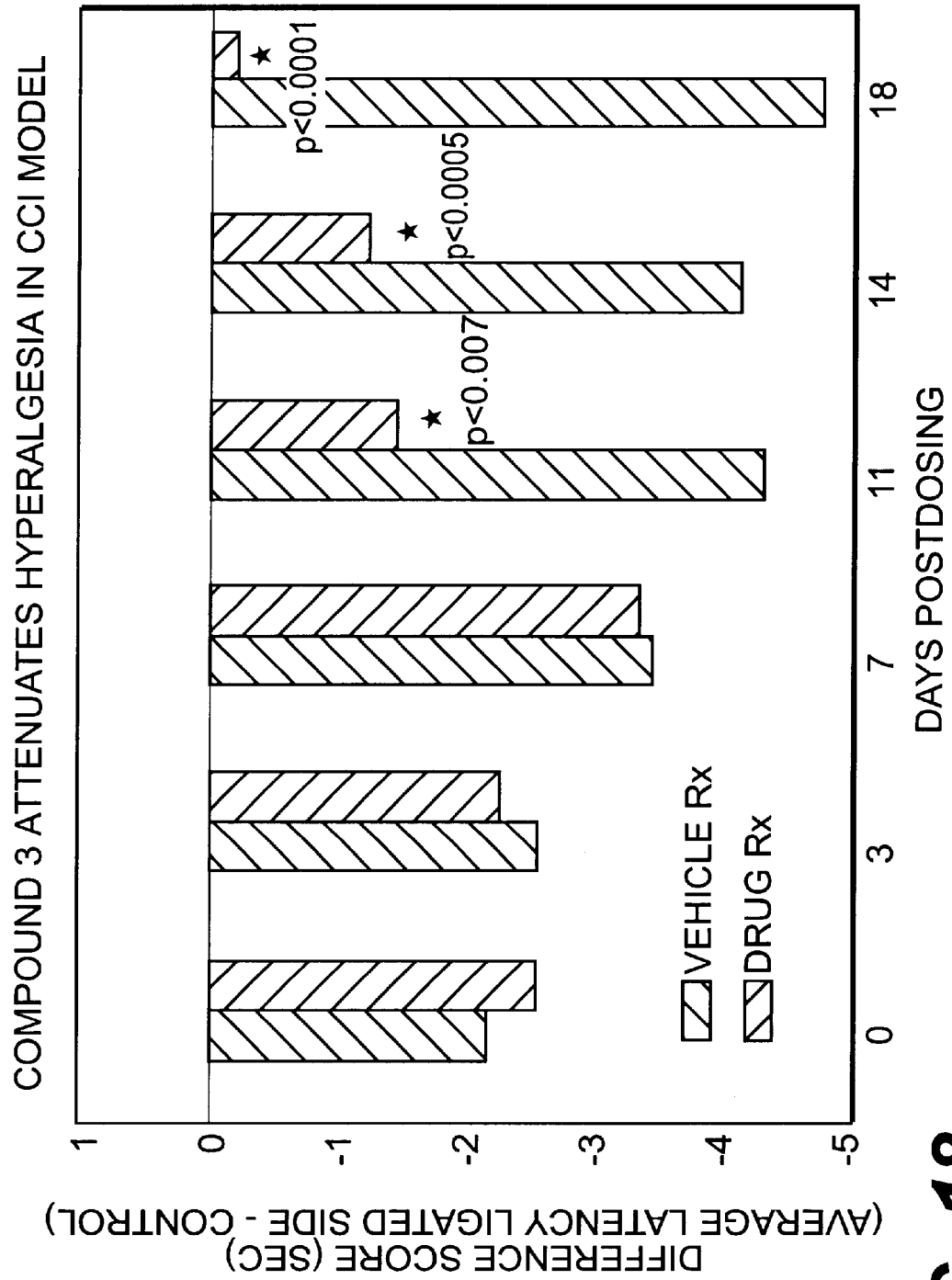
FIG. 18 is a bar graph plotting the chronic constrictive injury-induced hyperalgesia of rats treated a vehicle or Compound 3 against the days postdosing.
Figure 19A:
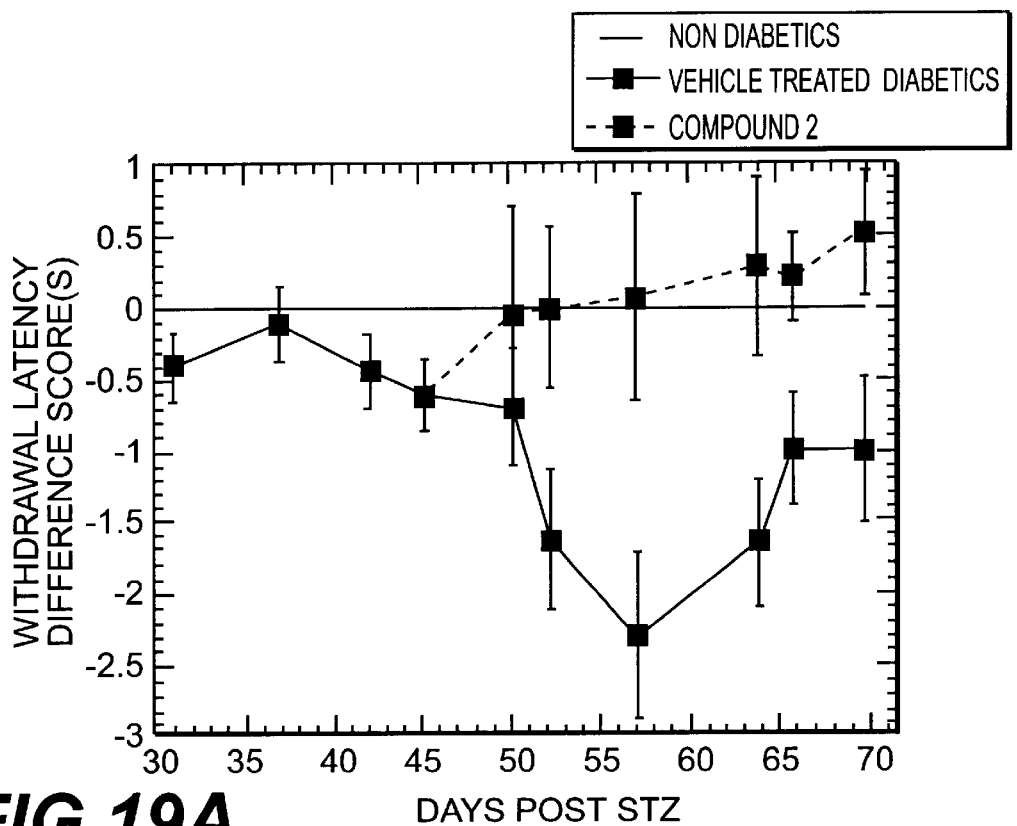
FIG. 19A is a bar graph plotting the withdrawal latency difference scores of non-diabetic rats STZ-diabetic rats treated with a vehicle or Compound 2, against the days following administration with STZ.
Figure 19B:
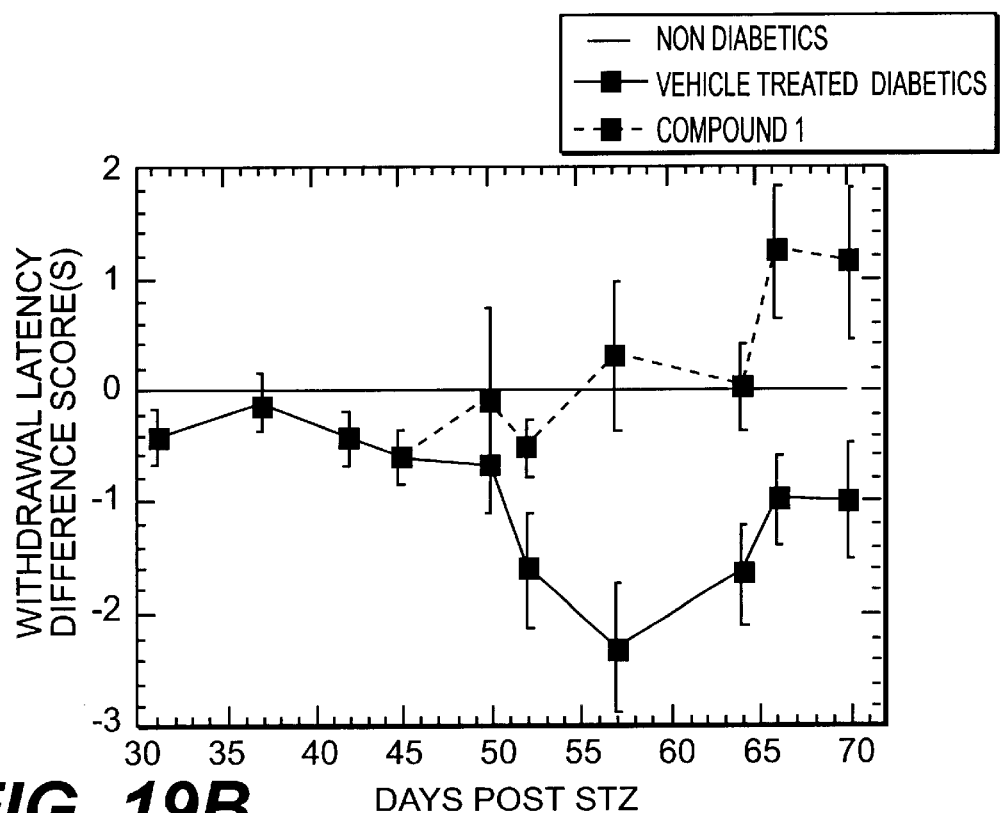
FIG. 19B is a bar graph plotting the withdrawal latency difference scores of non-diabetic rats STZ-diabetic rats treated with a vehicle or Compound 1, against the days following administration with STZ.

In Vivo Assay of NAALADase Inhibitors on Hyperalgesia in Formalin, Acetic Acid, and Chronic Constricture Induced (CCI) Models of Pain Recent evidence suggest that the excitatory amino acid glutamate plays a major role in both centrally and peripherally mediated nociception. One source of neuronal glutamate is thought to derive from the abundant neuropeptide NAAG which is hydrolyzed by NAALADase to liberate free glutamate. The inventors hypothesized that inhibition of NAALADase could limit pain by preventing this source of glutamate. To test this hypothesis, the inventors examined the possible antinocipetive effects of several NAALADase inhibitors in the formalin-, acetic acid- and chronic constrictive injury (CCI; "Bennett model") models of pain. In the formalin model, rats were dosed i.p. daily with Compound 3 (50 mg/kg) or vehicle for 7 days. On day 7, 5% formalin was injected into the dorsum of the rat's hindpaw. The results are graphically presented in FIGS. 14–19. Pretreatment with Compound 3 robustly attenuated the flinching behavior in both the early and late phases of the formalin model (13.8±6.4 reduced to 2.5±3, p=0.02 and 58.0±9.8 reduced to 0.5±0.58, p=0.0001, respectively; FIG. 14). The Compound 3 treatment was more robust than acute pretreatment with morphine (5 mg/kg). In the acetic acid model of pain, acetic acid (0.6%) induced writhing was significantly attenuated in mice pretreated with Compound 3 (FIG. 15), Compound 2 (FIG. 16), Compound 1 (FIG. 17), compared to vehicle control animals. Finally, in the CCI induced model of pain, animals were dosed i.p. daily with Compound 3 (50 mg/kg) starting 10 days after surgery for 18 days. Compound 3 dramatically reduced the hyperalgesia following sciatic nerve constriction as determined by thermal pain response. On day 18, pain was 98% attenuated when compared to a similarly operated vehicle group of rats (difference scores of −0.2±1.9 vs. −4.75±2.4; p=0.0001; FIG. 18). These data suggest that inhibition of NAALADase may be a useful treatment modality for both acute and chronic pain.

In Vivo Assay of NAALADase Inhibitors on Neuropathic Pain

Male Sprague-Dawley rats (200–225 g) were rendered diabetic by intravenous administration of streptozotocin (STZ, 70 mg/kg in phosphate buffered saline). Diabetic animals were divided into five groups: one group receiving Compound 2 (10 mg/kg or 1 mg/kg), Compound 1 (10 mg/kg or 1 mg/kg) or vehicle. Another group of animals (non-STZ treated) served as non-diabetic controls. Drug/vehicle treatment was started in diabetic animals 45 days post-STZ administration. STZ-induced diabetic rats were tested for sensitivity to a heat source as soon as blood glucose levels rose to 320 mg/dl or above (30 days post STZ). The rats were then acclimated to the Hargreaves apparatus and thermal nociception was monitored using an infrared heat source directed into the dorsal surface of the hindpaw, and the time taken for the animal to remove its paw noted to the nearest 0.1 seconds (see Hargreaves et al. 1998 for detailed method). The intensity of the beam source was adjusted such that the mean latency for control animals (non-STZ treated) was approximately 10 seconds. Each animal was tested 8 times and the mean difference score (between mean non-diabetic control latency and mean diabetic latency) are graphically presented in FIGS. 19A and 19B. Diabetic rats displayed a hyperalgesia (shorter response latency) compared to non-diabetic controls, starting 30 days post STZ treatment and progressively worsening in vehicle treated rats. This hyperalgesic response was completely reversed in diabetic rats receiving treatment with Compound 1 or 2 (10 mg/kg i.p. daily). Thus, the results show that NAALADase inhibition attenuates neuropathic pain.

In Vivo Assay of NAALADase Inhibitors on Progression of Neuropathic Pain

Compound 3

Figure 20:
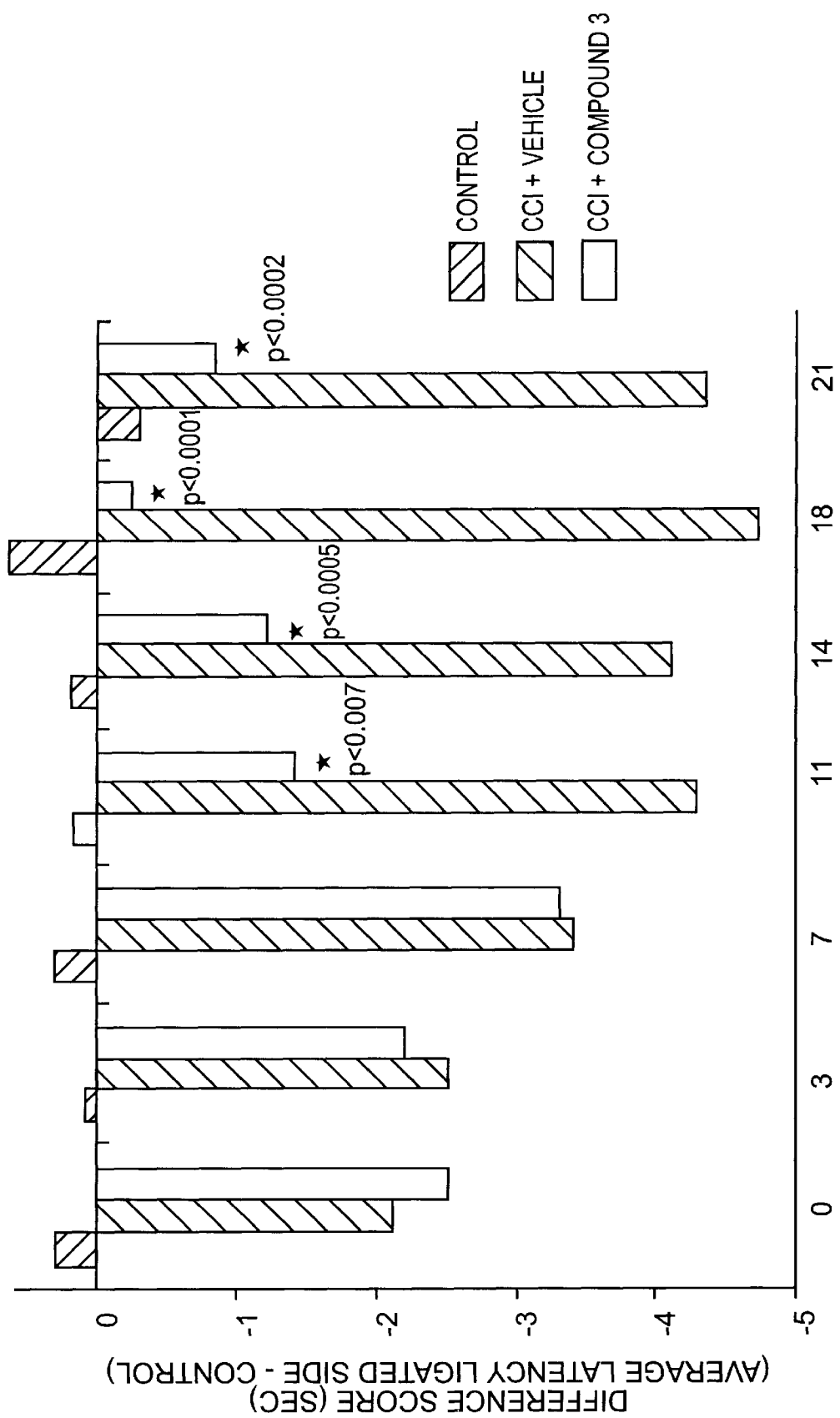
FIG. 20 is a bar graph plotting the withdrawal latency difference scores of normal (unoperated) rats and chronic constrictive injury-induced rats treated with a vehicle or Compound 3, against the days following surgery.
Figure 21A:
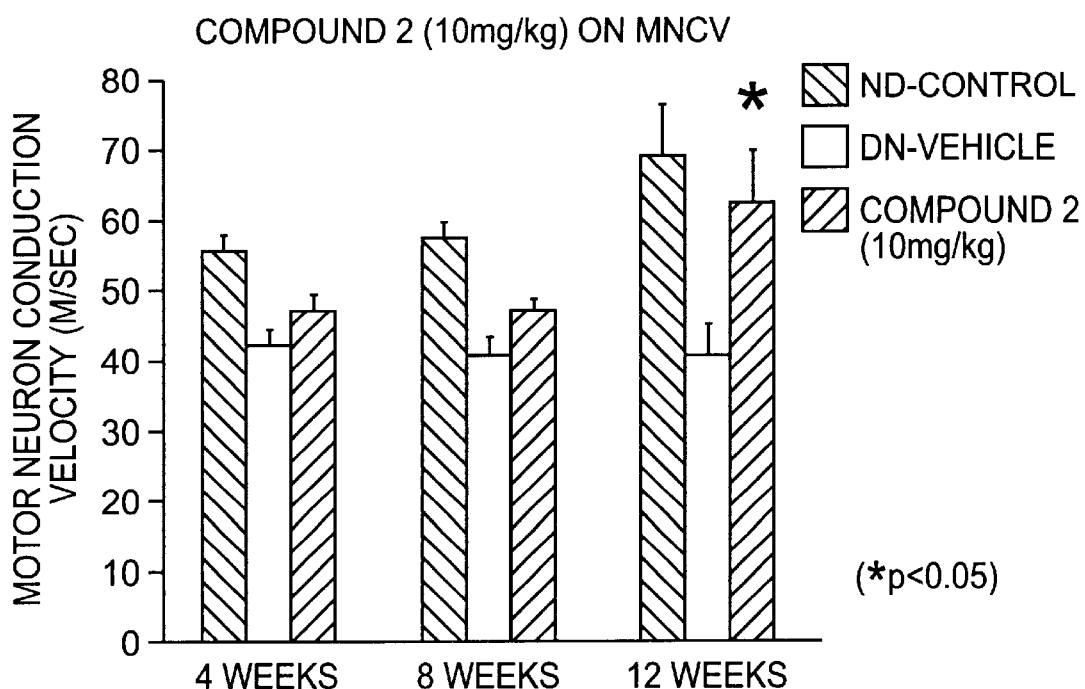
FIG. 21A is a bar graph plotting the motor neuron conduction velocity of non-diabetic rats and STZ-diabetic rats treated with a vehicle or Compound 2, against the days following administration with STZ.
Figure 21B:
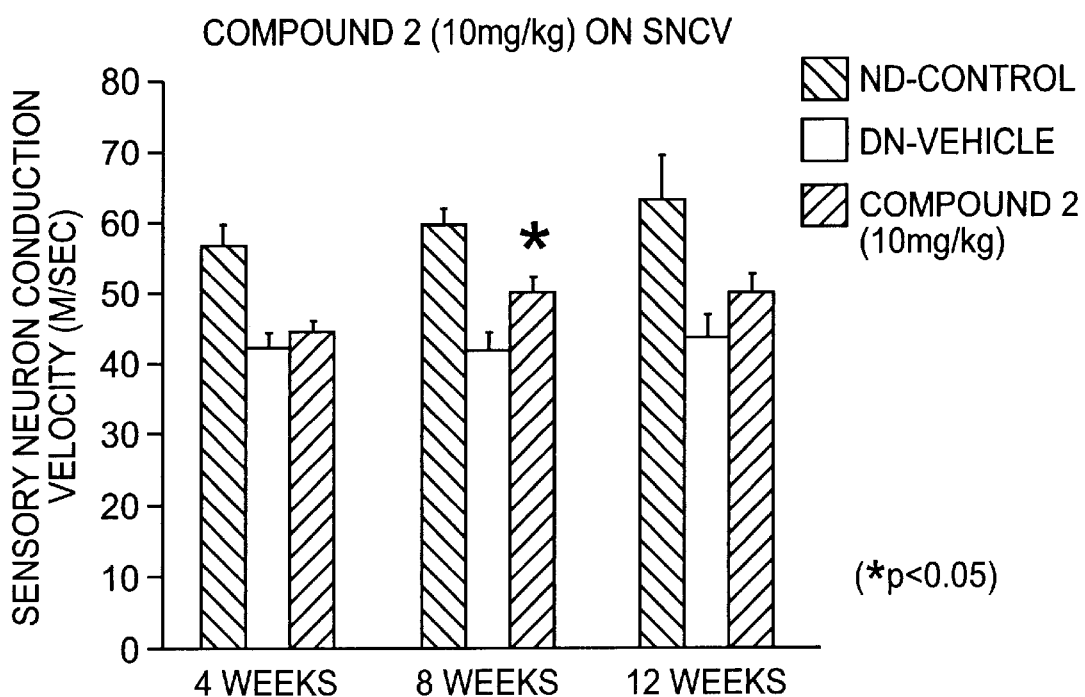
FIG. 21B is a bar graph plotting the sensory neuron conduction velocity of non-diabetic rats and STZ-diabetic rats treated with a vehicle or Compound 2, against the days following administration with STZ.
Figure 22A:
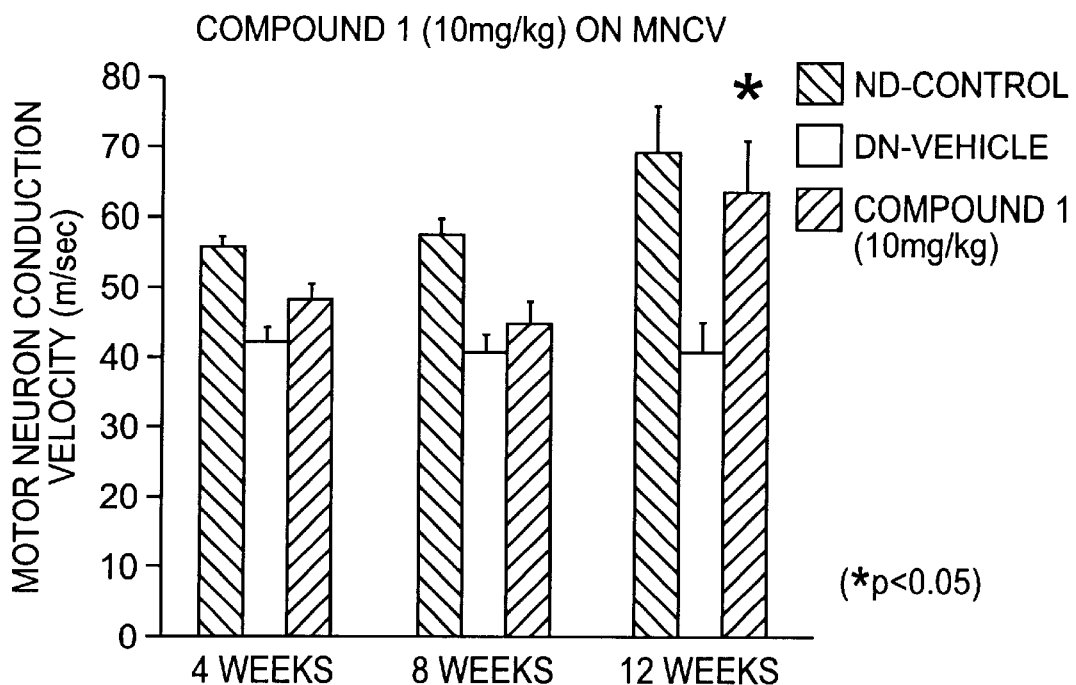
FIG. 22A is a bar graph plotting the motor neuron conduction velocity of non-diabetic rats and STZ-diabetic rats treated with a vehicle or Compound 1, against the days following administration with STZ.
Figure 22B:
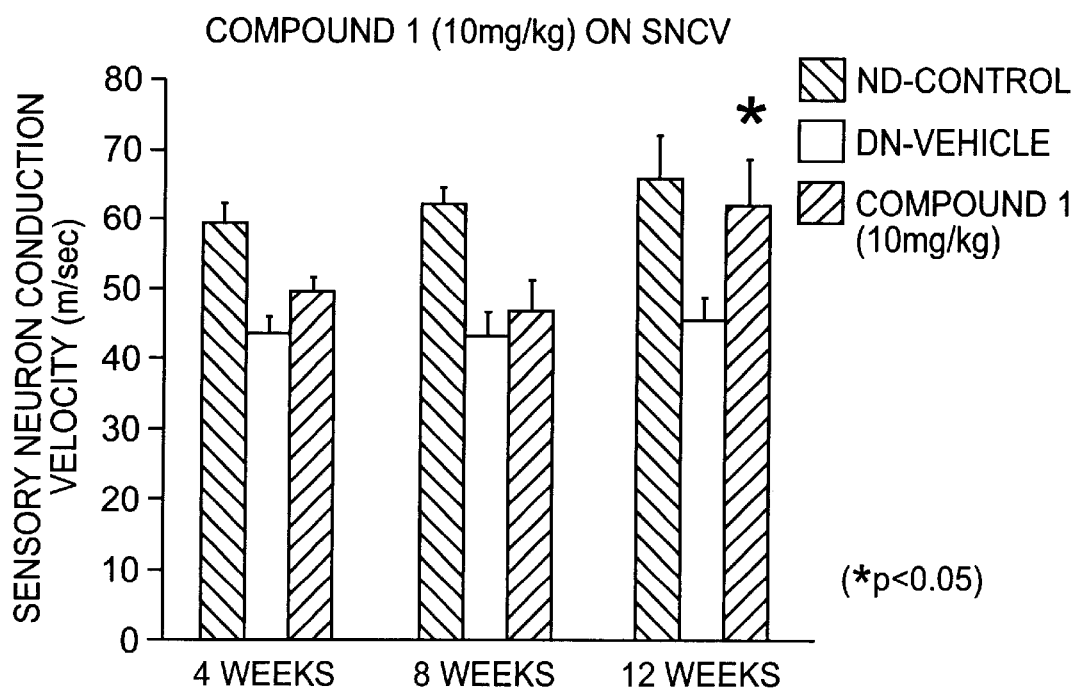
FIG. 22B is a bar graph plotting the sensory neuron conduction velocity of non-diabetic rats and STZ-diabetic rats treated with a vehicle or Compound 1, against the days following administration with STZ.

Sciatic nerve ligation, consisting of 4 ligatures being tied loosely around the sciatic nerve at 1 mm intervals proximal to the nerve trifurcation, was performed on rats. Following this treatment, rats exhibit a thermal hyperalgesia and allodynia. Animals were habituated to the Hargreaves apparatus and the infrared heat source directed onto the dorsal surface of the hindpaw and the time taken for the animal to withdraw its paw noted. The difference score (between the latency of the response for the paw on the operated side versus the control side) was determined. Animals received Compound 3 (50 mg/kg i.p. daily) or vehicle, starting 10 days post surgery. Treatment with Compound 3 dramatically normalized the difference scores between the two paws compared to the continued hyperalgesic vehicle-treated controls. Normal (unoperated) rats had approximately equal latencies for both paws. This effect was significant starting at 11 days of drug treatment and persisted through to the end of the study (for 21 days of daily dosing). The difference scores are graphically presented in FIG. 20. The results show that NAALADase inhibition attenuates CCI-associated hyperalgesia.

Compounds 1 and 2

Male BB/W rats (BRI, Mass) spontaneously develop a cell mediated autoimmune destruction of pancreatic B cells, resulting in onset of insulin-dependent (Type I) diabetes (Guberski 1994). These rats have been characterized and shown to demonstrate neuropathies with accompanying neural deficits such as fiber loss and degeneration, changes which are correlative with those seen in peripheral nerve of human diabetic patients (Yagihasi 1997). This renders them valuable for experimental trials of new compounds for future treatments of this major disorder. In the present study, Compound 1 and Compound 2 were examined for their ability to alter the progression of diabetic neuropathy. The rats received daily injection of Compound 1 or Compound 2 (10 mg/kg i.p.) or vehicle, starting at the onset of diabetes (hyperglycemia) and up to 6 months thereafter. Another group of non-diabetic rats also receiving vehicle were tested. All animals were continuously monitored for body weight, urine volume, blood sugar and glycated haemoglobin. In the first month of the study, all animals were tested for thermal nociception in a Hargreaves apparatus, weekly. After the first month this was done biweekly and then monthly. The testing consists of directing an infrared heat source onto the dorsal surface of the rat hindpaw and noting the time taken for the animal to remove its paw (for detailed method see Hargreaves et al. 1998). Each animal was tested 8 times and the mean withdrawal latency noted.

Figure 24:
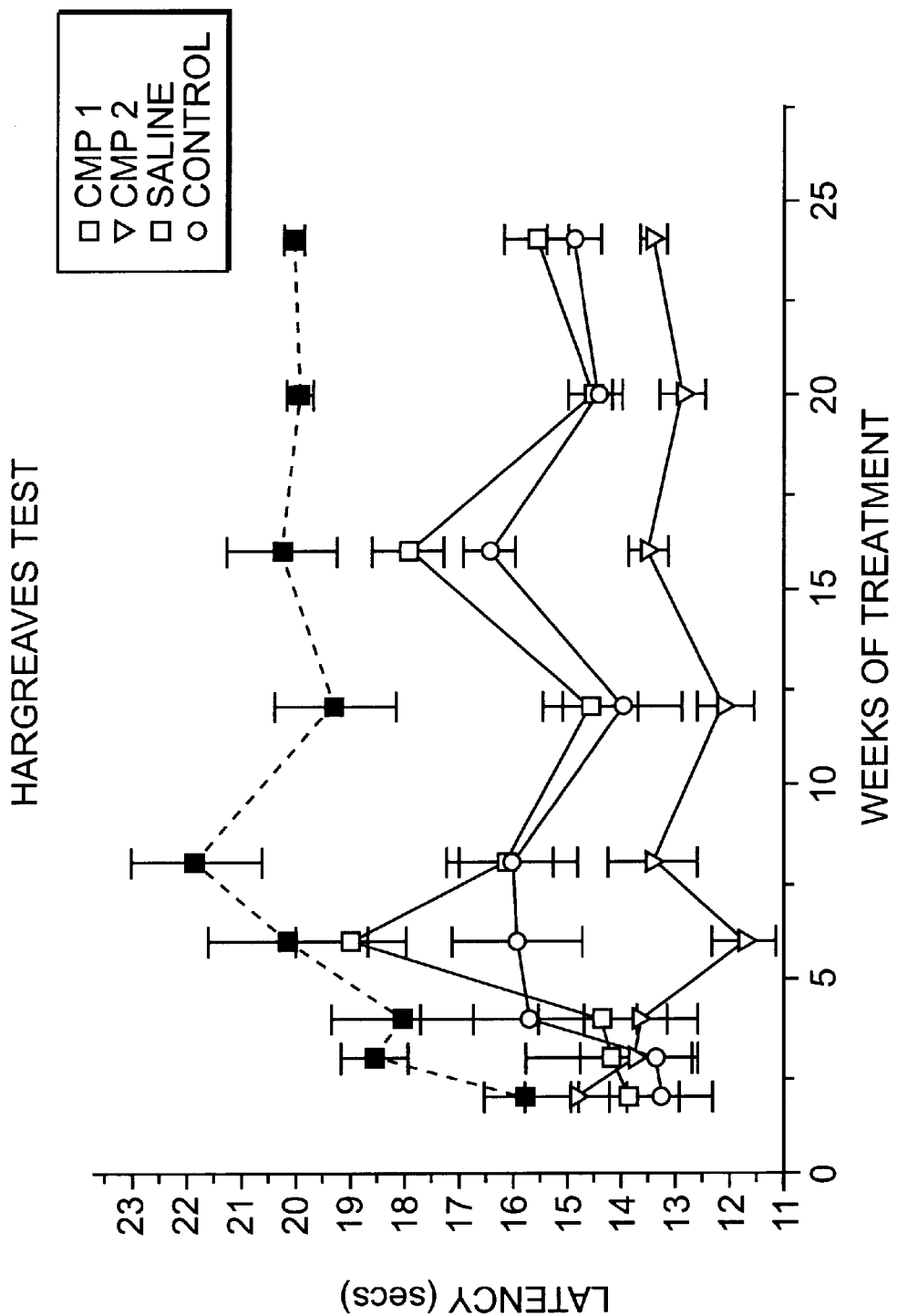
FIG. 24 is a graph plotting the withdrawal latency of non-diabetic rats and BB/W diabetic rats treated with a vehicle, Compound 1 or Compound 2, against the weeks of treatment.

The results are graphically presented in FIG. 24. The results show that diabetic rats displayed a hyperalgesia (shorter response latency) compared to non-diabetic controls. Diabetic drug-treated rats (both Compound 1 and Compound 2) displayed longer withdrawal latencies than diabetic vehicle-treated rats, starting after 4 weeks of treatment and persisting through the six months of treatment.

Figure 25:
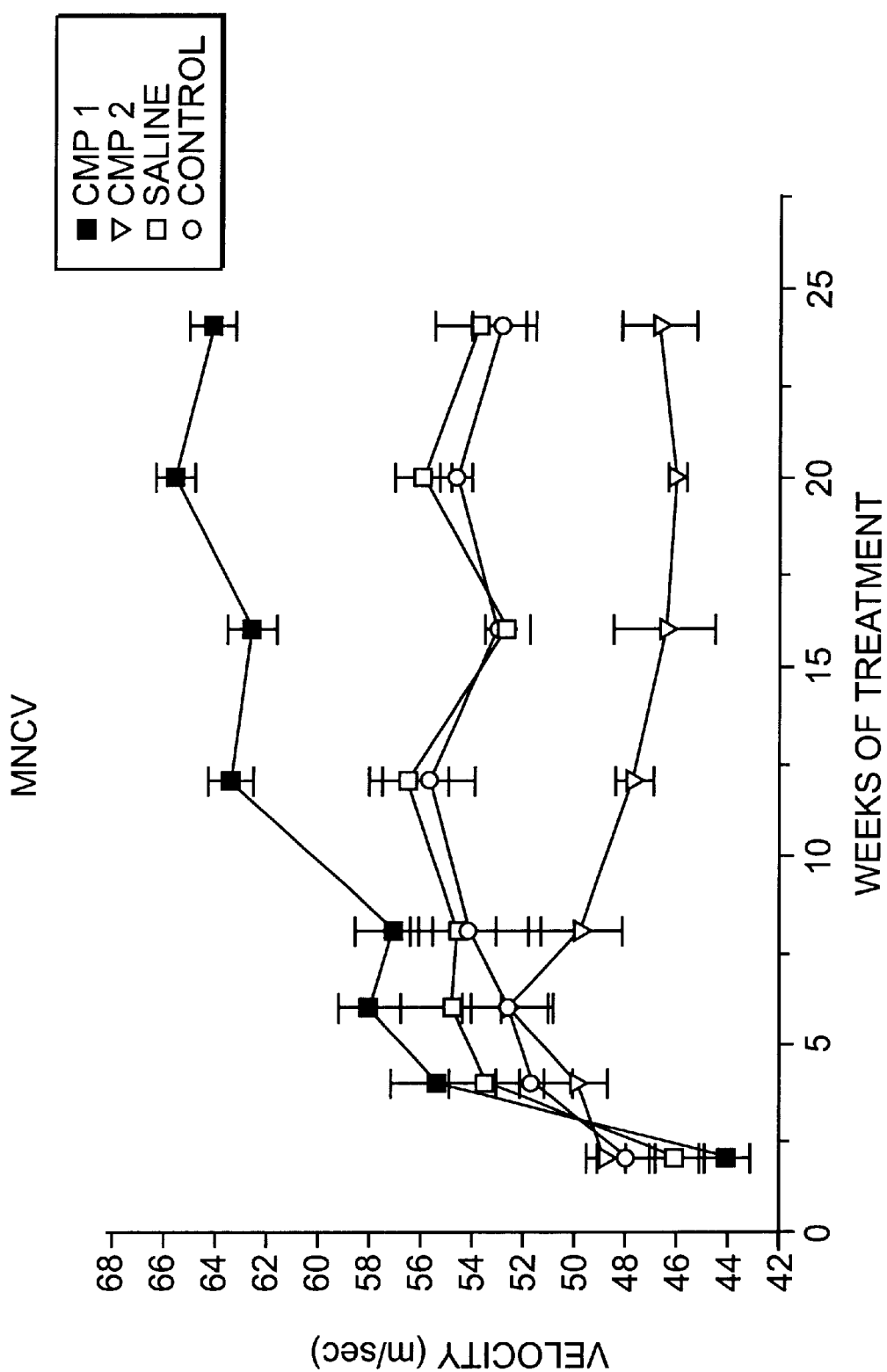
FIG. 25 is a graph plotting the nerve conduction velocity of non-diabetic rats and BB/W diabetic rats treated with a vehicle, Compound 1 or Compound 2, against the weeks of treatment.

Nerve conduction velocity was also measured every two weeks through the first eight weeks of treatment and every month thereafter through to the six months of treatment (see De Koning et al. 1987 for method details). The results are graphically presented in FIG. 25. Diabetic animals generally showed a reduction in nerve conduction velocity compared to non-di abetic controls. However, diabetic animals receiving daily injections of NAALADase inhibitor (either Compound 1 or Compound 2 at a dose of 10 mg/kg) showed significantly less severe nerve conduction deficits than did the diabetic controls receiving vehicle treatment. This was apparent starting at 8 weeks of treatment and persisted to a similar degree through the six month termination point of the study. Diabetic vehicles, on the other hand, showed a progressive deterioration in nerve conduction velocity from 6 to 16 weeks after start of vehicle administration which was maintained through to six months.

In Vivo Assay of NAALADase Inhibitors on Diabetic Neuropathy

Motor and sensory nerve conduction velocity was also measured in STZ-diabetic animals after 4, 8 and 12 weeks of treatment (see De Koning and Gispen 1987 for detailed method). Briefly, stimulating needle electrodes were inserted close to the sciatic and tibial nerves with recording electrodes being placed subcutaneously over the distal foot muscles, in anesthetized rats. The results are graphically presented in FIGS. 21A, 21B, 22A and 22B. Diabetic animals receiving vehicle showed a significant reduction in both motor and sensory nerve conduction compared to non-diabetic animals. Treatment with 10 mg/kg of Compound 2 daily for 4, 8 and 12 weeks all tended to improve (increase) both motor and sensory nerve conduction velocities, with a significant improvement being observed after 12 weeks and 8 weeks for motor and sensory nerve conduction velocity, respectively (FIG. 31A). The lower dose of Compound 2 tested (1 mg/kg) had similar effects (FIG. 31B). Treatment of animals with Compound 1 at either dose also increased both motor and sensory nerve conduction velocities above that of diabetic controls, significantly so after 12 weeks of treatment for the 10 mg/kg treatment group and at the earlier time periods after treatment with the 1 mg/kg dose (FIGS. 32A and 32B). Thus, the results show that NAALADase inhibition alters the progression of diabetic neuropathy.

In Vivo Assay of NAALADase Inhibitors on Schizophrenia

Figure 26:
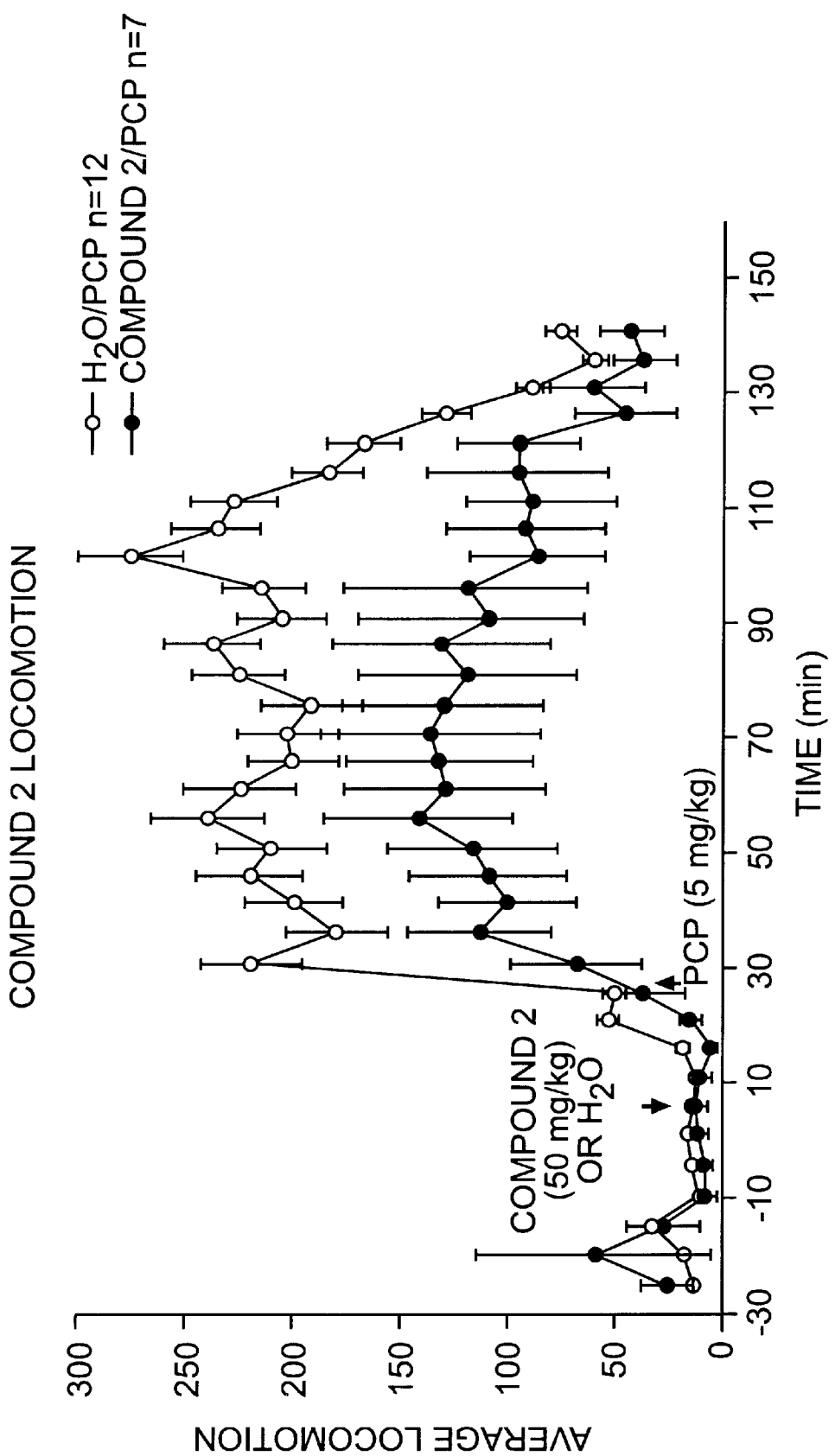
FIG. 26 is a graph plotting the average head rolling scores of PCP-treated rats further treated with water or Compound 2 against the time following PCP administration.
Figure 27:
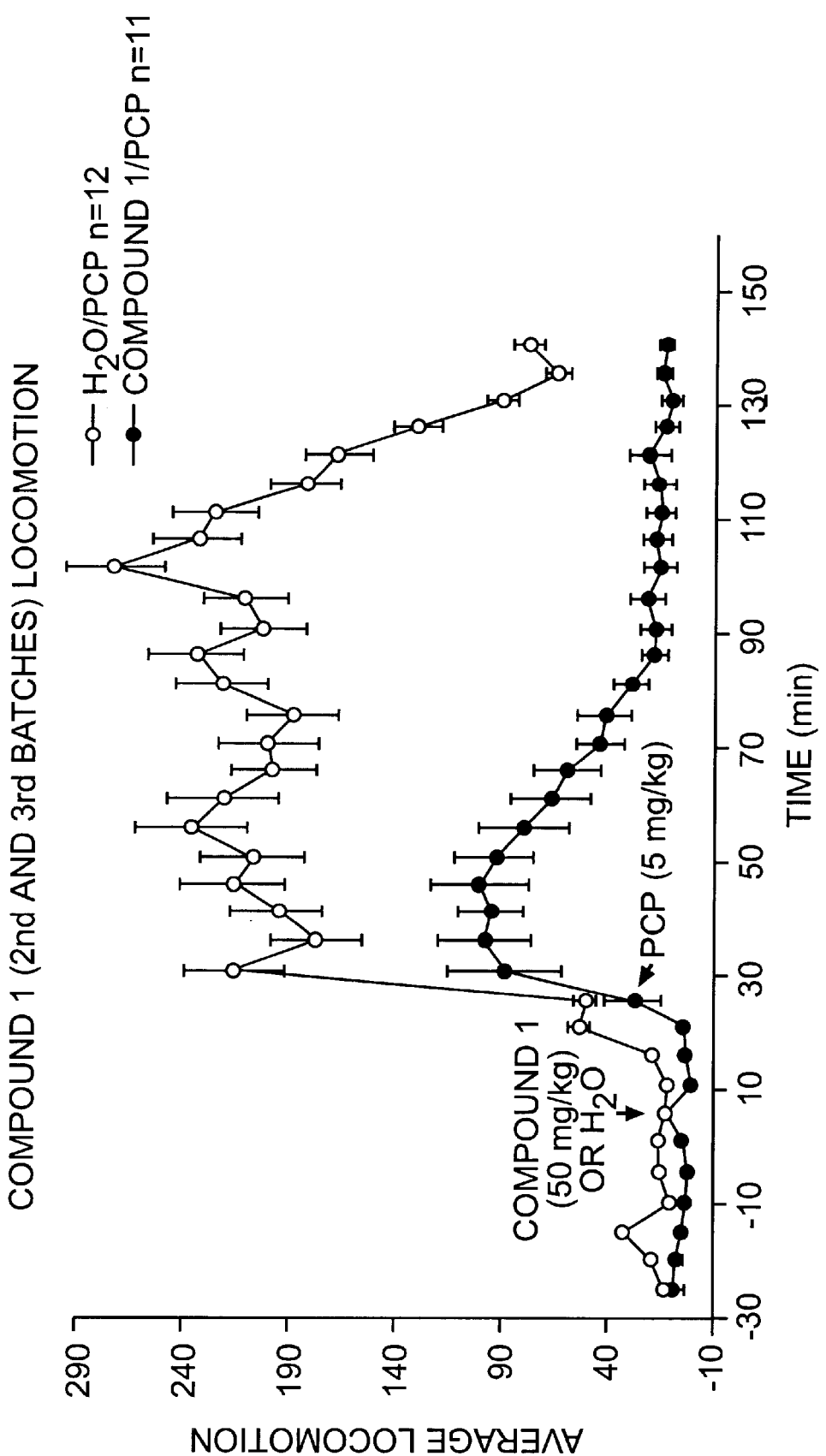
FIG. 27 is a graph plotting the average head rolling scores of PCP-treated rats further treated with water or Compound 1 against the time following PCP administration.

Rats treated with PCP develop symptoms, such as frantic running and incessant head-turning, that parallel psychotic symptoms in humans. Thus, to examine the effects of NAALADase inhibition on schizophrenia, rats were treated intraperitoneally with Compound 1 (50 mg/kg), Compound 2 (50 mg/kg) or a vehicle ($H_2$) before they received PCP (5 mg/kg). Head rolling scores were measured for over 2 hours following PCP injection. The results are graphically presented in FIGS. 26 and 27. The results show that pretreatment with Compound 1 (FIG. 27) or 2 (FIG. 26) significantly reduced the locomotor-activating effects of PCP. Since PCP has been shown to increase glutamate efflux in the prefrontal cortex, the reduction in PCP-induced locomotor activity suggests that NAALADase inhibition ameliorates the behavioral effects of PCP by attenuating presynaptic glutamatergic activity. Thus, NAALADase inhibitors showed efficacy in the PCP model of schizophrenia.

EXAMPLES

The following examples are illustrative of the present invention and are not intended to be limitations thereon. Unless otherwise indicated, all percentages are based upon 100% by weight of the final composition.

EXAMPLE 1

Preparation of 2-[[(2,3,4,5,6-pentafluorobenzyl)-hydroxyphosphinyl]methyl]pentanedioic acid Scheme V: $R_1$=2,3,4,5,6-pentafluorobenzyl Hexamethyldisilazane (21.1 mL, 100 mmol) was added to vigorously stirred ammonium phosphinate (8.30 g, 100 mmol), and the resulting suspension was stirred at 105° C. for 2 hours. A solution of 2,3,4,5,6-pentafluorobenzyl bromide (5.0 g, 27.0 mmol) was then added dropwise to the suspension at 0° C. The mixture was stirred at room temperature for 19 hours. The reaction mixture was then diluted with dichloromethane (50 mL) and washed with 1 N HCl (50 mL). The organic layer was separated, dried over $Na_2SO_4$, and concentrated to give 4.72 g of a white solid. This was dissolved in dichloromethane (50 mL) and benzyl alcohol (3.24 g, 30 mmol)

was added to the solution. 1,3-Dicyclohexyl-carbodiimide (DCC) (6.19 g, 30 mmol) was then added to the solution at 0° C., and the suspension was stirred at room temperature for 14 hours. The solvent was removed under reduced pressure and the residue was suspended in EtOAc. The resulting suspension was filtered and the filtrate was concentrated. The residue was purified by silica gel chromatography (hexanes: EtOAc, 4:1 to 1:1) to give 2-[[(2,3,4,5,6-pentafluorobenzyl)-hydroxyphosphinyl]-methyl]pentanedioic acid as a white solid (34% yield) Rf 0.69 (i-PrOH: $H_2O$, 7:3). $^1$H NMR ($D_2O$): δ 1.8–2.0 (m, 3H), 2.1–2.3 (m, 1H), 2.3–15 2.5 (m, 2H), 2.7–2.9 (m, 2H), 3.29 (d, 2H).

Elemental Analysis

Calculated $C_{13}H_{12}F_5O_6P$, 0.45 $H_2O$: C, 39.20; H, 3.26. Found: C, 39.17; H, 3.28.

EXAMPLE 2

Preparation of 2- (Phosphonomethyl)pentanedioic Acid

Scheme III
Dibenzyl 2-methylenepentanedioate

Benzyl acrylate (500 g, 3.0 mol) was heated in an oil bath to 1000° C. Heating was stopped and HMPT (10 g, 61 mmol) was added dropwise while maintaining an internal temperature below 140° C. Once addition was complete, the mixture was stirred and cooled to room temperature. A slurry of silica (5:1 Hexane/EtOAc) was added and the mixture was placed in a column containing a plug of dry silica. The column was washed with 1:1 Hexane/EtOAc and the fractions were combined and evaporated to give 450 g of clear light golden liquid. The liquid was distilled under high vacuum (200 μHg) at 185° C. to give 212 g (42%) of a clear and colorless liquid. $^1$H NMR ($CDCl_3$): 7.3 ppm (m, 10H), 6.2 ppm (s, 1H), 5.6 ppm (s, 1H), 5.2 ppm (s, 2H), 5.1 ppm (s, 2H), 2.6 ppm (m, 4H).

Dibenzyl 2 -[[bis(benzyloxy)phosphoryl]methyl]pentanedioate

Dibenzyl phosphite (9.5 g, 36 mmol) in 350 ml of dichloromethane was cooled to 0° C. To this stirring solution was added trimethyl aluminum (18.2 ml, 2.0 M solution in hexane, 36.4 mmol). After 30 minutes, dibenzyl 2-methylenepentanedioate (2, 6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried ($MgSO_4$), and evaporated to give a clear light golden liquid. The liquid was chromatographed on silica gel (4 cm*30 cm) and eluted with a gradient (4:1-1:1) solvent system (Hexane/EtOAc). The fractions containing the desired product were combined and evaporated to yield dibenzyl 2- [[bis(benzyloxy)phosphoryl]methyl]pentanedioate (7.1 g, 42%) as a clear and colorless liquid. The liquid was then distilled on a Kughleror apparatus at 0.5 mm Hg and 195–200° C. The distillate was discarded and the remaining light golden oil was chromatographed on silica gel (1:1, Hexane/EtOAc) to give 2.9 g of dibenzyl 2- [[bis(benzyloxy)phosphoryl]methyl]pentanedioate as a clear and colorless oil. TLC Rf 0.5 (1:1 Hexane/EtOAc). $^1$H NMR ($CDCl_3$): 7.1–7.4 (m, 20H), 5.05 (s, 2H), 4.8–5.03 (m, 6H), 2.8 (1H), 2.22–2.40 (m, 3H), 1.80–2.02 (m, 3H).

2-(Phosphonomethyl)pentanedioic Acid

The benzyl pentanedioate (2.9 g, 4.9 mmol) was added to a mixture of 20 ml of methanol containing 0.29 g (6 mol%) of 10% Pd/C. This mixture was hydrogenated on a Parr hydrogenator at 40 psi for 24 hours, filtered and evaporated to give a clear slightly golden viscous oil (3, 1.0 g, 90%). $^1$H-NMR ($D_2O$): 2.6–2.78 (m, 1H), 2.25–2.40 (m, 2H) 1.75–2.15 (m, 4H)

EXAMPLE 3

Preparation of 2-[[[2-(carboxy)propyl]hydroxyphosphinyl]methyl]pentanedioic acid Scheme X
Di-tert-butyl 2-methylenepentanedioate Tert-butyl acrylate (465 g, 3.628 mol) was warmed to 100° C. under nitrogen, then hexamethylphosphorous triamide (10 g, 61.2 mmol) was added dropwise and the addition rate was adjusted to maintain the reaction temperature at 100° C. The reaction mixture was allowed to cool, then poured over a plug of silica (~1000 ml) and washed completely off the silica with 4:1 hexane/ethyl acetate. The solvent was removed under reduced pressure and the resulting oil was distilled. Some material was collected from room temperature to 50° C. under high vacuum, and discarded. The temperature was then raised to ~80° C. and the product (300 g, 65 %, b.p. 67–70° C. at 300μ) was collected as a clear oil. $^1$H NMR ($CDCl_3$): δ 1.4 (m, 18H), 2.4 (t, 2H), 2.6 (t, 2H), 5.5 (s, 1H), 6.0 (s, 1H).

Di-tert-butyl 2-[(hydroxyphosphinyl)methyl])pentanedioate

A mixture of ammonium phosphinate (162.6 g, 1.96 mol) and 1,1,1,3,3,3-hexamethyldisilazane (316 g, 1.96 mol) was heated to 105° C. for 2 hours. The reaction mixture was cooled in an ice bath and di-tert-butyl 2-methylenepentane-1,5-dioate (251 g, 0.979 mol) dissolved in dichloromethane (1000 ml) was added dropwise. The reaction mixture was allowed to warm to room temperature overnight. The reaction mixture was then quenched with distilled water (500 ml) and the organic layer was retained. The aqueous layer was washed a second time with dichloromethane and the combined organic layers were dried over magnesium sulfate. Then the solvent was removed under reduced pressure leaving a slightly yellow oil (315 g, 100%) This product was found to be of sufficient purity for use in the next reaction. $^1$H NMR ($CDCl_3$) δ 1.4 (m, 18H), 1.9 (m, 3H), 2.1 (m, 1H), 2.3 (m, 2H), 2.7 (m, 1H), 6.5 & 7.9 (d, 1H, the P-H), 11.0 (s, 1H).

Di-tert-butyl 2-[(tert-butoxyphosphinyl)methyl]pentanedioate

To a solution of di-tert-butyl 2-[(hydroxy-phosphinyl) methyl]pentane-1,5-dioate (315 g, 0.977 mol) in dichloromethane (1000 ml) cooled in an ice bath and under nitrogen were added tert-butanol (123.1 g, 1.66 mol), 4-dimethylaminopyridine (1 g, 8.2 mmol), andl-ethyl-3-(3-dimethylaminopropyl) carbodiimide (281 g, 1.47 mol). The reaction was allowed to stir overnight. Water was added to the reaction mixture and the dichloromethane layer was retained and dried, and the solvent was removed under reduced pressure. The resulting residue was purified by column chromatography and the desired product was eluted with 1:1 to 2:3 hexane/ethyl acetate. The fractions containing product were concentrated under reduced pressure leaving a clear oil (260 g, 70%). $^1$H NMR ($CDCl_3$) : δ 1.4 (m, 27H), 1.8 (m, 1H), 1.9 (m, 2H), 2.1 (m, 1H), 2.3 (m, 2H), 2.7–2.8 (m, 1H), 6.7 & 8.0 (d, 1H, the P-H).

Di-tert-butyl 2-[[[2-(benzylcarboxy)propyl]tert-butoxyphosphinyl]methyl]pentanedioate To a solution of di-tert-butyl 2-[(tert-butoxy-phosphinyl) methyl]pentane-l,5-dioate (13.62 g, 36.0 mmol) and benzyl methacrylate (6.35 g, 36.0 mmol) in THF (100 ml) under nitrogen was added sodium hydride (0.14 g, 60% dispersion in oil, 3.60 mmol). After three hours, the reaction mixture was poured into water (300 ml) and ether (100 ml) was added. The organic layer was separated and retained, and the aqueous layer was washed again with ether (100 ml). The combined organic extracts were dried over magnesium sulfate and the solvent was removed under reduced pressure. The resulting residue was purified by column chromatography and the product was eluted with 2:3 EtOAc/Hexane. The solvent was removed under reduced pressure leaving a clear oil (10.5 g, 53%). $^1$H NMR (CDCl$_3$) : δ 1.3 (m, 3H), 1.5 (m, 27H), 1.7 (m, 2H), 1.9 (m, 2H), 2.2 (m, 4H), 2.6 (m, 1H), 2.9 (m, 1H), 5.1 (m, 2H), 7.3 (m, 5H).

2-[[[2-(Benzylcarboxy)propyl]hydroxyphosphinyl]-methyl] pentanedioic acid

To a solution of di-tert-butyl 2-[[[2-(benzyl-carboxy) propyl]tert-butoxyphosphinyl]methyl] pentane-1,5-dioate (1.6 g, 2.89 mmol) in dichloromethane (10 ml) under nitrogen was added trifluoroacetic acid (10 ml). The reaction mixture was stirred for two hours and then concentrated under reduced pressure. Additional dichloromethane was added to the reaction residue and removed under reduced pressure. The product was dissolved in ethyl acetate and washed with water, then the organic layer was dried over magnesium sulfate and the solvent was removed under reduced pressure leaving a clear oil (800 mg, 72%). $^1$H NMR (D$_2$O): δ 1.2 (m, 3H), 1.6–1.8 (m, 4H), 2.1 (m, 2H), 2.2 (m, 2H), 2.6 (m, 1H), 2.8 (m, 1H), 5.0 (m, 2H), 7.3 (m, 5H). Analysis calculated for C$_{17}$H$_{23}$PO$_8$ 1.0 H$_2$O: C, 50.50; H, 6.23. Found: C, 50.52; H, 5.92.

Di-tert-butyl 2-[[[2-(carboxy)propyl]tert-butoxy-phosphinyl]methyl]pentanedioate A solution of di-tert-butyl 2-[[[2-(benzyl-carboxy)propyl] tert-butoxyphosphinyl]methyl]pentane-1,5-dioate (8.9 g, 16.1 mmol), palladium on carbon catalyst (10%, 1.0 g) and ethyl acetate (100 ml) was shaken under hydrogen (60 psi) for 16 hours. The reaction mixture was filtered over celite and the filtrate was concentrated under reduced pressure leaving a clear oil (7.5 g, 100%). $^1$H NMR (CDCl$_3$): δ 1.3 (d, 3H), 1.4–1.5 (m, 27H), 1.8 (m, 2H), 1.9 (m, 2H), 2.2 (m, 4H), 2.7 (m, 1H), 2.9 (m, 1H).

2-[[[2-(Carboxy)propyl]hydroxyphosphinyl]methyl]-pentanedioic acid

To a solution of di-tert-butyl 2-[[[2-(carboxy)-propyl]tert-butoxyphosphinyl]methyl]pentane-1, 5-dioate (2.1 g, 4.53 mmol) in dichloromethane (10 ml) under nitrogen was added trifluoroacetic acid (10 ml). The reaction mixture was stirred for two hours and then concentrated under reduced pressure. Additional dichloromethane was added to the reaction residue and removed under reduced pressure. The resulting residue was triturated with acetonitrile, then dried under reduced pressure leaving a thick clear oil (1.2 g, 89%). $^1$H NMR (D$_2$O) δ 1.2 (d, 3H), 1.9 (m, 4H), 2.2 (m, 2H), 2.4 (m, 2H), 2.8 (m, 2H). Analysis calculated for C$_{10}$H$_{17}$PO$_8$ 0.2 CH$_3$CN: C, 41.03; H, 5.83. Found: C, 41.05; H, 5.92.

EXAMPLE 4

Preparation of 2-[({[Benzylamino]methyl} (hydroxy-phosphinyl)) methyl]pentanedioic acid Scheme XI Di-tert-butyl 2-[((tert-butoxy){[benzylamino]methyl}-phosphoryl) methyl]pentane-1,5-dioate A solution of 1,3,5-tribenzylhexahydro-1,3,5-triazine (14.30 g, 40.0 mmol) and di-tert-butyl 2-{[(tert-butoxy) phosphoryl]methyl}pentane-1,5-dioate (37.85 g, 100 mmol) in toluene (200 mL) was stirred at 110° C. for 14 hours. The solvent was removed under reduced pressure and the residual yellow oil was purified by silica gel chromatography (hexanes/ethyl acetate, 2/1) to give 23.40 g of light yellow oil (43% yield).: $^1$H NMR (CDCl$_3$) δ 1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H)

2-[({[Benzylamino]methyl}(hydroxyphosphinyl))methyl]-pentanedioic acid

To a solution of di-tert-butyl 2-[((tert-butoxy)-{[benzylamino]methyl}phosphoryl)methyl]pentane-1,5-dioate (0.498 g, 1.0 mmol) in dichloromethane (10 mL) was added trifluoroacetic acid (5 mL) at 0° C., and the mixture was stirred at room temperature for eighteen hours. The solvent was removed under reduced pressure. The residual oil was taken up with dichloromethane (10 mL) and concentrated. This process was repeated three times to remove trifluoroacetic acid completely. The resulting oil was crystallized from methanol to give 0.174 g of white solid (53% yield): $^1$H NMR (D$_2$O) δ 1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H).

EXAMPLE 5

Preparation of 2-[({[phenylamino]methyl}(hydroxyphosphinyl)) methyl]pentanedioic acid Using a method similar to that described above in Example 4, 2-[({[phenylamino]methyl}(hydroxyphosphinyl)) methyl]pentanedioic acid was synthesized: $^1$H NMR (D$_2$O) δ 1.4–1.6 (m, 1H), 1.7–1.9 (m, 3H), 2.2–2.4 (m, 2H), 2.2–2.4 (m, 2H), 2.5–2.7 (m, 1H), 3.53 (d, J=8.8 Hz, 2H), 7.3–7.5 (m, 5H).

EXAMPLE 6

Preparation of 2-[({[4-fluorophenylamino]methyl}-(hydroxyphosphinyl)) methyl]pentanedioic acid Using a method similar to that described above in Example 4, 2-[({[4-fluorophenylamine]methyl}(hydroxyphosphinyl)) methyl]pentanedioic acid was synthesized: $^1$H NMR (D$_2$O) δ 1.5–1.7 (m, 1H), 1.8–2.0 (m, 3H), 2.3–2.5 (m, 2H), 2.6–2.7 (m, 1H), 3.84 (d, J=9.0 Hz, 2H), 7.2–7.5 (4H)

EXAMPLE 7

Preparation of 2-[({[4-methoxyphenylamino] methyl}-(hydroxyphosphinyl)) methyl]pentanedioic acid Using a method similar to that described above in Example 4, 2-[({[4-Methoxyphenylamino]methyl}-(hydroxyphosphinyl)) methyl]pentanedioic acid was synthesized: $^1$H NMR (D$_2$O) δ 1.2–1.3 (m, 1H), 1.6–1.7 (m, 3H), 2.22–2.23 (m, 2H), 2.3–2.5 (m, 1H), 3.4 (d, J=8.9 Hz, 2H), 3.7 (s, 3H), 7.0 (d, J=12 Hz, 2H), 7.4 (d, J=12 Hz, 2H).

EXAMPLE 8

Preparation of 2-({[(phenylsulfonamido)methyl]-(hydroxyphosphinyl)}methyl)pentanedioic acid Using a method similar to that described above in Example 4, 2-({[(phenylsulfonamido)methyl](hydroxyphosphinyl)}methyl) pentanedioic acid was synthesized: $^1$H NMR (D$_2$O) δ 1.6–2.1 (m, 4H), 2.3–2.4 (m, 2H), 2.5–2.7 (m, 1H), 2.9–3.1 (m, 2H), 7.7–8.0 (m, 5H).

EXAMPLE 9

Preparation of 2-({[(phenylcarboxamido)methyl]-(hydroxyphosphinyl)}methyl)pentanedioic acid Scheme XII Di-tert-butyl 2-{[(aminomethyl) (tert-butoxy)-phosphoryl] methyl}pentane-1,5 -dioate To a solution of di-tert-butyl 2-[((tert-butoxy)-{[benzylamino]methyl}phosphoryl)methyl]pentane-1,5- dioate (8.20 g, 16.5 mmol) in ethanol (100 mL) was added palladium on carbon (0.50 g), and the suspension was shaken under hydrogen (50 psi) for 4 days. The catalyst was removed by filtration through a pad of Celite. The filtrate was concentrated to give 6.629 g of colorless oil (99% yield): $^1$H NMR (CD$_3$OD) δ 1.40–1.60 (m, 27H), 1.80–2.00 (m, 3H), 2.2–2.4 (m, 3H), 2.7–3.0 (m, 3H).

Di-tert-butyl 2-({(tert-butoxy)[(phenylcarboxamido)-methyl]phosphoryl}methyl)pentane-1,5-dioate To a solution of di-tert-butyl 2-{[(aminomethyl)-(tert-butoxy) phosphoryl]methyl}pentane-1,5-dioate (1.222 g, 3.0 mmol) and benzoyl chloride (0.46 mL, 4.0 mmol) in dichloromethane (10 mL) was added triethylamine (0.56 mL, 4.0 mmol) at 0° C., and the mixture was stirred at room temperature for 16 hours. The reaction mixture was diluted with dichloromethane (15 mL), washed with 1 N HCl (25 mL), dried over Na$_2$SO$_4$, and concentrated. The crude material was purified by silica gel chromatography (ethyl acetate/hexanes=2/1) to give 1.259 g of colorless oil (74% yield): $^1$H NMR (CDCl$_3$) δ 1.30–1.60 (m, 27H), 1.60–2.00 (m, 3H), 2.20–2.40 (m, 3H), 2.70–2.90 (m, 3H), 3.5–4.2 (m, 2H), 7.0–7.3 (m, 1H), 7.4–7.6 (m, 3H), 7.8–7.9 (m, 1H)

2-({[(Phenylcarboxamido)methyl](hydroxyphosphinyl)}-methyl)pentanedioic acid

To a solution of di-tert-butyl 2-({(tert-butoxy)-[(phenylcarboxamido)methyl]phosphoryl}methyl)pentane-1,5-dioate (1.230 g, 2.4 mmol) in dichloromethane (10 mL) was added trifluoroacetic acid (5 mL) at room temperature, and the mixture was stirred at room temperature for 18 hours. The solvent was removed under reduced pressure. The residual oil was taken up with dichloromethane (10 mL) and concentrated. This process was repeated three times to remove trifluoroacetic acid completely. The resulting oil was crystallized from acetonitrile-water to give 0.620 g of white solid (75% yield): $^1$H NMR (D$_2$O) δ 1.9–2.1 (m, 3H), 2.2–2.4 (m, 1H), 2.4–2.6 (m, 2H), 2.8–3.0 (m, 1H), 3.7–3.9 (m, 2H), 7.5–7.9 (m, 5H)

EXAMPLE 10

Preparation of 2-(2-sulfanylethyl)pentanedioic acid

Scheme XIII, R$_{10}$=hydrogen 3-(2-Oxotetrahydro-3-thiophenyl)propanoate

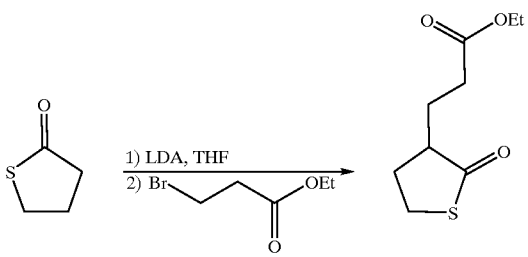

To a cooled solution (−78° C.) of lithium diisopropylamide (LDA) (98 mmol) in THF (100 ml) was added dropwise γ-thiobutyrolactone (10 g, 98 mmol). After stirring for fifteen minutes, ethyl 3-bromopropanoate (35.4 g, 196 mmol) was added and the reaction allowed to warm to room temperature overnight. The solvent was removed under reduced pressure and the resulting residue was purified by column chromatography yielding 3 g (16%) of clear oil. $^1$H NMR (CDCl$_3$) δ 1.2 (t, 3H), 1.7 (m, 1H), 1.9 (m, 1H), 2.1 (m, 1H), 2.4 (t, 2H), 2.5 (m, 2H), 3.3 (t, 2H), 4.2 (q, 2H)

2-(2-sulfanylethyl)pentanedioic acid

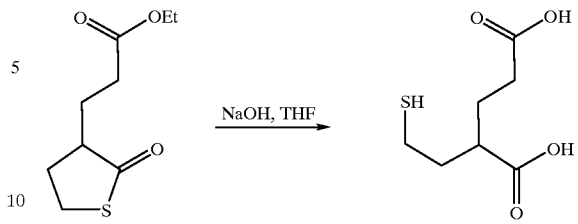

To a solution of ethyl 3-(2-oxotetrahydro-3-thiophenyl) propanoate (0.77 g, 3.81 mmol) in THF (5 ml) was added sodium hydroxide (1 M in water, 5 ml). The mixture was allowed to stir for two days, then the THF was removed under reduced pressure, the aqueous layer was washed with ether, then acidified to pH 1 with HCl and extracted with ethyl acetate. The combined ethyl acetate extracts were dried over magnesium sulfate and the solvent was removed under reduced pressure. The resulting residue was purified by column chromatography yielding a 150 mg of clear oil (20%). $^1$H NMR (d6-DMSO) δ 1.7 (m, 3H), 1.8 (m, 1H), 2.2 (m, 2H), 2.3–2.5 (m, 4H). Analysis calculated for C$_7$H$_{12}$SO$_4$: C, 43.74; H, 6.29; S, 16.68. Found: C, 43.61; H, 6.39; S, 16.55.

EXAMPLE 11

Preparation of 2-(3-sulfanylpropyl)pentanedioic acid

Scheme XIX 2,2-dimethyl-5-[3-[(triphenylmethyl)thio]propyl]-1,3-dioxane-4,6-dione (I)

20 mmol of 3-[(triphenylmethyl)thio]propionic acid (6.9 g) was dissolved with 22 mmol Meldrum's acid (2,2-dimethyl-1,3-dioxane-4,6-dione) (3.2 g) and 31 mmol 4-dimethylaminopyridine (3.85 g) in 100 ml CH$_2$Cl$_2$. The reaction mixture was cooled to −5° C. and a solution of 22 mmol of dicyclohexyl carbodiimide (4.74 g) in 50 ml CH$_2$Cl$_2$ was added dropwise over 1 hour. The mixture was left at <0° C. temperature overnight, during which time tiny crystals of dicyclohexylurea precipitated. After filtration, the reaction mixture was washed 4× with 10% KHSO$_4$, 1× with brine and dried with MgSO$_4$ for 2 hours. This solution was used for the second step without characterization or further purification.

The solution from the previous reaction was cooled to −5° C. and 13.3 ml (220 mmol) of 98% acetic acid was added. Then 1.85 g (50 mmol) of NaBH$_4$, was added in small portions while stirring over 1 hour. The reaction mixture was left in the refrigerator overnight and then washed 3× with water and 2× with brine. Organic phase was dried with MgSO$_4$, filtered and evaporated to dryness. The residue was dissolved in EtOAc, the precipitated small amount of dicyclohexylurea was filtered off and filtrate was brought to crystallization by addition of hexane. Yield 7.5 g of 2,2-dimethyl-5-[3-[(triphenylmethyl)-thio]propyl]-1,3-dioxane-4,6-dione (I) (86% - two steps). $_{13}$C-NMR δ 20.0(q), 26.2 (q), 27.2(t), 28.9(t), 32.0(t), 46.2(d), 67.0(s), 105.3(s), 127.0 (d), 128.3(d), 130.0(d), 145.2(s), 165.6(s).

2,2-Dimethyl-4,6-dioxo-5-[3-[(triphenylmethyl) thio]-propyl]-1,3-dioxane-5-propanoic acid methylester (II)

5 mmol of 2,2-dimethyl-5-[3-[(triphenylmethyl)-thio]-propyl]-1,3-dioxane-5-propanoic-4,6-dione (I) (2.3 g), was dissolved with 20 mmol methyl-3-bromopropionate (3.34g= 2.18 ml) and 4.6 ml of 4.37 M methanolic solution of sodium methoxide (20 mmol) in 10 ml of methanol. The reaction mixture was heated to 60° C. overnight after which TLC in hexane/ethylacetate 1:1 detected no starting material. The mixture was then evaporated to dryness and mixed with 40 ml of aqueous 10% $KHSO_4$. The organic material was extracted by 3 portions of EtOAc, the organic layers were combined dried with $MgSO_4$ and evaporated. The residue was crystallized from hexane/ethylacetate to yield 2.1 g (77%) of 2,2-dimethyl-4,6-dioxo-5-[3-[(triphenyl-methyl)thio]propyl]-1,3-dioxane-5-propanoic acid methyl ester (II), $^{13}$C-NMR ($CDCl_3$) δ 24.6, 29.4, 29.5, 29.6, 31.4, 32.6, 37.7, 51.9, 52.8, 66.8, 105.7, 126.7, 127.9, 129.5, 144.7, 168.4, 172.0.

6-[(triphenylmethyl)thio]-1,3,3-hexanetricarboxylic acid (III)

2.56 mmol of 2,2-dimethyl-4,6-dioxo-5-[3-[(triphenylmethyl)thio]propyl]-1,3-dioxane-5-propanoic acid methyl ester (II) (1.4 g) with 18 mmol of sodium hydroxide (0.72 g) was dissolved in a mixture of 5 ml of 1,4-dioxane and 5 ml of water. The mixture was then heated to 100° C. for 1 hour, evaporated to dryness, dissolved in water and precipitated by addition of 1 M sulfuric acid. The precipitate was filtered off, washed with water and dried in a dessicator. Yield 1.36 g of 6-[(triphenylmethyl)-thio ]-1,3,3-hexanetricarboxylic acid (III) (~100%), $^{13}$C-NMR (MeOH) δ 25.4, 29.2, 30.7, 33.5, 33.7, 58.0, 68.3, 128.1, 129.3, 131.2, 146.7, 174.9, 176.9.

6-[(triphenylmethyl)thio]-1,3-hexanedicarboxylic acid (IV)

2.56 mmol of 6-[((triphenylmethyl)thio]-1,3,3,-hexanetricarboxylic acid (III) (1.36 g) was dissolved in 5 ml of dimethylsulfoxide and the solution was heated to 100° C. for 1 hour, evaporated to dryness, dissolved in water and precipitated by addition of 1 M sulfuric acid. The precipitated oil solidified after 1 hour treatment in an ultrasound bath. The solid was filtered off, washed with water and dried in a dessicator. Yield 1.1 g of 6-[(triphenylmethyl)-thio ]-1,3-hexanedicarboxylic acid (IV) (89% two steps from II), $^{13}$C-NMR (MeOH) δ 27.9, 28.6, 33.0 (two carbons), 33.1, 45.9, 68.1, 128.1, 129.2, 131.2, 146.8, 177.1, 179.4.

2-(3-sulfanylpropyl)pentanedioic acid (V)

2.46 mmol of 6-[(triphenylmethyl)thio]-1,3-hexanedicarboxylic acid (IV) (1.1 g) with 5 mmol triisopropylsilane (0.79 g) was dissolved in a mixture of 3 ml $CH_2Cl_2$/3 ml trifluoroacetic acid and left to stand at room temperature for 1 hour. The mixture was then evaporated to dryness and washed 3× with hexane. The remaining oily residue was dissolved in water, filtered and lyophilized to yield 0.35 g of 2-(3-sulfanylpropyl) pentanedioic acid (V) (76%), $^{13}$C-NMR (MeOH) δ 25.2(t), 28.8(t), 32.4(t), 33.0(t), 33.2(t), 45.9(d), 177.2(s), 179.6(s).

EXAMPLE 12

Preparation of 2-(4-sulfanylbutyl)pentanedioic acid 2-(4-sulfanylbutyl)pentanedioic acid was prepared using the methods described above for 2-(3-sulfanylpropyl) pentanedioic acid. $^{13}$C-NMR (MeOH) δ 25.1(t), 27.4(t), 28.8(t), 33.0(t), 33.2(t), 35.4(t), 46.3(d), 177.2(s), 179.7(s).

EXAMPLE 13

Preparation of 2-(3-sulfanyl-2-methylpropyl)-pentanedioic acid 2-(3-Sulfanyl-2-methylpropyl)pentanedioic acid (mixture of two diastereoisomers) was prepared using the methods described above for 2-(3-sulfanylpropyl)-pentanedioic acid. $^{13}$C-NMR (MeOH) δ 18.9(q), 19.5(q), 29.1(t), 29.6(t), 31.7 (t), 32.6(t), 32.9(t), 33.0(t), 35.5(d), 35.9(d), 39.2(t), 39.7(t), 44.2(d), 44.3(d), 177.0(s), 177.1(s), 179.7(s), 179.9(s).

EXAMPLE 14

2-(2-sulfanylpropyl)pentanedioic acid and 2-(3-sulfanylpropyl) pentanedioic acid are tested in each of the Examples and in vitro and in vivo assays described above. Both compounds are found to exhibit in vitro or in vivo activity in each of their respective assays and Examples.

The invention being thus described, it will be obvious that the same may be varied in many ways. Such variations are not to be regarded as a departure from the spirit and scope of the invention and all such modifications are intended to be included within the scope of the following claims.

We claim:

1. A method for inhibiting NAALADase enzyme activity in a mammal in need thereof, comprising administering to said mammal an effective amount of a compound of formula I

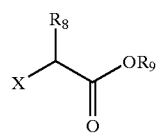

I or a pharmaceutically acceptable equivalent, wherein:

X is a moiety of formula II, III or IV

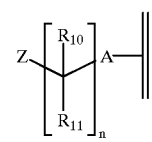

II

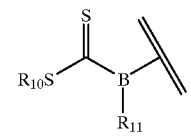

III

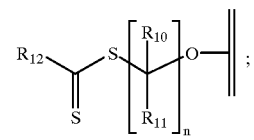

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent (s)

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

2. The method of claim 1, wherein:

Z is SH; and $R_{18}$ is —$(CH_2)_2COOH$.

3. The method of claim 1, wherein the compound of formula I is selected from the group consisting of:

2-(2-sulfanylethyl)pentanedioic acid;

3-(2-sulfanylethyl)-1,3,5-pentanetricarboxylic acid;

2-(2-sulfanylpropyl)pentanedioic acid;

2-(2-sulfanylbutyl)pentanedioic acid;

2-(2-sulfanyl-2-phenlethyl)pentanedioic acid;

2-(2-sulfanylhexyl)pentanedioic acid;

2-(2-sulfanyl-1-methylethyl)pentanedioic acid;

2-[1-(sulfanylmethyl)propyl]pentanedioic acid;

2-(3-sulfanylpentyl)pentanedioic acid;

2-(3-sulfanylpropyl)pentanedioic acid;

2-(3-sulfanyl-2-methylpropyl)pentanedioic acid;

2-(3-sulfanyl-2-phenylpropyl)pentanedioic acid;

2-(3-sulfanylbutyl)pentanedioic acid;

2-[3-sulfanyl-2-(phenylmethyl)propyl]pentanedioic acid;

2-[2-(sulfanylmethyl)butyl]pentanedioic acid;

2-[2-(sulfanylmethyl)pentyl]pentanedioic acid;

2-(3-sulfanyl-4-methylpentyl)pentanedioic acid; and pharmaceutically acceptable equivalents.

4. A method for treating a glutamate abnormality in a mammal in need thereof, comprising administering to said mammal in need thereof an effective amount of a compound of formula I

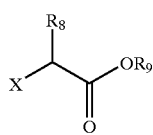

I or a pharmaceutically acceptable equivalent, wherein:

X is a moiety of formula II, III or IV

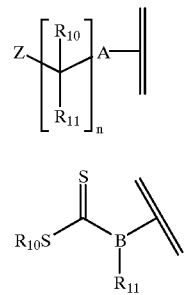

II

III

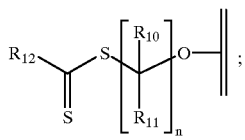

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or. substituted with one or more substituent(s); and $Ar_1$ is a carbocyclic or heterocyclic moiety, which is unsubstituted or substituted with one or more substituent(s);

provided that when X is a moiety of formula III, B is N, and $R_8$ is —$(CH_2)_2COOH$, then $R_{11}$ is not hydrogen; when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0,2,3 or 4, and provided that when X is a moiety of formula II, $R_8$ is —$(CH_2)_2COOH$, A is O or $CR_{17}R_{18}$, and n is 0, then Z is not $SO_2R_{13}$, $SOR_{13}$, or $SO(NR_{13})R_{14}$.

5. The method of claim 4, wherein:

Z is SH; and $R_8$ is —$(CH_2)_2COOH$.

6. The method of claim 4, wherein the glutamate abnormality is ischemia.

7. The method of claim 6, wherein:

Z is SH; and $R_8$ is —$(CH_2)_2COOH$.

8. The method of claim 4, wherein the compound of formula I is selected from the group consisting of:

2-(2-sulfanylethyl)pentanedioic acid;

3-(2-sulfanylethyl)-1,3,5-pentanetricarboxylic acid;

2-(2-sulfanylpropyl)pentanedioic acid;

2-(2-sulfanylbutyl)pentanedioic acid;

2-(2-sulfanyl-2-phenylethyl)pentanedioic acid;

2-(2-sulfanylhexyl)pentanedioic acid;

2-(2-sulfanyl-1-methylethyl)pentanedioic acid;

2-[1-(sulfanylmethyl)propyl]pentanedioic acid;

2-(3-sulfanylpentyl)pentanedioic acid;

2-(3-sulfanylpropyl)pentanedioic acid;

2-(3-sulfanyl-2-methylpropyl)pentanedioic acid;

2-(3-sulfanyl-2-phenylpropyl)pentanedioic acid;

2-(3-sulfanylbutyl)pentanedioic acid;

2-[3-sulfanyl-2-(phenylmethyl)propyl]pentanedioic acid;

2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

9. A method for treating a glutamate abnormality selected from the group consisting of compulsive disorder, stroke, demyelinating disease, schizophrenia, Parkinson's disease and ALS in a mammal is need thereof, comprising administering to said mammal an effective amount of a compound of formula I

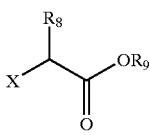
I or a pharmaceutically acceptable equivalent, wherein:
X is a moiety of formula II, III or IV

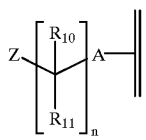
II

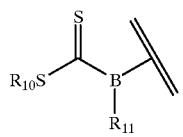
III

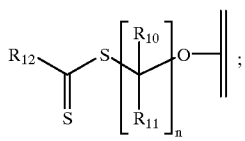
IV m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(NR_{13}R_{14})_2R_{15}$;
B is N or $CR_{16}$;
A is O, S, $CR_{17}R_{18}$ or $(CR_{17}R_{18})_mS$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s);
provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4, and provided that when X is a moiety of formula II, $R_8$ is —$(CH_2)_2COOH$, A is O or $CR_{17}R_{18}$, and n is 0, then Z is not $SO_2R_{13}$, $SOR_{13}$, or $SO(NR_{13})R_{14}$.

10. The method of claim 9, wherein:
Z is SH; and
$R_8$ is —$(CH_2)_2COOH$.

11. The method of claim 9 wherein the glutamate abnormality is schizophrenia.

12. The method of claim 11, wherein:
z is SH; and
$R_8$ is —$(CH_2)_2COOH$.

13. The method of claim 9 wherein the glutamate abnormality is compulsive disorder.

14. The method of claim 13, wherein:
Z is SH; and
$R_8$ is —$(CH_2)_2COOH$.

15. The method of claim 13, wherein the compulsive disorder is selected from the group consisting of drug dependence and eating disorder.

16. The method of claim 15, wherein:
Z is SH; and
$R_8$ is —$(CH_2)_2COOH$.

17. The method of claim 15, wherein the drug dependence is alcohol dependence, nicotine dependence or cocaine dependence.

18. The method of claim 17, wherein:
Z is SH; and
$R_8$ is —$(CH_2)_2COOH$.

19. The method claim 9, wherein the compound of formula I is selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

20. A method for effecting a neuronal activity in a mamnmal in need thereof, comprising administering to said mammal an effective amount of a compound of formula I

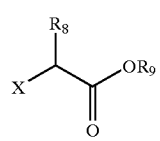
I or a pharmaceutically acceptable equivalent, wherein:

X is a moiety of formula II, III, or IV

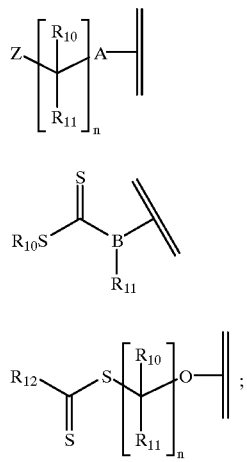

m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4, and provided that when X is a moiety of formula II, $R_8$ is —$(CH_2)_2COOH$, A is O or $CR_{17}R_{18}$, and n is 0, then Z is not $SO_2R_{13}$, $SOR_{13}$, or $SO(NR_{13})R_{14}$.

21. The method of claim 20, wherein:

Z is SH; and $R_8$ is —$(CH_2)_2COOH$.

22. The method of claim 20, wherein the neuronal activity is selected from the group consisting of stimulation of damaged neurons, promotion of neuronal regeneration, prevention of neurodegeneration and treatment of a neurological disorder.

23. The method of claim 22 wherein:

Z is SH; and $R_8$ is —$(CH_2)_2COOH$.

24. The method of claim 22, wherein the neurological disorder is selected from the group consisting of peripheral neuropathy caused by physical injury or disease state, traumatic brain injury, physical damage to spinal cord, stroke associated with brain damage, demyelinating disease and neurological disorder relating to neurodegeneration.

25. The method of claim 24, wherein:

Z is SH; and $R_8$ is —$(CH_2)_2COOH$.

26. The method of claim 24, wherein the neurological disorder relating to neurodegeneration is selected from the group consisting of Parkinson's disease, Huntington's disease, and ALS.

27. The method of claim 26, wherein:

Z is SH; and $R_8$ is —$(CH_2)_2COOH$.

28. The method of claim 20, wherein the compound of formula I is selected from the group consisting of:

2-(2-sulfanylethyl)pentanedioic acid;

3-(2-sulfanylethyl)-1,3,5-pentanetricarboxylic acid;

2-(2-sulfanylpropyl)pentanedioic acid;

2-(2-sulfanylbutyl)pentanedioic acid;

2-(2-sulfanyl-2-phenylethyl)pentanedioic acid;

2-(2-sulfanylhexyl)pentanedioic acid;

2-(2-sulfanyl-1-methylethyl)pentanedioic acid;

2-[1-(sulfanylmethyl)propyl]pentanedioic acid;

2-(3-sulfanylpentyl)pentanedioic acid;

2-(3-sulfanylpropyl)pentanedioic acid;

2-(3-sulfanyl-2-methylpropyl)pentanedioic acid;

2-(3-sulfanyl-2-phenylpropyl)pentanedioic acid;

2-(3-sulfanylbutyl)pentanedioic acid;

2-[3-sulfanyl-2-(phenylmethyl)propyl]pentanedioic acid;

2-[2-(sulfanylmethyl)butyl]pentanedioic acid;

2-[2-(sulfanylmethyl)pentyl]pentanedioic acid;

2-(3-sulfanyl-4-methylpentyl)pentanedioic acid; and pharmaceutically acceptable equivalents.

29. A method for treating a prostate disease in a mammal is need thereof, comprising administering to said mammal an effective amount of a compound of formula I

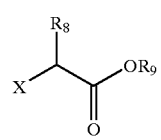

or a pharmaceutically acceptable equivalent, wherein:

X is a moiety of formula II, III or IV

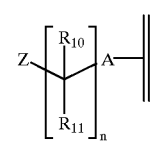

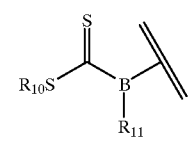

-continued

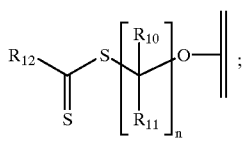

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

30. The method of claim 29, wherein:

Z is SH; and $R_8$ is —$(CH_2)_2COOH$.

31. The method of claim 29, wherein the prostate disease is prostate cancer.

32. The method of claim 31, wherein:

Z is SH; and $R_8$ is —$(CH_2)_2COOH$.

33. The method of claim 29, wherein the compound of formula I is selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

34. A method for treating cancer in a mammal in need thereof, comprising administering to said mammal an effective amount of a compound of formula I

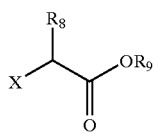

I or a pharmaceutically acceptable equivalent, wherein:

X is a moiety of formula II, III or IV

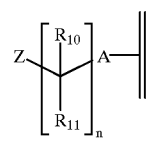

II

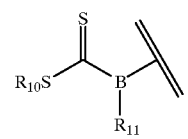

III

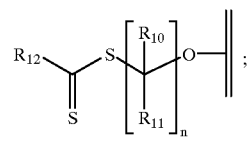

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

35. The method of claim 34, wherein:

Z is SH; and $R_8$ is —$(CH_2)_2COOH$.

36. The method of claim 34, wherein the compound of formula I is selected from the group consisting of:

2-(2-sulfanylethyl)pentanedioic acid;

3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

37. A method for inhibiting angiogenesis in a mammal in need thereof comprising administering to said mammal an effective amount of a NAALADase inhibitor.

38. The method of claim 37, wherein the NAALADase inhibitor is a compound of formula I

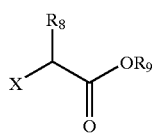

I or a pharmaceutically acceptable equivalent, wherein:
X is a moiety of formula II, III, or IV

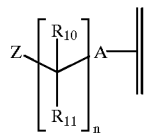

II

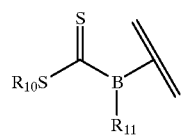

III

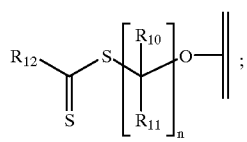

IV m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(NR_{13}R_{14})_2R_{15}$;
B is N or $CR_{16}$;
A is O, S, $CR_{17}R_{18}$ or $(CR_{17}R_{18})_mS$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4.

39. The method of claim 38 wherein:
Z is SH; and
$R_8$ is -$(CH_2)_2COOH$.

40. The method of claim 38, wherein the compound of formula I is selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

41. A method for treating acute pain in a mammal in need thereof comprising administering to said mammal an effective amount of a NAALADase inhibitor.

42. The method of claim 41, wherein the NAALADase inhibitor is a compound of formula I

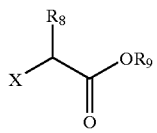

I or a pharmaceutically acceptable equivalent, wherein:
X is a moiety of formula II, III, or IV

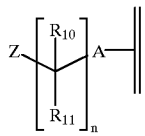

II

-continued

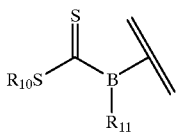
III

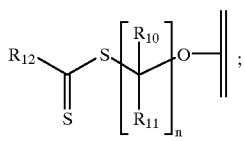
IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4; and provided that when X is a moiety of formula II, $R_8$ is -$(CH_2)_2COOH$, A is O or $CR_{17}R_{18}$, and n is 0, then Z is not $SO_2R_{13}$, $SOR_{13}$ or $SO(NR_{13})R_{14}$.

43. The method of claim 42, wherein:
Z is SH; and
$R_8$ is -$(CH_2)_2COOH$.

44. The method claim 42, wherein the compound of formula I is selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

45. A method for treating diabetic neuropathic pain in a mammal in need thereof comprising administering to said mammal an effective amount of a NAALADase inhibitor.

46. The method of claim 45, wherein the NAALADase inhibitor is a compound of formula I

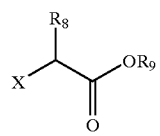
I or a pharmaceutically acceptable equivalent, wherein:
X is a moiety of formula II, III, or IV

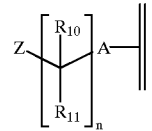
II

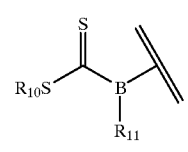
III

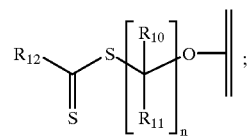
IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4; and provided that when X is a moiety of formula II, $R_8$ is -$(CH_2)_2COOH$, A is O or $CR_{17}R_{18}$, and n is 0, then Z is not $SO_2R_{13}$, $SOR_{13}$ or $SO(NR_{13})R_{14}$.

47. The method of claim 46, wherein:

Z is SH; and $R_8$ is -$(CH_2)_2COOH$.

48. The method of claim 46, wherein the compound of formula I is selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

49. A method for treating diabetic neuropathy in a mammal in need thereof comprising administering to said mammal an effective amount of a NAALADase inhibitor.

50. The method of claim 49, wherein the NAALADase inhibitor is a compound of formula I

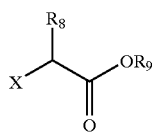

I or a pharmaceutically acceptable equivalent, wherein:

X is a moiety of formula II, III, or IV

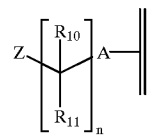

II

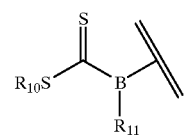

III

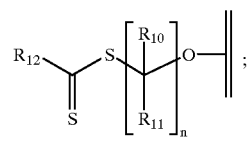

IV m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(NR_{13}R_{14})_2R_{15}$;

B is N or $CR_{16}$;

A is O, S, $CR_{17}R_{18}$ or $(CR_{17}R_{18})_mS$;

$R_9$ and $R_{13}$ are hydrogen;

$R_8$, $R_{10}$, $R_{11}$, $R_{12}$, $R_{14}$, $R_{15}$, $R_{16}$, $R_{17}$ and $R_{18}$ are independently hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4; and provided that when X is a moiety of formula II, $R_8$ is -$(CH_2)_2COOH$, A is O or $CR_{17}R_{18}$, and n is 0, then Z is not $SO_2R_{13}$, $SOR_{13}$ or $SO(NR_{13})R_{14}$.

51. The method of claim 50, wherein:

Z is SH; and $R_8$ is -$(CH_2)_2COOH$.

52. The method of claim 50, wherein the compound of formula I is selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

53. A method for treating pain in a mammal in need thereof comprising administering to said mammal an effective amount of a compound of formula I

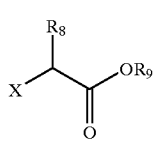

I or a pharmaceutically acceptable equivalent, wherein:
X is a moiety of formula II, III or IV

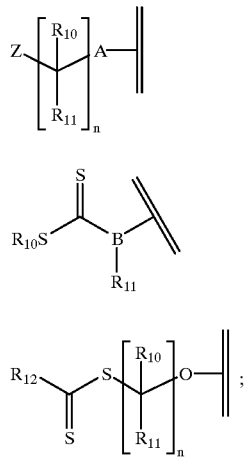

II

III

IV m and n are independently 0, 1, 2, 3 or 4;
Z is $SR_{13}$, $SO_3R_{13}$, $SO_2R_{13}$, $SOR_{13}$, $SO(NR_3)R_{14}$ or $S(NR_{13}R_{14})_2R_{15}$;
B is N or $CR_{16}$;
A is O, S, $CR_{17}R_{18}$ or $(CR_{17}R_{18})_mS$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s);

provided that when X is a moiety of formula II and A is O, then n is 2, 3 or 4; when X is a moiety of formula II and A is S, then n is 2, 3 or 4; and when X is a moiety of formula II and A is $(CR_{17}R_{18})_mS$, then n is 0, 2, 3 or 4, and provided that when X is a moiety of formula II, $R_8$ is —$(CH_2)_2COOH$, A is O or $CR_{17}R_{18}$, and n is 0, then Z is not $SO_2R_{13}$, $SOR_{13}$, or $SO(NR_{13})R_{14}$.

54. The method of claim 53 wherein:
Z is SH; and
$R_8$ is -$(CH_2)_2COOH$.

55. The method of claim 53, wherein the compound of formula I is selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and pharmaceutically acceptable equivalents.

* * * * *